(12) United States Patent
Beane et al.

(10) Patent No.: US 7,510,561 B2
(45) Date of Patent: Mar. 31, 2009

(54) APPARATUS AND METHOD FOR CONNECTING A CONDUIT TO A HOLLOW ORGAN

(75) Inventors: Richard M. Beane, Hingham, MA (US); John W. Brown, Indianapolis, IN (US); James Alan Crunkleton, Weston, MA (US); James S. Gammie, Stevenson, MD (US); Joseph L. Smith, Jr., Concord, MA (US)

(73) Assignee: Correx, Inc., Waltham, MA (US)

( * ) Notice: Subject to any disclaimer, the term of this patent is extended or adjusted under 35 U.S.C. 154(b) by 392 days.

(21) Appl. No.: 11/086,577

(22) Filed: Mar. 23, 2005

(65) Prior Publication Data
US 2005/0251187 A1 Nov. 10, 2005

Related U.S. Application Data

(60) Provisional application No. 60/636,449, filed on Dec. 15, 2004, provisional application No. 60/635,652, filed on Dec. 14, 2004, provisional application No. 60/555,308, filed on Mar. 23, 2004.

(51) Int. Cl.
*A61B 17/11* (2006.01)
(52) U.S. Cl. ...................................... 606/153; 606/184
(58) Field of Classification Search ................. 606/141, 606/153, 184, 185
See application file for complete search history.

(56) References Cited

U.S. PATENT DOCUMENTS

| 4,118,806 A | 10/1978 | Porier et al. |
| 4,769,031 A | 9/1988 | McGough et al. |
| 4,794,928 A | 1/1989 | Kletschka |
| 5,129,913 A * | 7/1992 | Ruppert ...................... 606/184 |
| 5,500,014 A | 3/1996 | Quijano |
| 5,843,088 A | 12/1998 | Barra et al. |
| 6,083,237 A | 7/2000 | Huitema |
| 6,146,325 A | 11/2000 | Lewis |

(Continued)

FOREIGN PATENT DOCUMENTS

| WO | WO 82/01644 A | 5/1982 |
| WO | WO 93/00868 A | 1/1993 |

*Primary Examiner*—Todd E Manahan
*Assistant Examiner*—Ryan Severson
(74) *Attorney, Agent, or Firm*—Pandiscio & Pandiscio

(57) ABSTRACT

An apparatus and method for connecting a first conduit to the heart without the need for cardiopulmonary bypass. The first conduit may then be attached to a second conduit that has a prosthetic device interposed. The second conduit may be connected to the aorta prior to the first conduit being attached to the heart. The prosthetic device may be a prosthetic valve or a pump, for example. The apparatus of the present invention includes an implantable connector with first conduit component, a retractor expansion component, a coring component, and a pushing component. The retractor expansion component is slideably coupled to the coring component. The retractor expansion component serves to seat against and separate the inside apical wall of the left ventricle so that the coring component may cut cleanly through the myocardium to form a tissue plug without leaving any hanging attachments to the inside walls. By remaining seated against the inside wall, the retractor expansion component follows the tissue plug into the coring component. The surgeon applies force and rotary motion to the pushing component sufficient to cut the tissue plug and implant the prosthetic component.

54 Claims, 35 Drawing Sheets

U.S. PATENT DOCUMENTS

| | | |
|---|---|---|
| 6,266,550 B1 | 7/2001 | Selmon |
| 6,409,739 B1 | 6/2002 | Nobles |
| 6,416,527 B1 | 7/2002 | Berg |
| 6,475,222 B1 | 11/2002 | Berg |
| 6,712,831 B1 | 3/2004 | Kaplan |
| 6,726,648 B2 | 4/2004 | Kaplon |
| 6,863,677 B2 | 3/2005 | Breznock |
| 6,942,672 B2 | 9/2005 | Heilman |
| 6,994,666 B2 | 2/2006 | Shannon |
| 7,077,801 B2 | 7/2006 | Haverich |
| 2001/0004675 A1 | 6/2001 | Woodward |
| 2001/0005787 A1 | 6/2001 | Oz et al. |
| 2002/0045846 A1 | 4/2002 | Kaplon et al. |
| 2002/0082467 A1 | 6/2002 | Campbell |
| 2002/0082614 A1* | 6/2002 | Logan et al. ............... 606/139 |
| 2002/0173808 A1 | 11/2002 | Houser |
| 2002/0183584 A1 | 12/2002 | Shannon et al. |
| 2002/0183769 A1* | 12/2002 | Swanson et al. ............ 606/153 |
| 2003/0023255 A1 | 1/2003 | Miles et al. |
| 2003/0040765 A1 | 2/2003 | Breznock |
| 2003/0078592 A1 | 4/2003 | Heilman et al. |
| 2003/0100816 A1 | 5/2003 | Siess |
| 2003/0130668 A1 | 7/2003 | Nieman et al. |
| 2004/0002624 A1 | 1/2004 | Yu et al. |
| 2004/0002719 A1 | 1/2004 | Oz et al. |
| 2004/0059178 A1 | 3/2004 | McCarthy et al. |
| 2004/0162608 A1 | 8/2004 | Haverich |
| 2004/0171905 A1 | 9/2004 | Yu et al. |
| 2004/0193004 A1 | 9/2004 | Tsubouchi et al. |
| 2005/0033107 A1 | 2/2005 | Tsubouchi |
| 2005/0149093 A1 | 7/2005 | Pokorney |
| 2006/0036313 A1 | 2/2006 | Vassiliades |

* cited by examiner

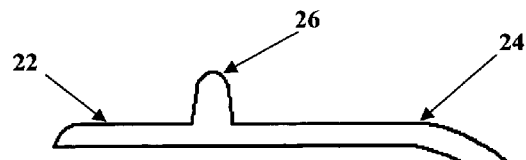
FIG. 3A
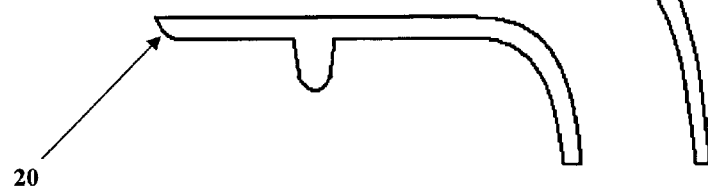
FIG. 3B
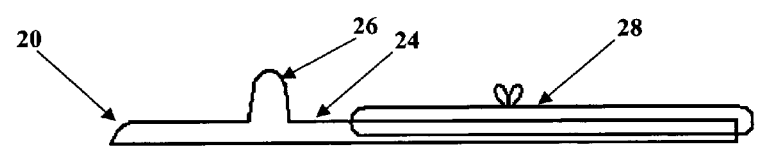
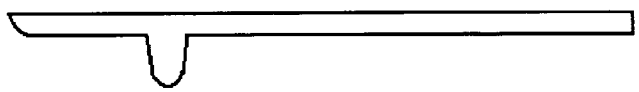
FIG. 3C
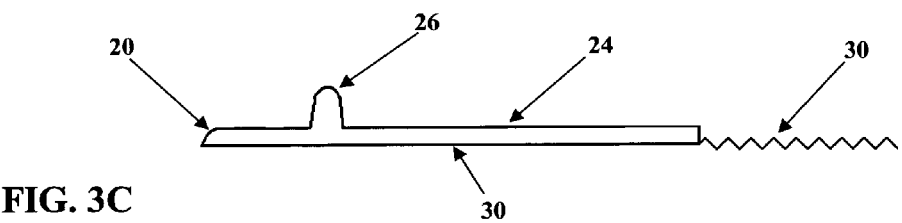
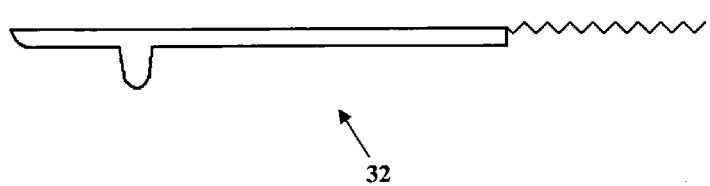

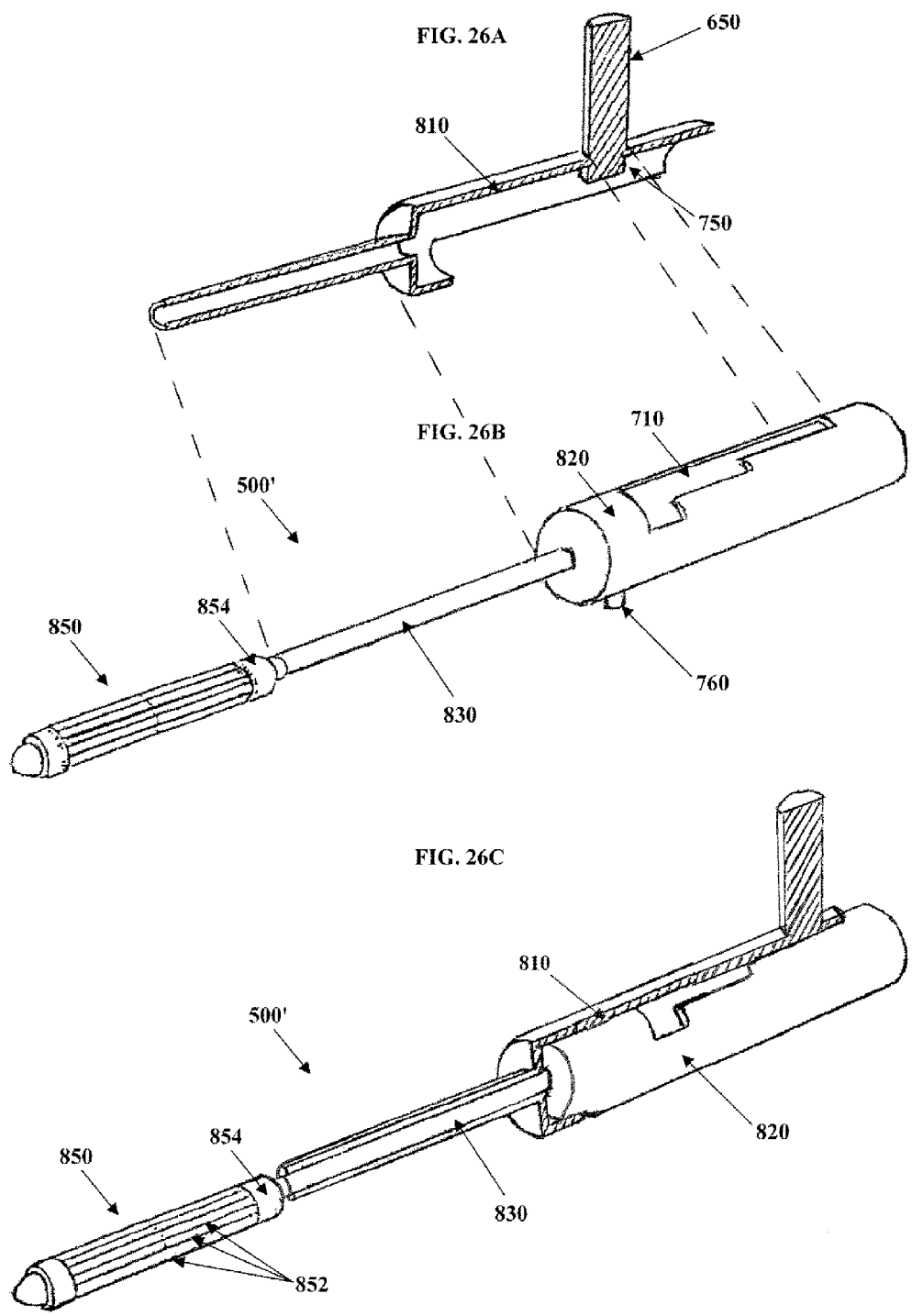

APPARATUS AND METHOD FOR CONNECTING A CONDUIT TO A HOLLOW ORGAN

RELATED APPLICATIONS

This application claims priority of U.S. Provisional Application Ser. Nos. 60/555,308, filed Mar. 23, 2004; 60/635,652 filed on Dec. 14, 2004 and 60/636,449 filed on Dec. 15, 2004.

BACKGROUND OF THE INVENTION

1. Field of the Invention

The present invention relates to an apparatus and method for connecting a conduit to a hollow organ, and more particularly, to a surgical device connectable to the apex of a heart.

2. Description of the Related Art

As the average age of the United States population increases, so do the instances of aortic stenosis. An alternative approach to the conventional surgical replacement of the stenotic aortic valve involves the use of an apicoaortic conduit. In this approach, the native aortic valve is not removed, and a prosthetic valve is implanted in a parallel flow arrangement. A connection conduit (or tube) connects the apex of the heart to the descending aorta. Somewhere along this conduit, the prosthetic valve is interposed. Thus, blood leaves the heart through the apex and travels through the conduit (with valve) to the descending aorta.

Until recently, surgical procedures to implant an apicoaortic conduit have included a single, long incision, such as in the $6^{th}$ intercostal space, to expose the heart and allow retraction of the lungs to expose the descending aorta. Recognizing the potential for broader scale use of the apicoaortic conduit for aortic valve replacement, some surgeons are now attempting to use smaller incisions and are requesting development of surgical tools for a minimally invasive procedure. As an initial attempt to make the procedure less invasive, some surgeons have recently performed the following procedure.

The patient is placed on the table in the supine position. Anesthesia is induced, and the patient is intubated with a double-lumen endotracheal tube, which facilitates one-lung ventilation and allows the surgeon to work within the left chest. The patient is positioned with the left side up (90 degrees). The pelvis is rotated about 45 degrees, such that the femoral vessels are accessible. An incision is made over the femoral vessels, and the common femoral artery and vein are dissected out. Heparin is administered. Pursestring sutures are placed in the femoral artery and vein. The artery is cannulated first, needle is inserted into the artery, and a guidewire is then inserted. Transesophageal echo is used to ascertain that the wire is in the descending aorta. Once this is confirmed, a Biomedicus arterial cannula is inserted over the wire, into the artery (Seldinger technique). The arterial cannula is typically 19 or 21 French. Once inserted, the pursestring sutures are snugged down over tourniquets. A similar procedure is followed for the femoral vein. The venous cannula is usually a few French larger than the arterial cannula. Once both vein and artery are cannulated, the cannulae are connected to the cardiopulmonary bypass, and the capability to initiate cardiopulmonary bypass at any time is present.

A 1 cm incision is made in approximately the $7^{th}$ interspace in the posterior axillary line; the videoscope (10 mm diameter) is inserted, and the left chest contents viewed. The location of the apex of the heart is determined, and the light from the scope used to transilluminate the chest wall; this allows precise localization of the incision. The incision is then performed; it is essentially an anterior thoracotomy, typically in the $6^{th}$ interspace. Recent incisions have been about 10 cm long, but are expected to become smaller and smaller with time. A retractor is inserted and the wound opened gently. A lung retractor is used to move the (deflated) left lung cephalad. The descending aorta is dissected free from surrounding soft tissue to prepare for the distal anastomosis. This dissection includes division of the inferior pulmonary ligament. A pledgeted suture is placed on the dome of the diaphragm and positioned to pull the diaphragm toward the feet (out of the way). The pericardium is incised about the apex of the heart, and the apex is freed up and clearly identified.

On the back table, the apicoaortic conduit is prepared: a 21 Freestyle® valve is sutured to an 18 mm Medtronic apical connector. The valve is also sutured to a 20 mm Hemashield graft. The Dacron associated with the apical connector is pre-clotted with thrombin and cryoprecipitate. The assembly is brought to the field, and a measurement made from the apex of the heart to the descending aorta. The assembly is trimmed appropriately. A partial-occluding clamp is then placed on the descending aorta, and the aorta opened with a knife and scissors. The conduit (the end with the 20 mm Hemashield graft) is then sutured to the descending aorta using 4-0 prolene suture, in a running fashion. Once this is complete, the clamp is removed and the anastomosis checked for hemostasis. Blood is contained by the presence of the Freestyle® aortic valve. The apical connector is placed on the apex, and a marker is used to trace the circular outline of the connector on the apex, in the planned location of insertion. Four large pledgeted sutures (mattress sutures) of 2-0 prolene are placed; one in each quadrant surrounding the marked circle. The sutures are then brought through the sewing ring of the apical connector. A stab wound is made in the apex in the center of the circle, and a tonsil clamp is used to poke a hole into the ventricle. To date, bypass has been initiated at this point, but doing so may not be necessary. A Foley catheter is inserted into the ventricle, and the balloon expanded. A cork borer is then used to cut out a plug from the apex. The connector is then parachuted down into position. A rotary motion is necessary to get the connector to seat in the hole. The four quadrant sutures are tied, and hemostasis is checked. If there is a concern regarding hemostasis, additional sutures are placed. The retractor is removed, chest tubes are placed, and the wound is closed.

Surgical tools developed specifically to implant the apicoaortic conduit are expected to provide the means for a much less invasive procedure. The procedure is expected to be performed with a series of smaller thoracotomy incisions between the ribs, such as immediately over the apex of the heart. In addition to avoiding the median sternotomy, development of appropriate surgical tools is expected to avoid the need for cardiopulmonary bypass, so that the procedure can be performed on a beating heart. The diseased aortic valve does not need to be exposed or excised. The stenotic aortic valve is left in place and continues to function at whatever level it remains capable of, and the apicoaortic conduit accommodates the balance of aortic output.

The major obstacle to widespread adoption of this superior technique is the nearly complete lack of efficient devices to perform the procedure. Surgeons wishing to adopt the procedure must gather a collection of instruments from a variety of manufacturers. Often these instruments were created for quite different purposes, and the surgeon is forced to adopt them as required and manually manipulate them during a procedure.

U.S. Published Patent Application 2003/0130668 A1 (Nieman) describes a method and apparatus for remotely cannulating a body part, such as a heart. The method and apparatus are endoscopic, i.e the instruments are mounted on the end of a long flexible member and inserted into the body through a trocar, i.e., a sharply pointed surgical instrument contained in a cannula. The endoscopic procedure is complicated. After the device is placed at or near the apex of the heart, the surgeon or some other controller performs at least 13 separate steps to secure the cannula in the heart wall. An attachment ring (which includes an apical ring and a locking stem) is sutured to the heart wall, and subsequently the cannula is connected to the attachment ring as a separate step. Because the procedure is endoscopic, imaging means (e.g., fluoroscopy) is used to place a balloon at the correct depth within the ventricle to provide occlusion.

The complex endoscopic procedure disclosed in Nieman appears to require that the cut tissue core be removed from the body prior to advancing the cannula to the heart wall. Further, Nieman appears to provide two mechanisms for placing the cannula in the heart wall. One such mechanism is to create a hole that is large enough to easily slide the cannula into the hole. This does not provide a tight fit between the cannula and cored heart wall to prevent blood loss from the cored heart wall and from the ventricle and relies entirely upon the sutured attachment ring to achieve hemostasis thus providing a period of time during which there could be great losses of blood. The second mechanism is to achieve a tight (interference) fit between the cannula and cored hole. However, such a tight fit requires substantial axial and torsional forces to be applied to the cannula. The flexible endoscopic instrument disclosed in Nieman cannot provide such forces to be transmitted U. S. Patent Publication No. 2004/0162608 (Haverich) discloses a method and apparatus for implanting a conduit into the wall of a heart. As illustrated in FIG. 8A, Haverich shows a conduit on a cutter that has a "corkscrew driver" with a coil. The corkscrew is rotated to cause the cutter to penetrate through the myocardium. However, substantial axial force is required to cleanly penetrate the myocardium, and such force is not easily applied by a corkscrew. Further, the pointed tip of the corkscrew can damage other areas of the heart wall (e.g., the septum) while applying axial force and rotation. Haverich discloses a balloon used for hemostasis. However, the balloon is a separate instrument that cannot be combined with the corkscrew.

U. S. Patent Publication No. 2002/0045846 (Kaplon) discloses a device similar to Haverich except that a trocar is used to penetrate the organ wall instead of a cutter with corkscrew. No tissue plug is formed with a trocar. Use of a trocar makes it difficult to achieve hemostasis during a procedure on a beating heart. To address this, rigid conduit 18 is inserted through the connector 16 after the connector is implanted with the trocar and sewn into place. Connector 16 does not appear to penetrate the heart wall. Connector 16 has a built-in valve to prevent blood loss after the trocar is removed and until conduit 18 is inserted

SUMMARY OF THE INVENTION

A connector conduit according to the preferred embodiment includes a rigid apical connector portion which will serve to provide egress from the left ventricle (such as from the apex or lateral wall), a flexible conduit portion which will carry blood from the connector to the arterial system (such as to the descending thoracic aorta or the ascending thoracic aorta), and the aortic valve itself, which will be situated somewhere within the conduit. The present invention primarily addresses implantation of an apical connector with an attached length of conduit, referred to herein as the connector conduit (or connector). The connector conduit is implanted using an applicator. Although this discussion focuses primarily on the apex of the left ventricle, it is understood that the present invention can be used to implant a connector conduit to any wall of the left ventricle or other hollow organ.

As described earlier, the surgeon conventionally uses a cork borer to cut a tissue plug from the ventricle wall. Once the tissue plug is removed, the surgeon must attempt to occlude the resulting hole, such as with a finger, a balloon or some other occlusion means, until the connector conduit is inserted. Despite attempts to occlude the resulting hole, substantial blood loss is inevitable. Cardiopulmonary bypass is used to reduce blood loss.

An object of the present invention is to integrate the cork borer and connector conduit to form a system in which the connector conduit is inserted into the ventricle wall as the tissue plug is being created, thereby eliminating the need for a separate occlusion means and greatly reducing blood loss. Such integration may be achieved by mounting the connector conduit directly onto the outer diameter of a coring element or integrating the cutter and the connector conduit, which cuts the tissue plug and occludes blood flow through the inner diameter. In this way, the cross sectional area for blood loss is reduced to the gap between the coring element and connector conduit.

Another object of the present invention is to combine the coring element with other features to form a complete applicator for securing the connector conduit into the ventricle wall. These features may include a mounting element and a handle element. The mounting element is an extension to the coring element that serves to add axial length to the coring element onto which the full length of the connector conduit may be mounted. The mounting element may be of the same diameter as the coring element. The handle element provides a grip to facilitate the necessary positioning, twisting and pushing force necessary to cut the tissue plug and to insert the connector into the ventricle wall. The handle could have a pistol handle shape, for example.

Another object of the present invention is to provide the option for additional features for the complete applicator system for securing the connector conduit into the ventricle wall, particularly at the apex. These additional features may include a retractor element and a quick connect coupling element.

The retractor element may have an expanding element for: 1) shaping the apex of the ventricle into a preferred shape for cutting the tissue plug, 2) providing a backing surface for the coring element in order to sandwich the heart wall between the coring element and expanding element, 3) pulling the tissue plug to within the coring element, and/or 4) ensuring that the tissue plug remains inside the coring element. The expanding element could be a liquid-inflated balloon, sponge, or a mechanically-operated umbrella, as examples.

The expanding element is mounted onto the retractor element, and the retractor element is slide-ably mounted within the coring element. A coupling element, such as a compression spring, provides the force to move the retractor element relative to the coring element. The retractor element may be designed to prevent relative rotation between the expanding element and coring element, thereby reducing the likelihood of damage to the expanding element. The retractor element may also include a section of increased diameter that abuts the outer heart wall to prevent premature or undesired cutting of the ventricle wall by preventing contact between the coring element and ventricle.

Another object of the present invention is to provide an expanding element that has a similar look and feel as the conventional procedure. For example, the expanding element may be a balloon. A syringe element may expand the expanding element to a predetermined level by inflation with a liquid. To minimize the space required for the syringe, the balloon may be designed specifically to require minimal inflation volume while still performing the necessary functions of the expanding element. In addition, a filling element of the applicator may provide the means to fill the syringe element and balloon from an external liquid source and to provide the means to purge air from the expanding element.

Another object of the present invention is to provide a connector conduit that has many of the features of the conventional apical connector (e.g., Medtronic™ apical connector) and includes additional features to make it compatible with the applicator and the surgical procedure. Additional features to make the connector conduit compatible with the applicator include 1) an ability to straighten the connector conduit from a bent configuration so that it will slide onto a straight mounting element, 2) a modified leading edge on the connector to ease insertion into the heart wall, and 3) a clamping element that includes portions of both the connector conduit and the applicator which serves to lock the connector conduit to the applicator in a predetermined position and to facilitate applying the twisting and pushing force necessary to insert the connector.

An additional feature of the connector conduit to make it compatible with the surgical procedure is a quick connect coupler to expedite attachment of the connector conduit to the remainder of the prosthesis, which includes the prosthetic valve. The quick connect coupler is necessary to prevent a long time delay between implanting the connector conduit into the ventricle and achieving blood flow through the complete prosthesis. Such quick connect coupler may consist of a first part that is attached to the connector conduit and a second part that is attached to the remainder of the prosthesis, which includes the prosthetic valve.

An additional feature of the connector conduit to make it compatible with the surgical procedure is to provide a length of conduit that may be collapsed, such as with an occlusion clamp, to prevent blood flow through the connector conduit before the quick connect coupler is connected and the surgeon is ready to allow blood flow through the complete prosthesis.

In one configuration of the invention, expansion of the expanding element and the position of the retractor element are controlled independently by the surgeon. For example, if the expanding element is a balloon connected to a syringe, the volume of liquid in the balloon is controlled by the position of the plunger inside the syringe. Similarly, a bolt may be used to control the position of the retractor element relative to the coring element. In this configuration, the surgeon must independently control the positions of the syringe plunger and the retractor element bolt.

Another configuration of the present invention provides a sequencing element (such as a cam mechanism) that ensures that critical steps of the procedure are performed in the proper sequence. The sequencing element synchronizes expansion of the expanding element with position of the retractor element. The sequencing element includes a sequencing bolt. The surgeon uses one hand to hold the applicator handle and the other hand to slide the sequencing bolt. In this way, independent control of the expanding and retractor elements is eliminated. Independent positions of these components are not user driven; rather, positions of these components are synchronized by the sequencing element. One example of a sequencing element is described next; however, it is understood that a sequencing element may be used to control fewer steps or additional steps of securing the connector conduit into the ventricle wall.

The system is set up with the connector conduit mounted onto the applicator and with the retractor fully extended. The procedure begins by making a small knife wound in the apex and pushing the retractor element (with fully-deflated expanding element) through the heart wall and into the ventricle. The surgeon slides the sequencing bolt from a first position to a second position. Once the sequencing bolt is in the second position, the surgeon may release the sequencing bolt. The sequencing element ensures that this sliding motion serves to first expand the expanding element and, after the expanding element is fully expanded, to release the retractor element so that the retractor element can move the expanding element relative to the coring element. The surgeon may now use the handle to apply twisting and pushing force to place the connector conduit into the ventricle wall. During this time, the sequencing element simultaneously coordinates:

a. application of compressive force between the expanding element and the coring element, thereby sandwiching and shaping the heart wall for cutting the tissue plug,
b. the coring element to cut a hole in the ventricle wall, thereby creating a tissue plug,
c. insertion of the connector conduit into the hole, and
d. the retractor element to retract the tissue plug from the hole into the coring element.

Once the tissue plug is created, the sequencing element partially reduces the diameter of the expanding element so that the expanding element can enter the inner diameter of the coring element while remaining of large enough diameter to prevent the tissue plug from sliding off of the retractor element. This change in diameter of the expanding element occurs automatically to a pre-set intermediate diameter without attention from the surgeon; Once the surgeon has placed the connector conduit at the desired position within the ventricle wall, the applicator may be removed.

In a preferred configuration, the connector conduit is a fabric (e.g., Dacron) covered device that is specifically designed for insertion into the wall of the left ventricle, such as at the apex. It contains a structural frame, a sewing flange (or suture ring) for attachment to the heart, and a standard fabric (e.g., Dacron) flexible vascular graft that extends through the lumen of the entire length of the structural frame and for some additional length beyond. An outer fabric may also cover the outside of the structural frame. The components of the connector conduit are interconnected, such as with polyester thread. The fabric may include orientation marks, such as a line along the length of the conduit. In addition, a quick connect coupling may be used to attach the connector conduit to the remainder of the prosthesis, which includes the prosthetic valve or ventricular assist device, as examples.

A function of the structural frame is to provide mechanical integrity, i.e., rigidity, for the connector conduit. The structural frame may include a leading edge, a cage, a bend, and a holder. The leading edge is the first portion of the structural frame to be pushed through the heart wall. To minimize effort needed to push the connector through the heart wall, such leading edge may be tapered and/or beveled, for example. The cage is the portion of the structural frame that resides within the heart wall. The bend is the portion of the structural frame that holds the conduit in a preferred shape to direct blood flow from the left ventricle to the aorta, as described next in more detail. The holder is the portion of the structural frame that provides a means of mechanical connection between the connector conduit and applicator.

The bend in the structural frame may be any appropriate angle (such as 90 degrees) to properly direct the conduit from the ventricle to the portion of the aorta where the conduit is to be connected. For example, the bend in the structural frame may be around 90 degrees if the conduit is to be connected to the descending thoracic aorta, or a larger angle bend may be used if the conduit is to be connected to the ascending thoracic aorta, for example. As described next, such bend may be flexible or rigid.

In one embodiment, the bend of the structural frame may be flexible. For example, a set of equally-spaced circular rings mounted perpendicularly on a spine could form a bend that can flex to a range of angles. The circular rings provide radial support to prevent collapse of the conduit due to external forces. The spine may be at the outer radius of the bend or at the inner radius of the bend, as examples. In this embodiment, the bend can be straightened out from a preferred angle such that a mounting element of the applicator may be inserted straight through the lumen of the connector. Upon removal of the mounting element, if the bend is constructed of a material with a relatively high modulus of elasticity (e.g., PEEK), the connector returns to its bent configuration. If the bend is constructed of a material with a relatively low modulus of elasticity (e.g., polypropylene, polyethylene), the connector forms the bent configuration only when an external force is applied, such as by a bending means. Such bending means could involve pulling on threads that are weaved through the circular rings so that the bend is formed when the threads are pulled, for example. When the bend is at the preferred angle, the user may tie or crimp the threads together, for example, thereby preventing straightening of the bend. Such bending means allows the user to select any one of a plurality of possible bend angles as the preferred angle. Such bending means may also be used with a bend constructed of a material with a relatively high modulus of elasticity, such as to prevent straightening beyond the preferred angle.

In another embodiment, the bend of the structural frame may be rigid. In this embodiment, since the bend cannot be straightened out, the bend must include a port such that the mounting element of the applicator may be inserted through such port and through the lumen of the cage. In this embodiment, the conduit must include a branch of additional conduit to form a Y. Such additional branch of conduit is coaxial with the cage for mounting the connector conduit onto the applicator. Once the connector conduit is implanted into the heart wall and the applicator is removed, the branch of conduit is occluded, such as by sewing or stapling the conduit closed, for example. The branch is then removed, such as by cutting with scissors.

In another embodiment of the connector conduit, a quick connect coupler may be used to attach the connector conduit to the remainder of the prosthesis, which includes the prosthetic valve. The complete prosthesis may be divided into two parts: a first part that includes the prosthetic valve with lengths of conduit attached to both the upstream and downstream sides of the prosthetic valve and a second part that includes the connector conduit. The quick connect coupler allows the surgeon to rapidly connect said first part to said second part. In this way, the surgical procedure may be performed by first attaching said first part of the complete prosthesis to the aorta. Then, after the connector conduit is secured into the ventricle wall, the quick connect coupler allows rapid completion of the flow circuit to minimize the time between insulting the heart by cutting the hole and reducing the work load on the heart by allowing blood flow through the prosthesis.

An applicator is used to implant the connector conduit into the ventricle wall. In a preferred embodiment, the applicator provides mechanical support on the surfaces of both the inner diameter and the outer diameter for some portion of the fabric-covered structural frame. Such support may be necessary to avoid unwanted distortion or movement of the structural frame while the connector conduit is being implanted through the heart wall. For example, the mounting element of the applicator, which is inserted straight through the lumen of the connector, may provide mechanical support (such as radial support) on the inner-diameter surface to reduce distortion of the structural frame during implantation. On the outer-diameter surface, the applicator may include a concentric tubular structure, referred to as the pushing element. The pushing element provides mechanical support (such as radial support) on the outer-diameter surface of the structural frame to reduce distortion during implantation. In a preferred embodiment, the mounting element and the pushing element are rigidly connected.

In a related embodiment, an indexing means provides an interface between the pushing element and connector conduit that may prevent or greatly reduce rotation and/or axial movement of the connector conduit relative to the pushing element. As such, rotary or axial force applied to the pushing element is transmitted to the connector conduit through the locking means. An effective locking means may incorporate portions of the pushing element, mounting element and connector conduit. For example, the indexing means may include a slot-and-key arrangement that 1) positions the connector conduit at a preferred angle relative to the pushing element thereby orienting the bend in the structural frame, 2) prevents axial and rotary motion of the connector conduit relative to the pushing element, and 3) allows the connector conduit to be easy mounted onto and released from the applicator. Such indexing means may include a pushing element with an adjustable diameter that allows both rigid mounting and unhindered release of the connector conduit. Such indexing means may also include a connector conduit with a holder that locks to the pushing element, such as with a slot-and-key arrangement and/or with a tight friction fit, as examples. Such holder may be sandwiched firmly between the mounting element and pushing element.

In a preferred configuration, the mounting element extends from a coring element that shares the same axis and has the same outer diameter as the mounting element. The coring element is used to cut a hole into the heart wall. Such coring element could consist of a thin-walled tube, the leading edge of which has been sharpened or serrated. The inner diameter of the connector conduit could fit snugly on the outer diameter of the coring element and mounting element. In use, the coring element could produce a hole in the heart wall that is smaller than the outer diameter of the connector conduit, thereby producing a snug fit.

In a related embodiment, a handle may be rigidly attached to the pushing element. The handle may be at a substantially right angle after the manner of a pistol grip, for example. Such a handle attachment provides a more effective method of applying the insertion force and back-and-forth rotation needed to implant the connector conduit.

In a preferred configuration, located concentrically within the mounting element is a retractor element consisting of a generally tubular structure having a pointed end that is inserted through the left ventricle wall. The tubular structure could be rigid. In a preferred embodiment, the pointed end of the retractor element could be a blunted point. In this way, after a small knife wound is made in the epicardium (outer surface of the heart), the blunted point could enter the knife wound and divide muscle fibers to penetrate the myocardium and left ventricle chamber. A purpose of the blunted point is to reduce the likelihood of damage should the point unintentionally contact other areas of the inner wall during use. In an alternative embodiment, the retractor element could include a very sharp pointed end being capable of producing its own entrance hole into the wall of the heart. Alternately, it could have a blunted point that would simply follow a previously created hole through the entire thickness of the ventricle wall. If so desired, the tubular structure of the retractor allows use of a guide-wire to follow a previously created hole.

Near the pointed end of the retractor element is an expanding element, such as an inflatable balloon, an unfolding umbrella-like construction, an expandable collar, or similar structure. Once inside the ventricle, the expanding element is expanded from an initial diameter that may approximate the outer diameter of the retractor element to a second diameter. In a preferred configuration, the expanding element expands to a second diameter that is larger than the outer diameter of the coring element. The expanding element expanded to its second diameter seats snugly against the inside wall of the ventricle. Functions of the expanding element may include 1) expanding symmetrically to shape the inner wall of the ventricle into a preferred shape for cutting the tissue plug, and 2) fully retracting to within the coring element while remaining at least partially expanded.

A first function of the expanding element is symmetric expansion, which provides at least two benefits. The first benefit is related to the variable, cone-shaped geometry of the left ventricular chamber near the apex. Symmetric expansion of the expanding element to a diameter that is larger than the outer diameter of the coring element effectively flattens out the ventricle wall in the vicinity of the apex so that the ventricle wall is more perpendicular to the sharpened leading edge of the coring element, thereby allowing the coring element to cut through the entire thickness of the ventricle wall. The tubular structure of the retractor element must resist the radial reaction forces from the ventricle walls. The second benefit of symmetric expansion is to ensure contact between the expanding element and the leading edge of the coring element along its entire circumference as the tissue plug is formed. Asymmetric expansion of the expanding element can result in formation of a plug with hanging attachments to the left ventricle wall.

A second function of the expanding element is to fully retract and retain the plug within the coring element after the plug is cut. Such full retraction ensures that the applicator will slide out of the connector conduit (after the connector is implanted) without the plug and expanding element coming into contact with the inner diameter of the connector conduit. Such contact could increase the force required to remove the applicator from the connector conduit and could possibly result in debris from the removed plug being deposited on the inner diameter of the connector conduit. In addition, the expanding element must remain at a large-enough diameter after being retracted to within the coring element to ensure that the plug cannot slide off the end of the retractor element.

In a related embodiment, this second function could include a coupling element that forces the retractor element to retract within the mounting element. In a preferred configuration, the coupling element could be a compression spring, for example. In this configuration, the retractor element could be slide-ably connected to the mounting element by means of the compression spring. The force produced by the compression spring tends to pull the expanding element snugly against the inside wall of the ventricle and to pull the tissue plug into the coring element after the tissue plug is detached from the ventricle. Alternatively, the user could manually provide the necessary force to retract the retractor element to within the coring element.

In a preferred embodiment, the expanding element can be: 1) initially at a first diameter that approximates the outer diameter of the retractor element, 2) expanded to a second diameter that is larger than the outside diameter of the coring element, and 3) then reduced to a third diameter that is smaller than the inside diameter of the coring element but larger than the outer diameter of the retractor element. Inflation to the second diameter accommodates the first function of the expanding element (described above), and reducing to the third diameter accommodates the second function of the expanding element (described above).

In a preferred embodiment, the expanding element is a balloon. The balloon may be inflated using an access means, such as a plunger in cylinder configuration (like a syringe) connected to the balloon by a flow passage, such as a channel integrated into the retractor element. An appropriate fluid to inflate the balloon could be saline, for example. The balloon material should be selected to best perform the functions of the expanding element. Polyurethane is a preferred material. Polyurethane is an elastic material that allows a balloon to be expanded symmetrically to as much as twice the original volume using a hand-held syringe. Such balloons are strong, abrasion resistant, and durable. Use of latex, another elastic material, is less desirable. Latex balloons typically expand asymmetrically, so use of a latex balloon as the expanding element could necessitate a means integrated into the balloon to ensure symmetric expansion. In the present invention, a latex balloon could be inflated to a symmetric diameter as determined by tension rods or sutures, for example, attached to the balloon and the retractor element. Once the tissue plug is formed, the plunger could be displaced to reduce the size of the balloon to allow retraction into the coring element. A means to prevent damage to the latex balloon by the coring element may be used. Alternatively, the balloon may be constructed of polyethylene terephthalate (PET; trade names include Dacron and Mylar), which is a non-elastic material. Balloons made of PET may be symmetrically inflated to higher pressures without appreciable change in the balloon volume.

In one configuration of the present invention, expansion of the expanding element and the position of the retractor element are controlled independently by the surgeon. Consider the example of using a balloon as the expanding element. Inflation of such balloon could be fully controlled by the surgeon, such as by using a finger to displace a plunger inside a cylinder. In such case, the surgeon could inflate the balloon to any volume up to the maximum volume of the plunger/cylinder. Also in this configuration, the position of the slideable retractor element relative to the coring element may be independently controlled by means of a bolt attached to the retractor element that passes through an indexed slot in the mounting element. In a preferred embodiment with the mounting element rigidly connected to a pushing element, the indexed slot could be in such pushing element. As the bolt is moved from one indexed position in the slot to another, the retractor is advanced or retracted relative to the coring element. In a preferred configuration with compression spring coupling between the retractor element and coring element, an indexed slot with the retractor element fully advanced (ready for insertion into the left ventricle wall) could be used. The bolt could then be manually released from the indexed slot after inflating a balloon on the retractor element. The compression spring would then pull the balloon firmly against the inner heart wall, thereby sandwiching the heart wall between the balloon and coring element.

Independent control of the expanding element and retractor element could require increased surgeon training to ensure operation of these elements in the proper sequence. Alternatively, various latching or locking means could be used. For example, once the balloon has been inflated to a preset maximum volume, a latching means could lock the plunger into place, thereby preventing unintentional deflation of the balloon. If necessary, deflation to an appropriate volume for retraction into the coring element could be automatically triggered when the retractor element reaches a preset position during retraction. Alternatively, inflation and deflation of such balloon to preset maximum and reduced volumes could occur automatically, such sequence being initiated by pressing a spring-loaded trigger that displaces the plunger, for example. In addition, a safety latch or other means could prevent manual release of the bolt until the expanding element is fully expanded. These separate latching or locking means could result in a complicated mechanical configuration.

In a preferred configuration of the present invention, a sequencing element, such as a cam mechanism, is used to coordinate expansion of the expanding element with position of the retractor element. Control of the expanding element and control of the retractor element position are coordinated so that the surgeon need only move a single sequencing bolt to control both the expanding element and the retractor element. The specific actions of the expansion element and retractor element that are controlled by the sequencing element may be chosen by the device designer to best accommodate the degree of control preferred by surgeons.

In one embodiment of a preferred configuration that includes a sequencing element, the cylinder used to inflate/deflate the balloon (the syringe cylinder) may be integrated into the retractor element. Thus, the syringe cylinder, retractor element, balloon, and flow passage connecting the syringe cylinder to the balloon are integrated into a single component, referred to as the retractor assembly. The plunger used to inflate/deflate the balloon (the syringe plunger) may include a sequencing bolt extending radially from the plunger axis. Such sequencing bolt also extends radially through a slot in the syringe cylinder. As such, the slot in the syringe cylinder limits axial movement of the plunger in the syringe cylinder. By having a plurality of circumferentially interconnected slots of various axial lengths in the syringe cylinder, the degree of balloon inflation may be controlled by moving the sequencing bolt to a preferred axial slot. Synchronization of balloon inflation/deflation with motion of the retractor assembly relative to the pushing element (which is rigidly connected to the mounting element) may be achieved with two cam slots in the pushing element, for example. The first cam slot controls motion of a cam follower rigidly attached to the retractor assembly, thereby controlling the position of the retractor assembly relative to the pushing element. The second cam slot synchronizes inflation/deflation of the balloon relative to the position of the retractor assembly within the pushing element. The sequencing bolt serves as the cam follower in the second cam slot. Safety features may be integrated into the design of the cam mechanism. For example, the cam and follower can be designed to prevent movement of the retractor assembly relative to the pushing element (which is rigidly connected to the coring element) until the balloon is fully inflated.

Various other features may be included to ensure safety and proper use of the connector conduit with applicator. For example, a port with a two-way valve may be integrated into the plunger/cylinder with balloon system to allow for filling with fluid and removal of air. As another example, a mounting tool may be used to mount the connector conduit over the coring element without damage to the fabric. As another example, a folding tool may be used to squeeze fluid from the balloon and to fold the balloon for use. As another example, the mounting tool and folding tool may be integrated into a single tool.

The invention facilitates procedures using an integral device in which the various steps are preformed in a coordinated, i.e. sequenced manner. This renders the procedure simple and safe and reduces the likelihood of tissue damage or other complications. Other features and advantages of the invention will be apparent from the detailed description and from the claims.

DETAILED DESCRIPTION OF THE PREFERRED EMBODIMENTS

Figure 1:
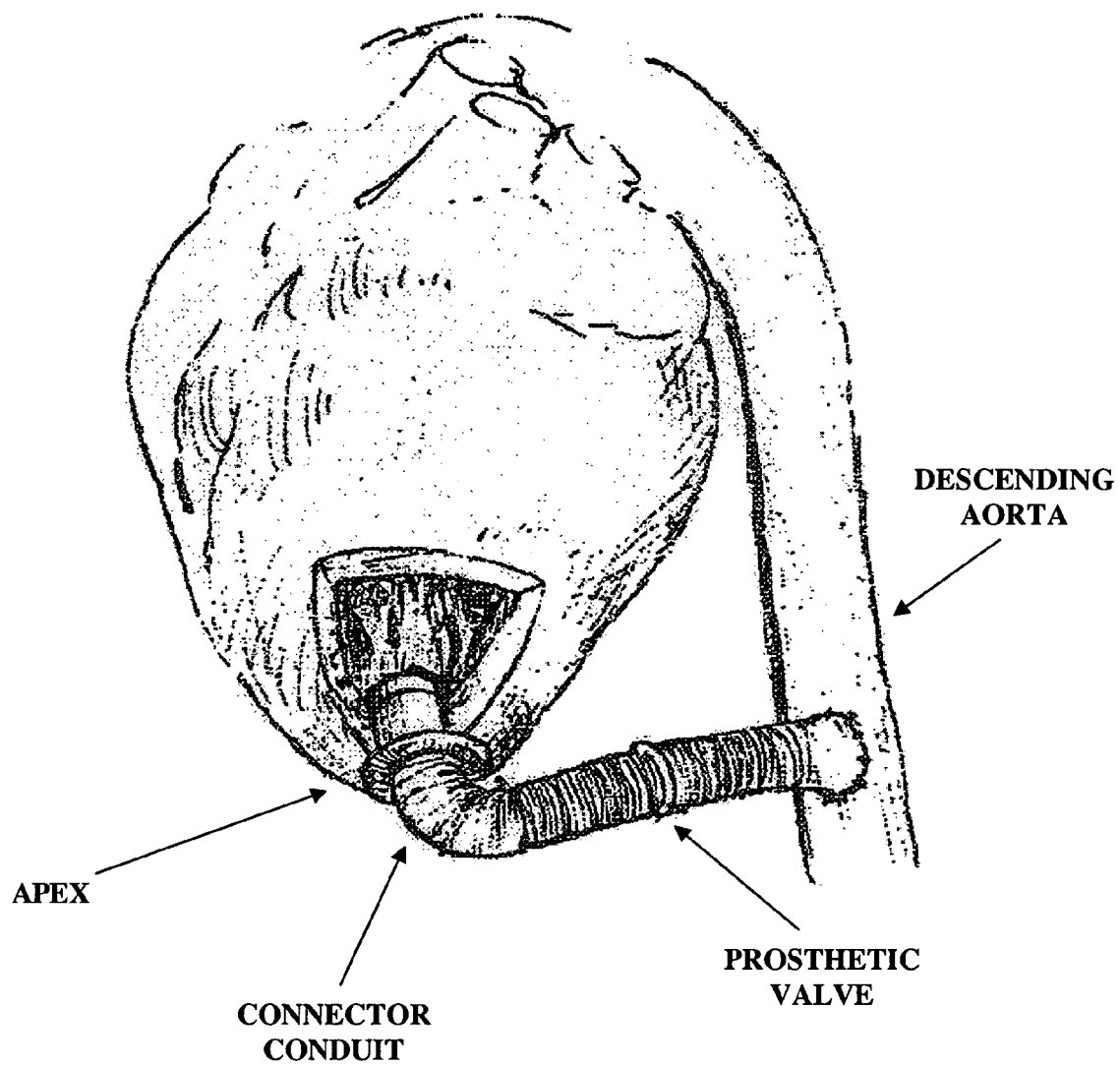
FIG. 1 illustrates an apicoaortic conduit.

FIG. 1 is an illustration of an apicoaortic conduit, which extends from the apex of the left ventricle to the descending aorta with a prosthetic valve positioned within the conduit. The preferred embodiment of the present invention includes aspects of the connector conduit and an applicator used to implant the connector conduit.

The connector-conduit with applicator of the present invention is best described as consisting of five major parts: a connector-conduit, a retractor, hole forming device such as a coring element, a pushing component, and a handle. A fabric material pleated conduit of a type common and well known in the field is permanently fixed to the inner surface of a rigid connector to form the connector-conduit. The conduit extends from the forward edge of the connector and continues beyond the connector, as a flexible portion, for some distance.

The connector-conduit includes a rigid portion defined by an internal support structure made of a suitably flexible material that is preferentially biased to assume a bent configuration (such as a right angle) upon removal of restraining forces. In one embodiment, the connector internal support structure is covered with fabric, such as knitted or woven Dacron, for example. A suturing ring is integrated into the covering fabric and provides a suitable flange for suturing the connector to the surface of the heart. The leading edge of the connector is tapered to facilitate insertion of the connector-conduit component. The "rigid" portion is rigid enough to facilitate insertion as described below and to maintain the hole in an open position. However, the rigid portion can be flexible. Accordingly, the term "rigid" as defined herein means relatively rigid and can include flexibility.

Figure 10A:
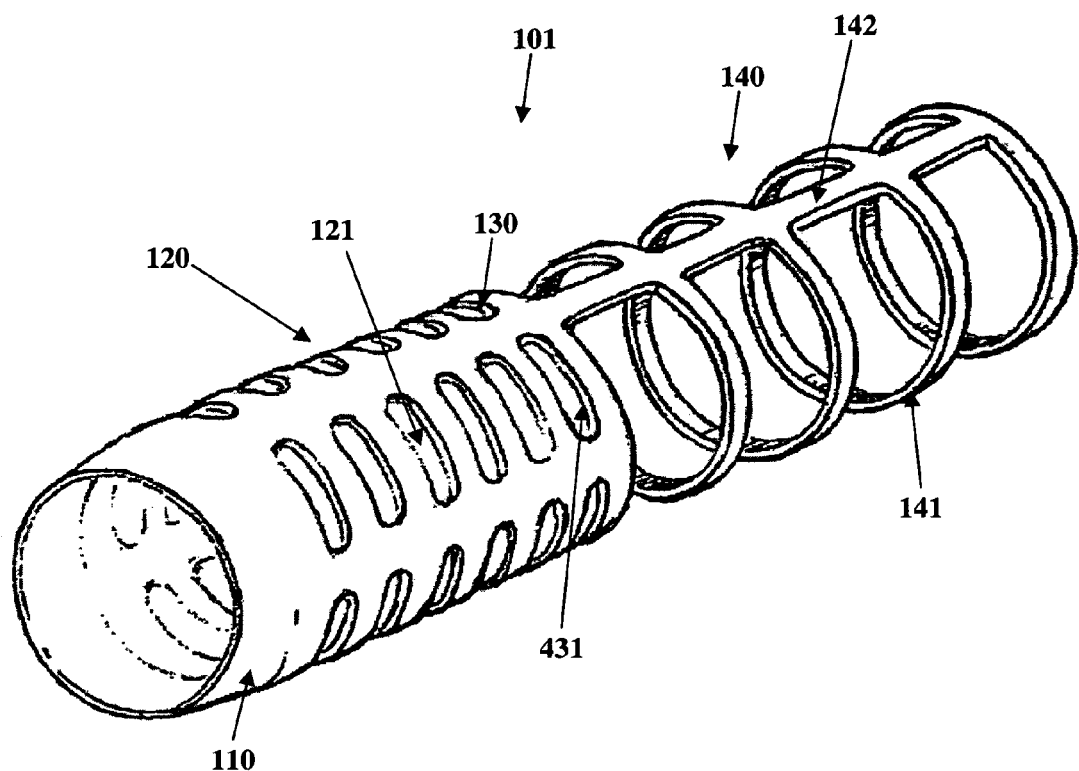
FIG. 10A is a perspective view of a flexible structural frame of another embodiment of the connector conduit shown in a straight configuration.

As shown in FIG. 10A, the structural frame 101 of the connector-conduit is a series of circular rings 141 joined to a curved spine 142. During implantation, the curved spine 142 is straightened, as shown in FIG. 10A, resulting in a straight pathway for the passage of instruments. As an alternative, the connector-conduit could include circular rings 141 without curved spine 142. As such, the circular rings would prevent collapse of the conduit, but the curved conduit would be formed manually after implantation, rather than by being formed by the curved spine 142. As another alternative, a modified coil spring in the shape of a curve could be used instead of circular rings 141 and curved spine 142. Properties of the coil spring would be chosen to prevent radial collapse and to provide appropriate stiffness of the curved position.

The leading edge of structural frame 101 is a taper 110 which allows for easy insertion of the connector through the ventricle wall. The material of the structural frame 101 could be a shape memory alloy (e.g., Nitinol), plastic, or other similar biocompatible material.

Figure 2A:
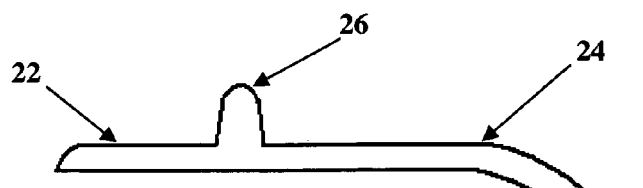
FIG. 2A is a cross-sectional view of an embodiment of the structural frame of the connector, covered in fabric, with an incorporated sewing flange and shown in the bent configuration.

FIG. 2A illustrates a fabric covering 24 over the outside surface of structural frame 101. Because connector surface 22 is in contact with the myocardial hole after implantation, a suturing ring or flange 26 is incorporated into the fabric covering 24 to provide an attachment site for sutures to anchor the connector to the heart. The fabric covered suture ring 26 could be made of a biocompatible foam or rubber.

Figure 2B:
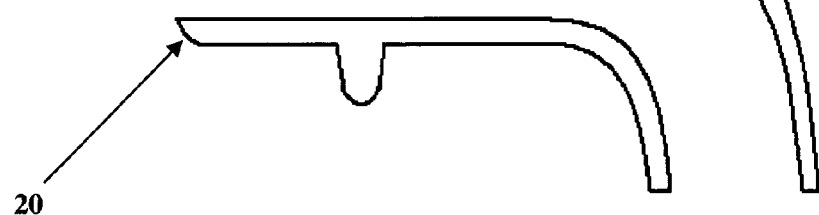
FIG. 2B is a cross-sectional view of the structural frame of the connector of FIG. 2A shown in a straight configuration.

FIG. 2B shows the fabric covered structural frame 101 and suturing flange 26 in a straightened position. The straightened position can be achieved by, for example, inserting a straight instrument through the lumen of the frame. Alternately, the structure can be held in the open position through the use of stay stitches 28, or the like, placed such that the circular rings 141 are held in close proximity.

Figure 2C:
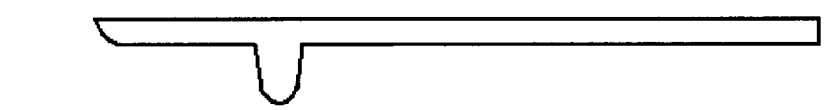
FIG. 2C is a cross-sectional view of the connector of FIG. 2A shown in the straight configuration, and with a fabric conduit in place.
Figure 2C:
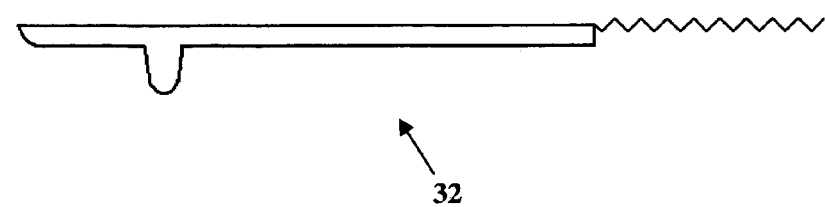

FIG. 2C is a view similar to FIG. 2B, showing the structural frame in the straightened position with a pleated fabric conduit 30. Conduit 30 extends from taper 20 of the structural frame 101, through the length of the structural frame 101, and for some additional length beyond the structural frame 101 to define a flexible portion of the connector conduit. An orientation marker (not shown) on connector surface 22, for example, is used to identify the direction that conduit 30 will be oriented once implanted into the heart. The orientation marker is visible at all times to assist the surgeon while placing the connector-conduit 32 into the connector-conduit applicator and to facilitate implantation at an appropriate angle into the heart. Also, a radiopaque marker(s) (not shown) may be integrated into the entire length of fabric covering 24 and conduit 30 to facilitate identification and location of the structure by X-ray or other means.

Figure 3:
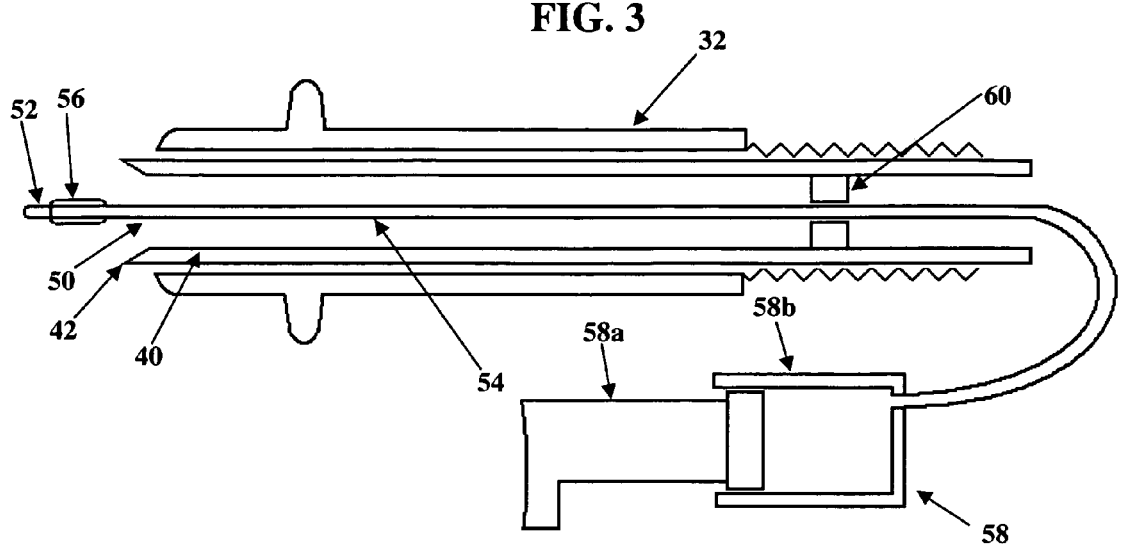
FIG. 3 is a cross-sectional view of an embodiment of the device showing the coring element and the retractor element in place within the straightened connector.

Referring to FIG. 3, in accordance with another embodiment of the present invention, a hole forming device such as coring element 40, is placed concentrically within the lumen of the connector-conduit 32. The coring element 40 preferably consists of a tubular structure, which could be made entirely of metal (such as stainless steel) or primarily of a plastic material with a metal insert for the leading edge 42. In a preferred configuration, the leading edge 42 of coring element 40 may be suitably sharpened such that it cuts a plug of tissue of approximately the same diameter as the outer diameter of the coring element 40. Note that the hole forming device can be any known mechanism for forming a hole, such as a laser cutter, a thermal ablation device, a chemical ablation device, or the like.

An interference fit between connector surface 22 and the hole created by the coring element 40 is necessary to reduce bleeding from the cut myocardial surface and to reduce blood leakage from the left ventricle. The amount of such interference fit is the difference between the diameters of the hole created by the coring element 40 and the outer surface of the connector 22.

In a preferred embodiment of the device, the coring element 40 has an outer diameter that closely matches the inner diameter of the connector-conduit 32. Such construction allows removal of the coring element 40 through the connector-conduit 32 while presenting only a small blood pathway between these two elements. Such construction is intended to minimize blood loss from the left ventricle when the coring element 40 has completed its cut.

FIG. 3 further illustrates the concentric placement of the retractor element 50 within the coring element 40. Retractor element 50 includes a blunt tip 52, a tubular body 54, an expanding element 56, such as a balloon, and an access means 58 for engageably expanding element 56. Access means 58 can be a plunger 58*a* in a cylinder 58*b* configuration, whereby displacement of the plunger expands or contracts expanding element 56. A centering plug 60 is shown concentrically positioned within and rigidly attached to coring element 40. The centering plug 60 concentrically positions retractor element 50, which slideably moves within the centering plug 60. The centering plug 60 also presents a barrier to the flow of blood through coring element 40, once the tissue plug is formed. Proper placement of centering plug 60 within coring element 40 should consider tradeoffs between two different parameters. First, centering plug 60 should be placed at a position within coring element 40, which allows ample space for the expanding element 56 and the tissue plug. Second, since radial force from the heart wall tends to deflect the expanding element 56, retractor element 50 must have a sufficient stiffness to substantially resist such deflection. Such deflection may also be reduced by limiting the axial distance between the expanding element 56 and centering plug 60.

Figure 4:
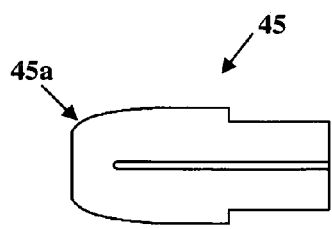
FIG. 4 is a cross-sectional view of a cylinder plug tool that slides over the retractor element and into the coring element, which is used to load the connector-conduit onto the coring element.

FIG. 4 shows a cylinder plug tool 45 for insertion into coring element 40 prior to loading connector-conduit 32 onto coring element 40. Cylinder plug tool 45 facilitates loading connector-conduit 32 without damage from leading edge 42 of coring element 40. Once the connector-conduit 32 is loaded, cylinder plug tool 45 is removed and placed aside. As a safety measure, cylinder plug tool 45 has an extended length with a tapered blunted end 45*a*, which extends to cover retractor element 50, preventing insertion of the retractor element 50 into the left ventricle before cylinder plug 45 is removed.

Figure 5:
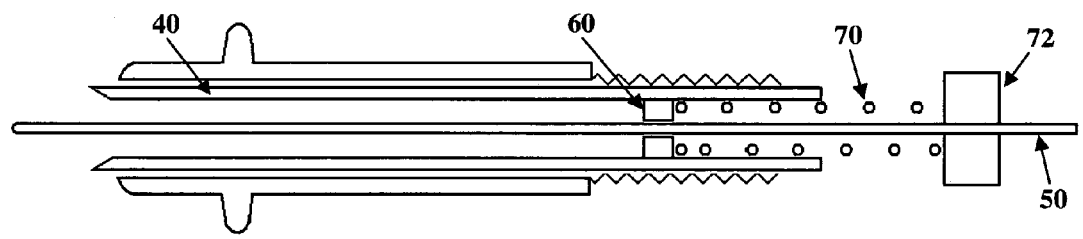
FIG. 5 is a cross-sectional view of an embodiment of the device showing the placement of a compression spring between the retractor element and the coring element.

Referring to FIG. 5, another embodiment of the present invention shows a compression spring 70 placed around the retractor element 50. One end of the compression spring 70 seats on the centering plug 60, and the other end seats on a sliding plug 72. Sliding plug 72 is rigidly connected to retractor element 50. Spring 70 ensures that expanding element 56 seats snugly against the inside wall of the ventricle to symmetrically displace the ventricle wall from the path of the coring element. Once the tissue plug is cut from the ventricle by coring element 40, spring 70 also pulls the tissue plug fully within the coring element 40.

Figure 6:
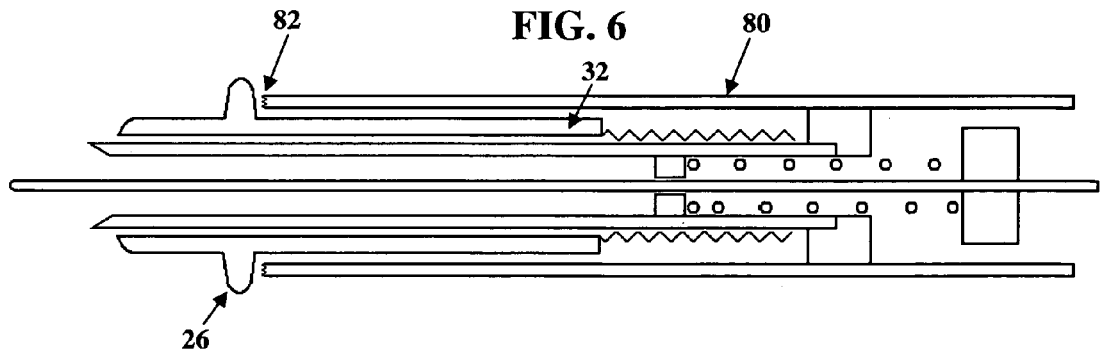
FIG. 6 is a cross-sectional view of another embodiment of the device showing the placement of a pushing element.

FIG. 6 illustrates a further embodiment, wherein a cylinder-shaped pushing element 80 is positioned concentrically outside the connector-conduit element 32. Pushing element 80 is used to apply force to the coring element 40 and connector-conduit element 32. This force is required for the coring element 40 to cut the hole in the myocardium and for pushing the connector-conduit element 32 into the hole. The end of the pushing element 80 that is in contact with the suture ring 26 has a roughened surface 82 intended to prevent relative rotary motion between the suture ring 26 and pushing element 80. As such, the pushing element 80 allows both a force and a back-and-forth rotary motion to simultaneously be applied to the coring element 40 and connector-conduit element 32, as required to fully seat the suture ring 26 flush with the surface of the heart. Pushing element 80 could be made of metal, plastic or other suitable material.

Figure 7A:
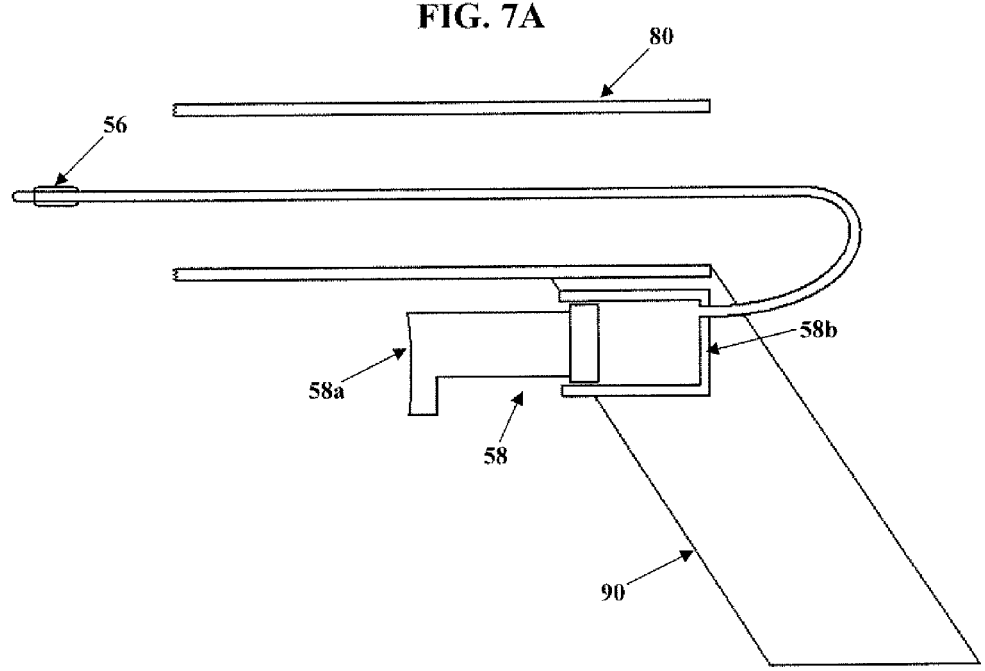
FIG. 7A is a cross-sectional view of yet another embodiment of the device showing the attachment of a handle to the pushing element with an access means for the expandable element integrated into the pushing element, wherein the expandable element is shown contracted.
Figure 7B:
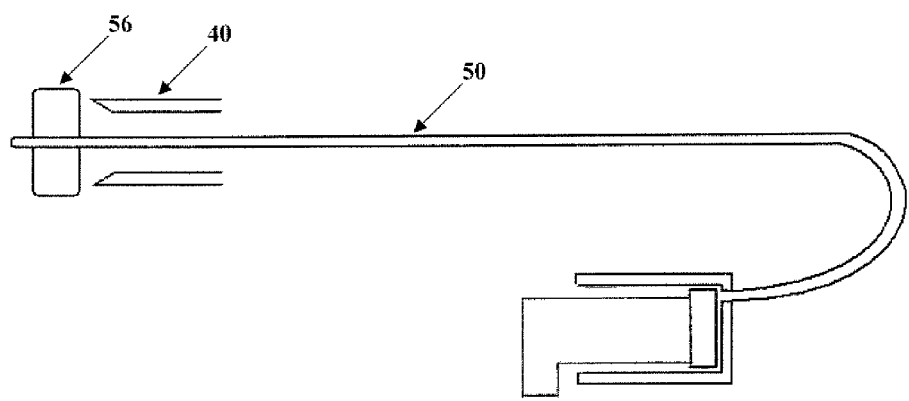
FIG. 7B shows the embodiment of FIG. 7A with the expandable element expanded.

Referring to FIGS. 7A and 7B, a handle 90 is rigidly attached to pushing element 80. As shown, handle 90 is configured similar to a pistol grip, for example, handle 90 having an angle of about 70 degrees, with the pushing element 80. Handle 90 provides a user-friendly interface for the surgeon to hold with one hand, to position the coring element 40, to apply axial force to the connector-conduit element and to provide a back-and-forth rotational motion of around 90 degrees. Of course, many alternatives exist for the user interface. For example, the pushing element 80 itself could be used as the handle. As another example, a handle could form a "T" shape on the end of the pushing element 80.

Also shown in FIG. 7A, an access means 58 is used to expand or contract expanding element 56. Access means 58, for example, can be a trigger-type mechanism integrated into handle 90. As such, the user can use a finger to pull plunger 58*a* into the cylinder 58*b*, thereby displacing the fluid (such as saline) inside the cylinder 58*b* into the balloon 56. FIG. 7B shows the inflation of the balloon 56. As a safety feature, the plunger can have a latching device (not shown) that latches the plunger 58*a* with the balloon fully inflated, thereby preventing deflation of the balloon before intended.

Figure 8:
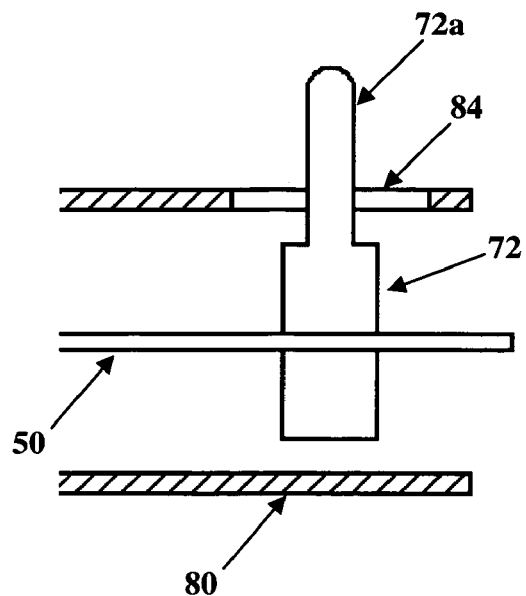
FIG. 8 is a cross-sectional view of an embodiment of the device showing the inclusion of a sliding bolt on the retractor element and related indexed slots on the pushing device.
Figure 9:
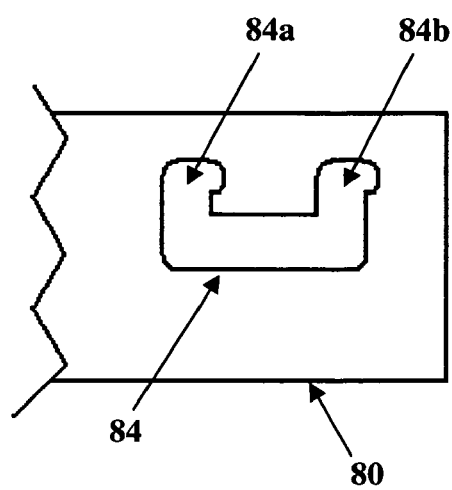
FIG. 9 is a partial view the pushing element of FIG. 8 showing the indexed slots on the pushing device.
Figure 8A:
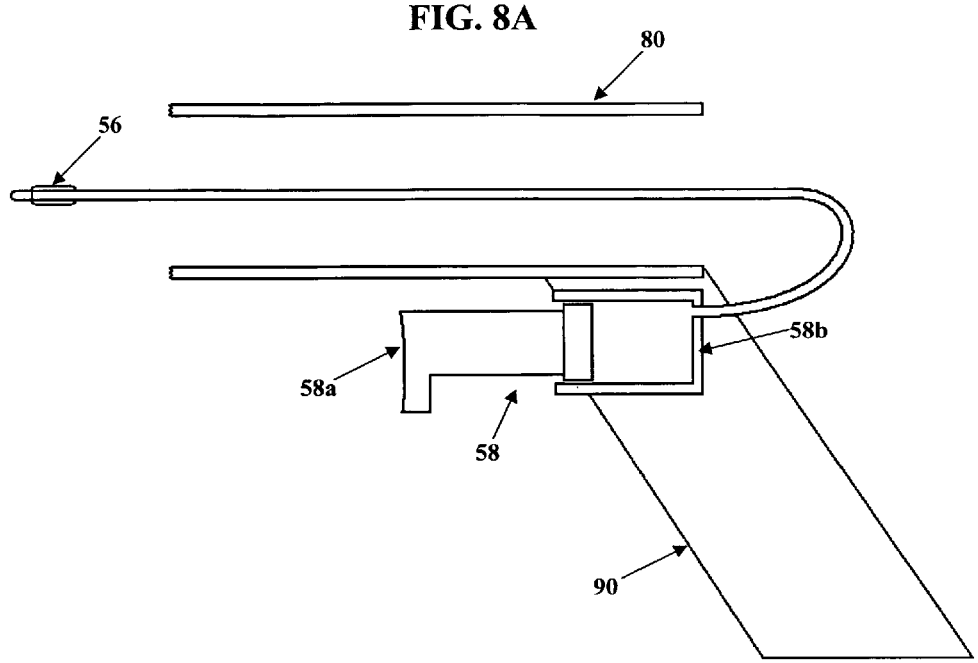
Figure 8B:
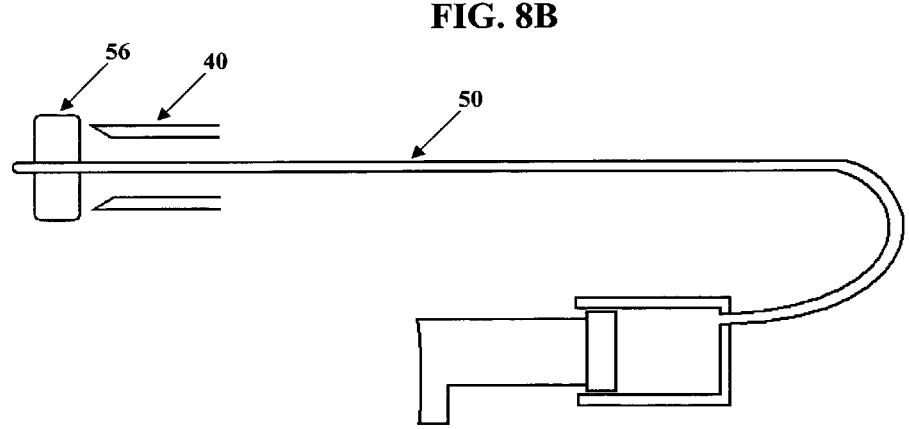

FIGS. 8 and 9 show a mechanism for controlling deployment of the retractor element 50. A slot 84 is cut into pushing element 80. Slot 84 has an index 84*a* to lock retractor element 50 at full extension and an index 84*b* to lock retractor element 50 at full retraction. Bolt 72*a* is rigidly attached to sliding plug 72. Bolt 72*a* can be manually displaced within slot 84 to position the retractor element 50. In operation, bolt 72*a* is positioned in index 84*a* until the retractor element 50 is fully inserted into the left ventricle and the expanding element 56 is at full expansion. At that time, bolt 72*a* is manually released from index 84*a*, which allows compression spring 70 to retract retractor element 50 until expanding element 56 contacts the inside wall of the left ventricle. A damping means (not shown) may be included to prevent sudden retraction of the retractor element upon release from index 84*a*. Also not shown is a safety latch or other means to prevent manual release of the bolt 72*a* until the expanding element 56 is fully expanded.

As the surgeon applies force and rotation using handle 90, compression spring 70 continues to displace retractor element 50. When retractor element 50 is fully retracted, the surgeon can rotate bolt 72*a* into index 84*b* to lock the retractor element 50 in place. Moreover, when retractor element 50 is fully retracted, the expanding element 56 is also fully retracted into coring element 40, indicating that the tissue plug has been successfully removed from the left ventricle and is within the coring element 40.

Figure 10B:
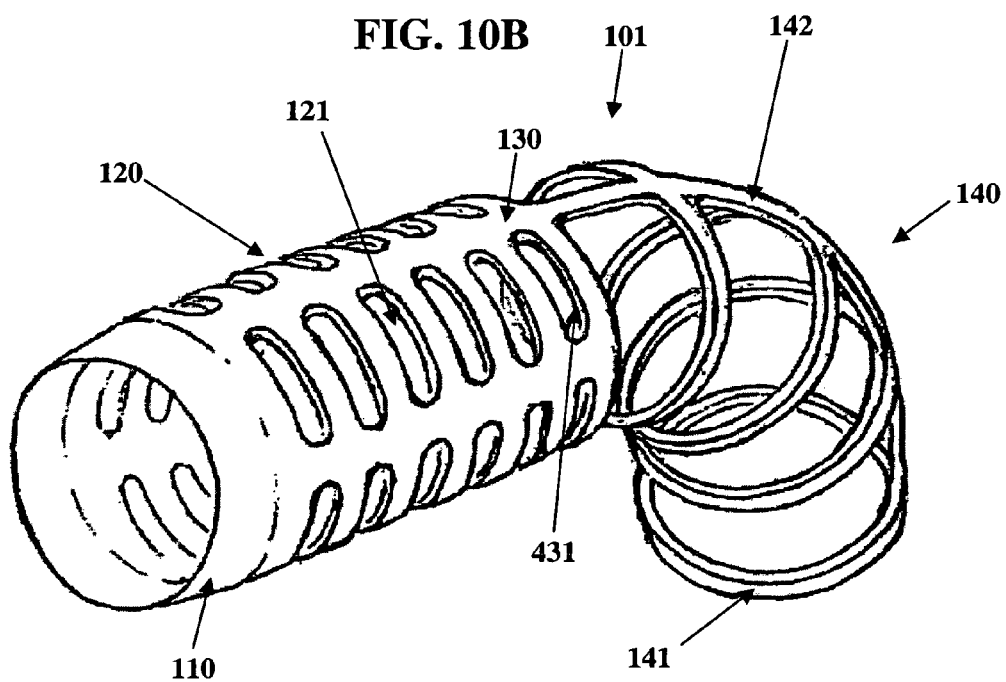
FIG. 10B is a perspective view of the structural frame of FIG. 10A shown inn a bent configuration.
Figure 10C:
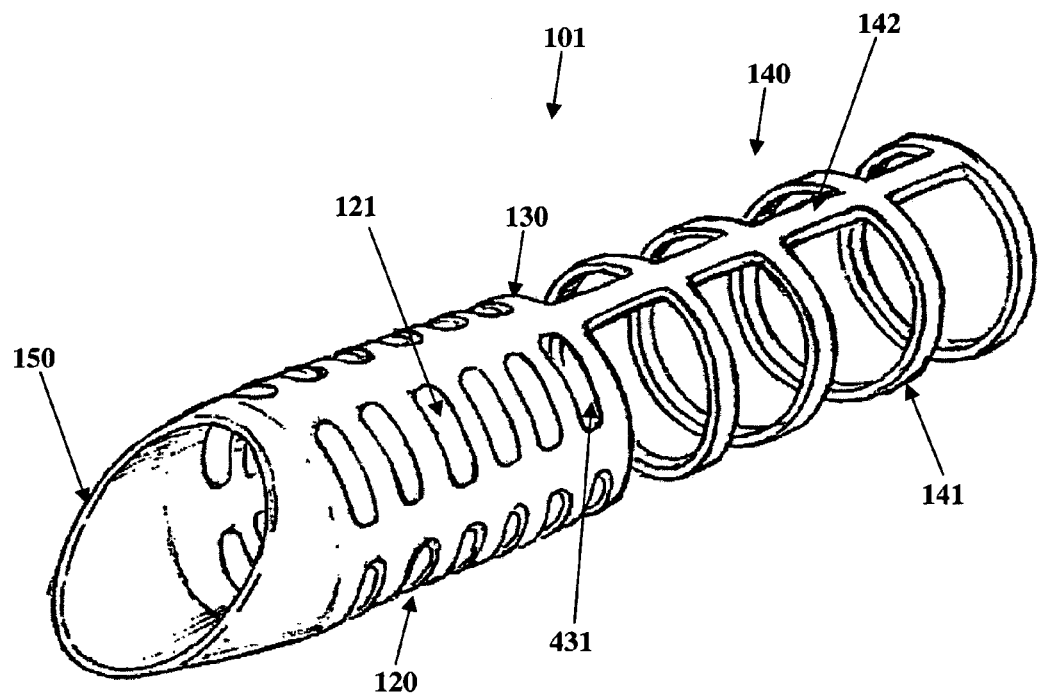
FIG. 10C is a perspective view of the structural frame of FIG. 10B shown with a beveled and tapered leading edge.

Referring to the embodiment of FIGS. 10A-10C, the connector conduit has a structural frame 101 defining a rigid portion, which may be constructed from a single material or a combination of materials. The structural frame 101 includes a tapered leading edge 110 designed to reduce the effort needed to push the connector through the heart wall located at one end of a cage section 120 and a bend portion 140 that is normally biased into a bent configuration. As shown in FIG. 10C, a tapered and beveled leading edge 150 may further reduce the required effort. During use, cage 120 resides primarily within the heart wall, so it must be constructed so as to be rigid enough to not collapse due to radial forces exerted by the heart wall. The cage 120 may include cage slots 121. The cage slots 121 allow the passage of thread to secure the conduit or the sewing flange.

Figure 11:
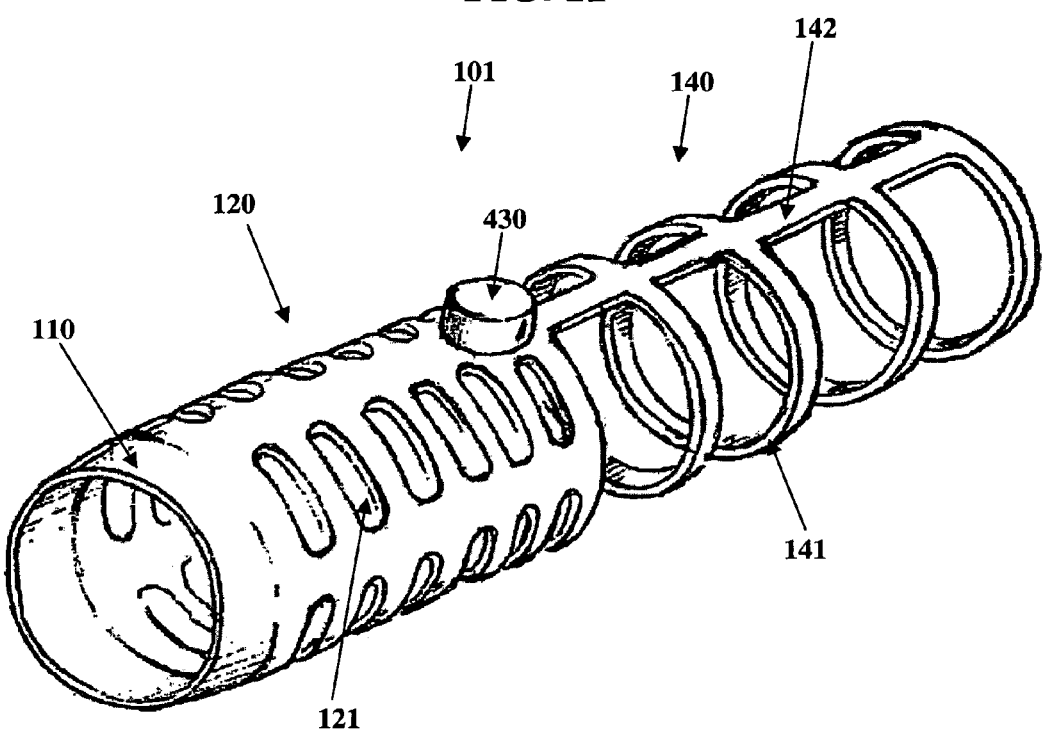
FIG. 11 is a perspective view of an alternative embodiment of FIG. 10A.
Figure 11A:
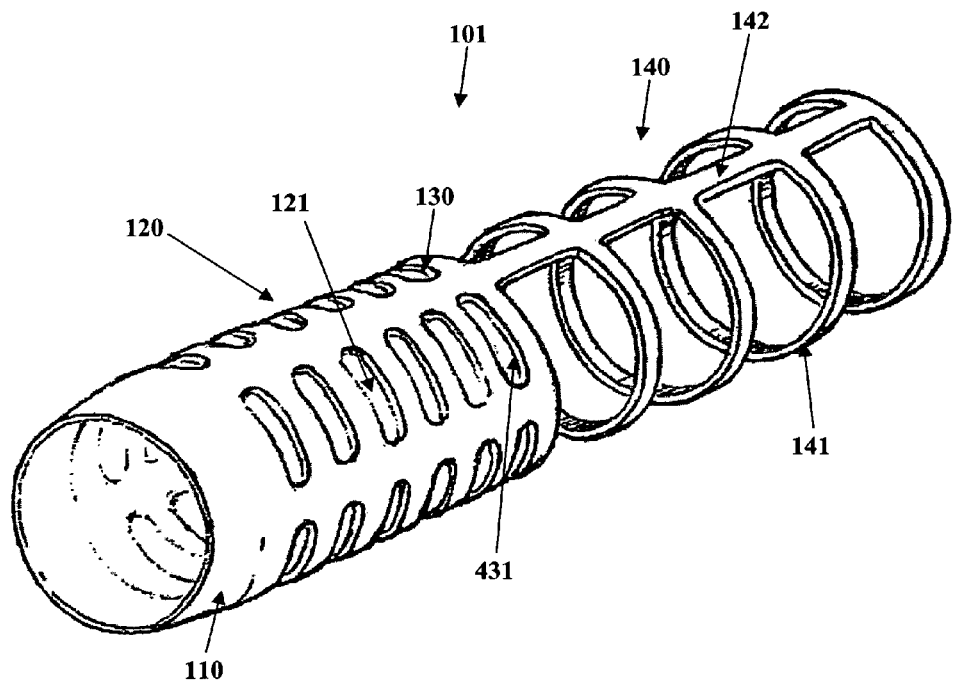
Figure 11B:
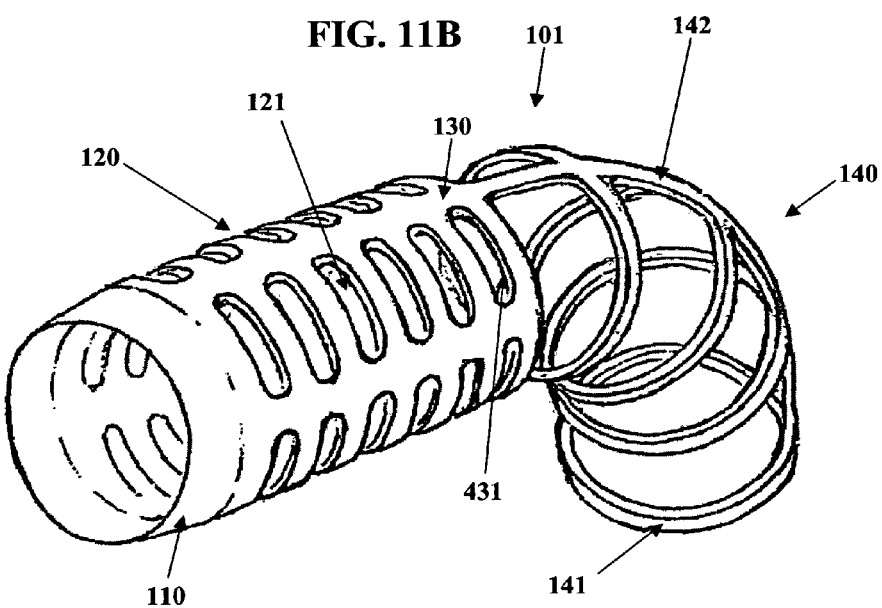
Figure 11C:
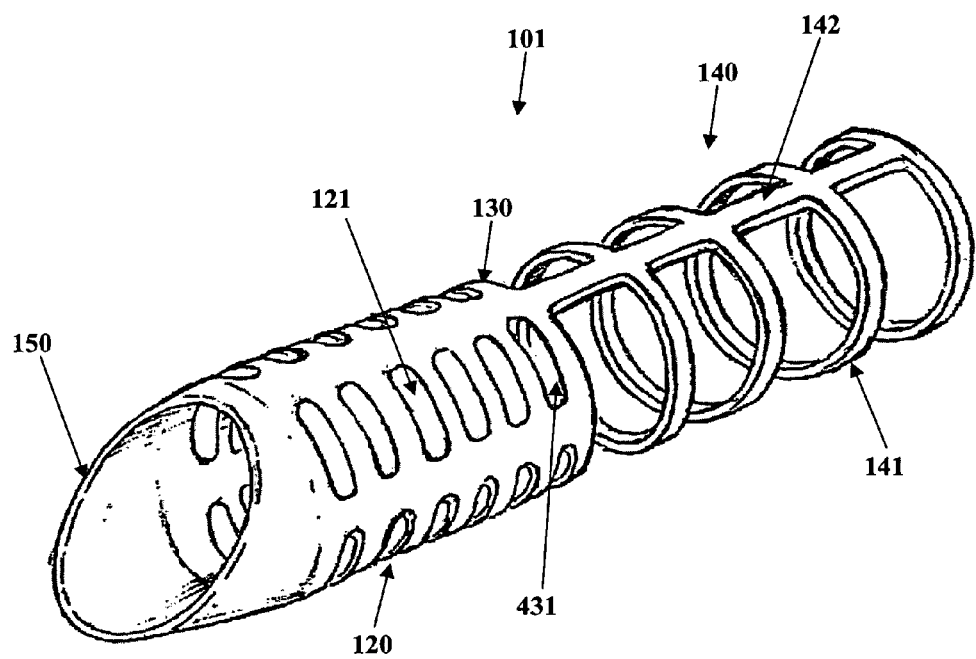

A holder 130 is formed at one end of cage 120 and may be used to grasp the connector during implantation. As will be described further herein, holder 130 can have a slot-and-key configuration with the applicator. As such, the holder 130 utilizes holder slots 431 or a holder button 430 (FIG. 11). Holder button 430 may be a separate part that is anchored (e.g., by thread or glue) to structural frame 101. If desired, the holder slots 431 or holder button 430 may be designed to place the flexible bend 140 or rigid bend 145 (FIG. 13) at a preferred angle relative to the applicator. Alternatively, the holder 130 may rely upon a tight friction fit with the applicator. In a preferred configuration, the holder 130 relies upon both a slot-and-key and a tight friction fit to lock the holder 130 relative to the applicator.

Referring again to FIGS. 10A and 10B, bend portion 140 includes circular rings 141 and a curved spine 142. The circular rings 141 prevent radial collapse of the conduit, and the curved spine 142 holds the conduit in a preferred shape to direct blood flow from the heart to the aorta. The curved spine 142 may be at the outer radius of bend portion 140 (as shown) or at the inner radius of the flexible bend. As an alternative, flexible bend 140 may include two curved spines at the mean radius. As another alternative, the structural frame 101 could include circular rings 141 without curved spine 142. As another alternative, a modified coil spring in the shape of a preferred bend could be used instead of circular rings 141 and curved spine 142. Properties of the coil spring would be chosen to prevent radial collapse and to provide appropriate stiffness of the curved position.

The structural frame of FIGS. 10A-11 is intended for mounting onto the outer diameter of a straight mounting element. As such, the bend portion 140 must be constructed to allow straightening of the curved spine 142. If curved spine 142 is made of a material or combination of materials with higher modulus of elasticity (e.g., PEEK, metal), the flexible bend 140 is stiffer. As such, the flexible bend 140 may be biased to resume a preferred shape (e.g., a 90° bend) when removed from the mounting element. If the curved spine 142 is made of a material with a lower modulus of elasticity (e.g., polypropylene, polyethylene), the bend portion 140 is less stiff. As such, the bend portion 140 may be biased relatively straight when removed from the straight mounting element. In such case, some bending means may be needed to position the bend portion 140 into the preferred shape.

Figure 12:
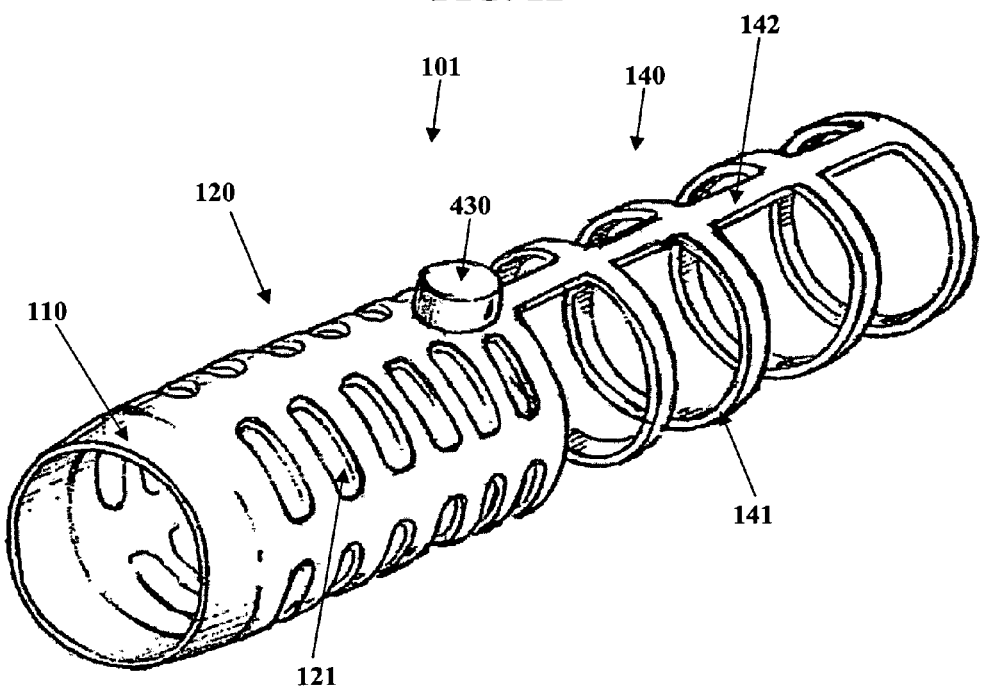
FIG. 12A is a perspective view of the flexible structural frame of FIG. 10A shown in the straightened configuration and incorporating a bending means.
FIG. 12B is a perspective view of the structural frame of FIG. 12A after activating the bending means.
Figure 12A:
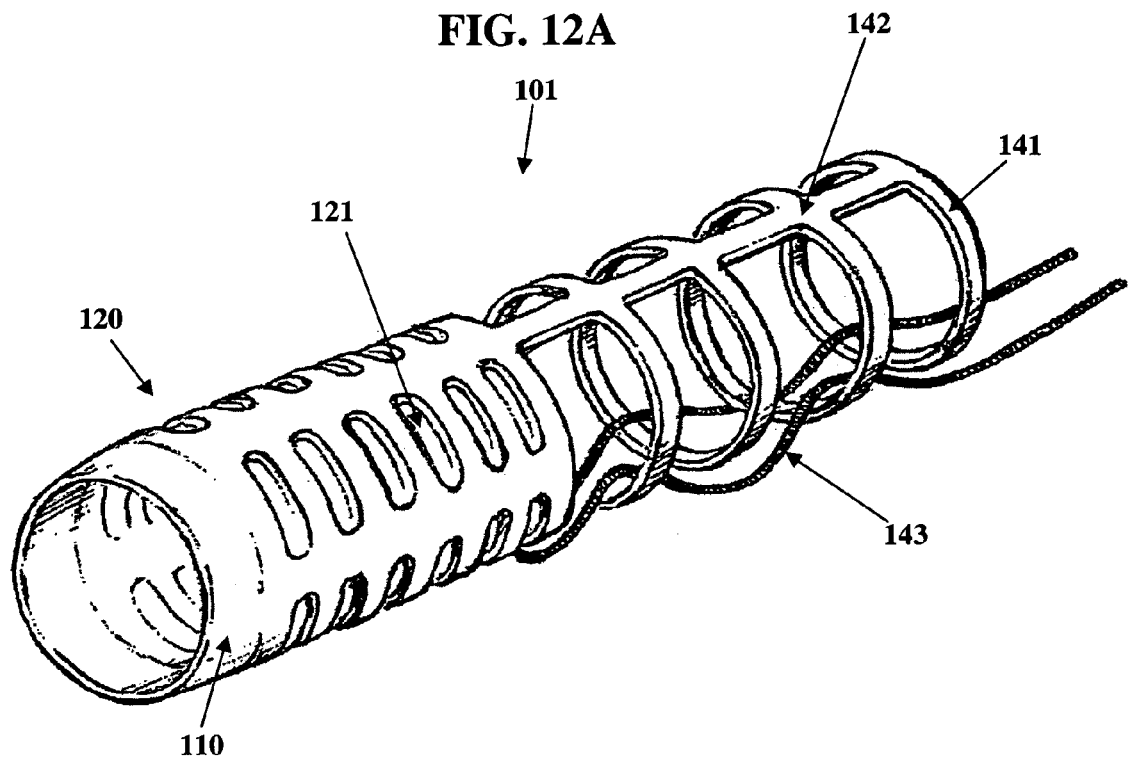
Figure 12B:
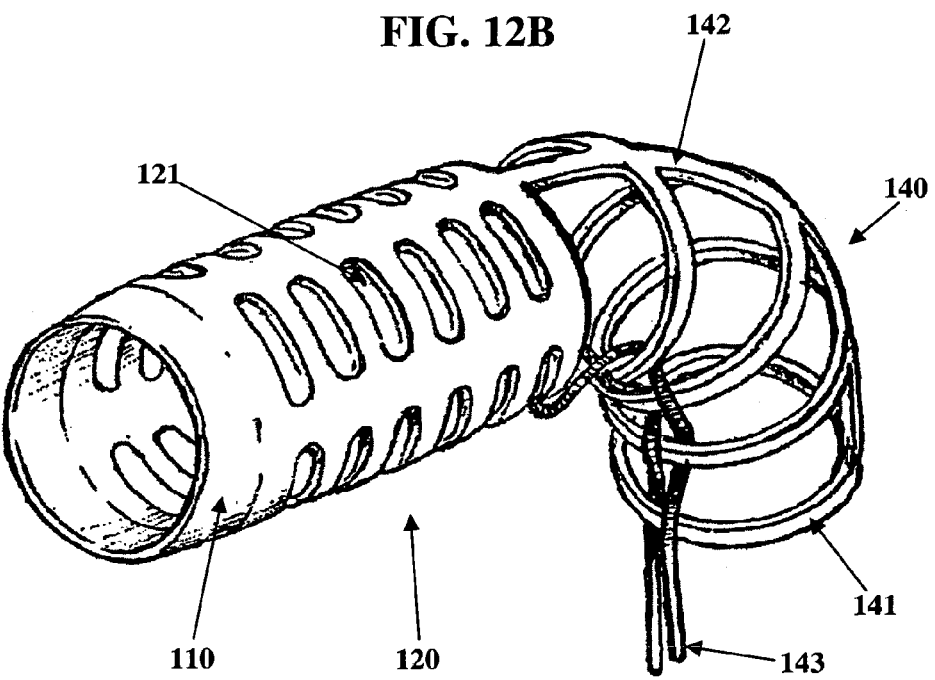

One embodiment of a bending means is shown in FIGS. 12A and 12B, which illustrate use of threads 143 that are secured to the holder 130 (for example) and weaved through circular rings 141. When threads 143 are pulled, the bend portion 140 changes from the normally biased, straight configuration of FIG. 12A to the bent configuration of FIG. 12B. When the flexible bend 140 reaches the preferred shape, the threads may be tied to form a knot or crimped. If desired, the bending means can be used with a curved spine 142 constructed of a high modulus of elasticity material to prevent straightening beyond the preferred angle.

Figure 13:
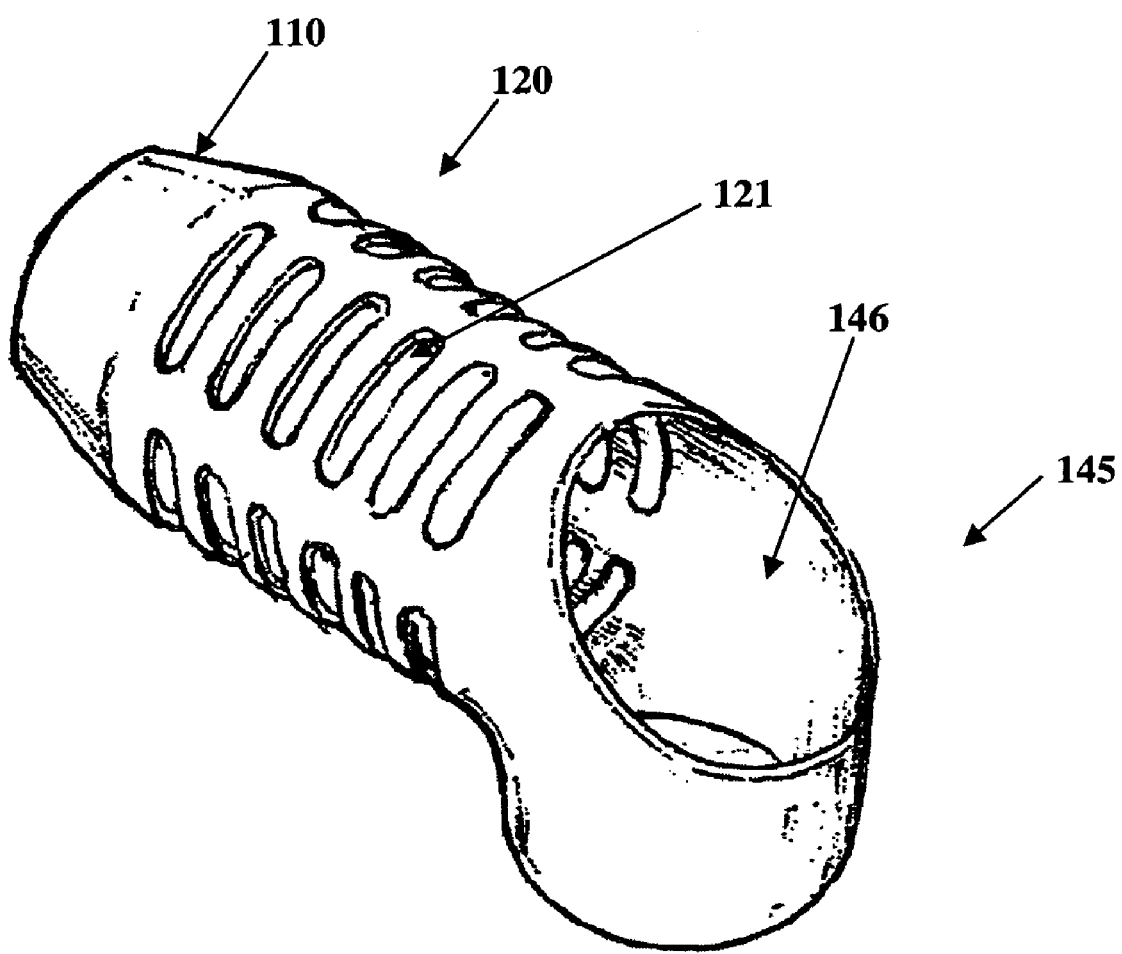
FIG. 13 is a perspective view of a non-bendable structural frame of a connector conduit.
Figure 13A:
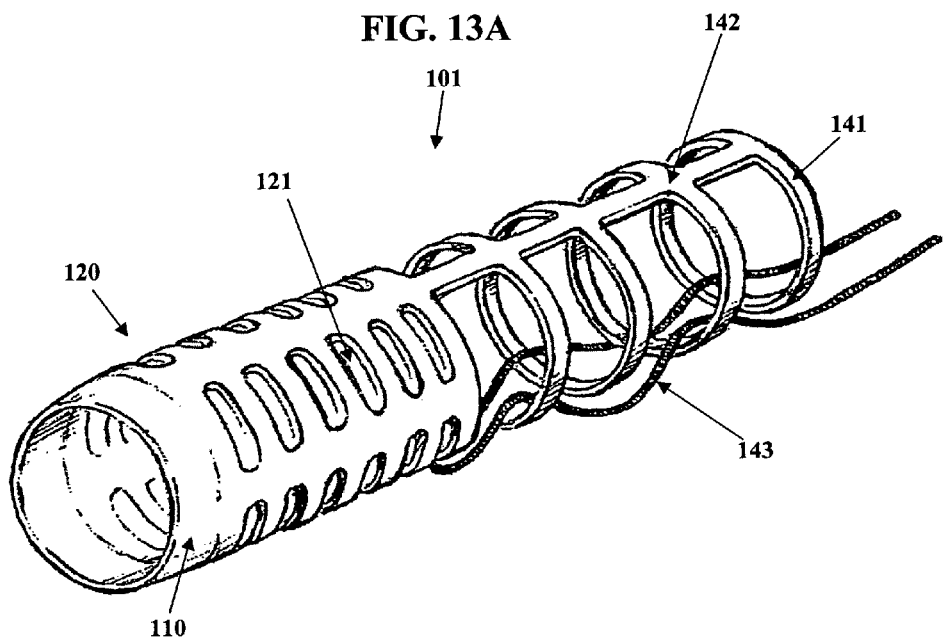
Figure 13B:
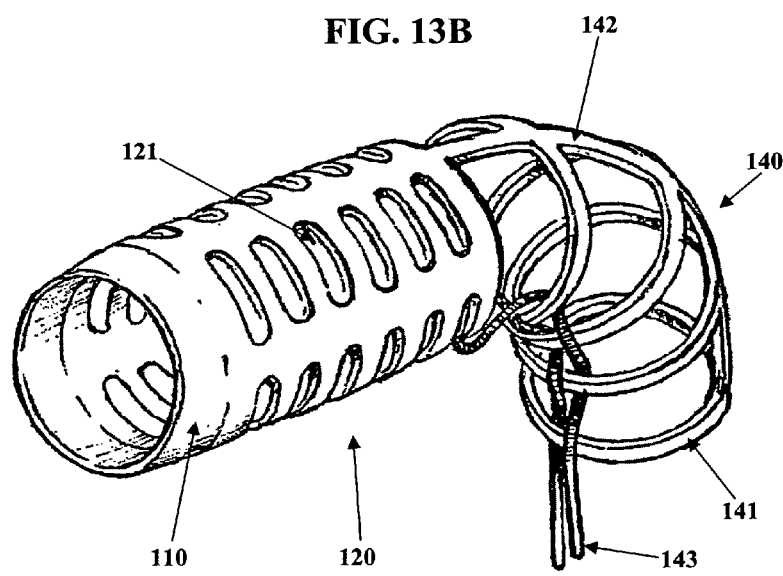

As discussed previously, structural frame 101 may be constructed with a fixed bend 145, as shown in FIG. 13. A port 146 allows the mounting of structural frame 101 with a fixed bend 145 onto a straight mounting element.

Figure 14:
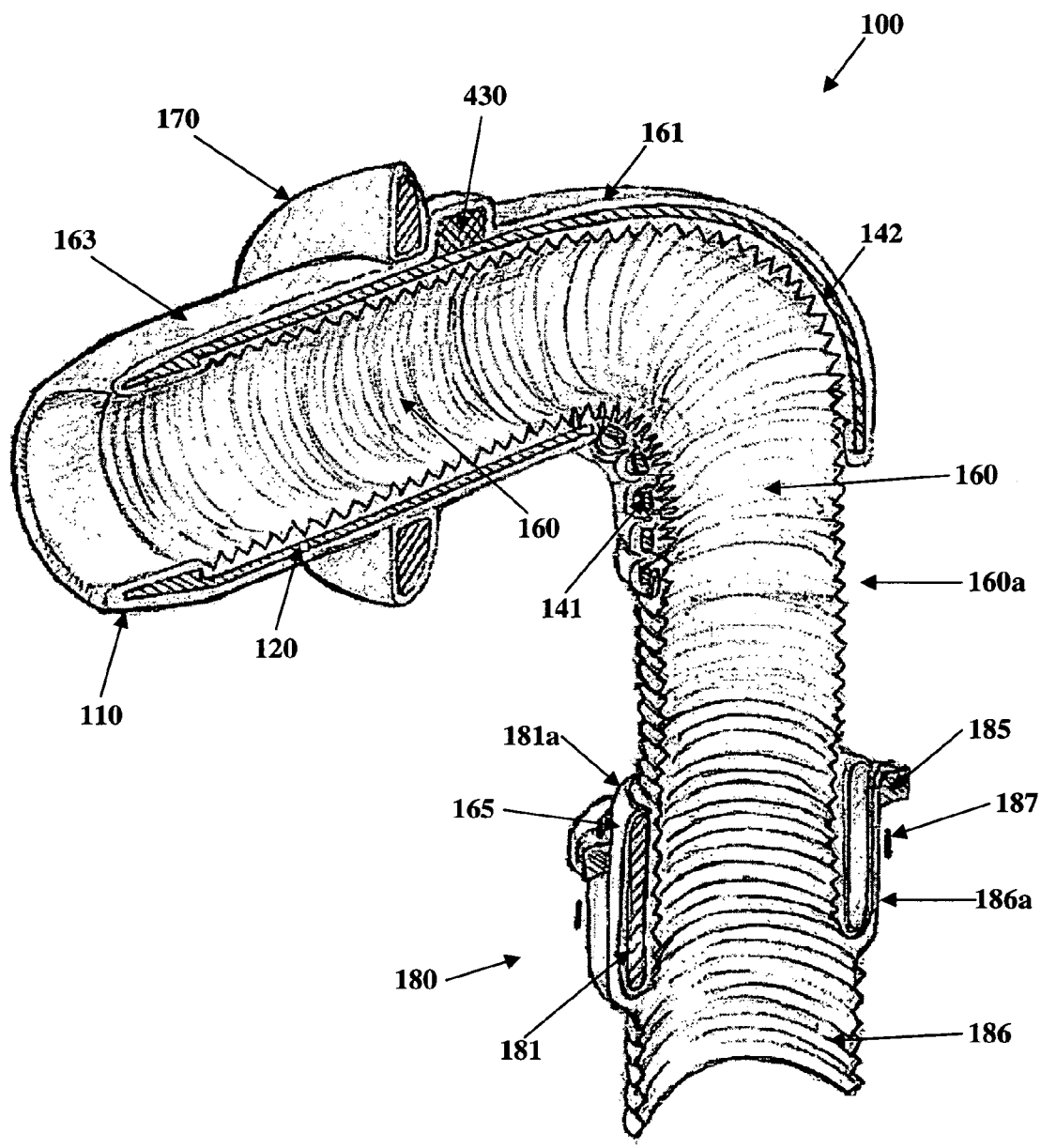
FIG. 14 is a cross-sectional view of a connector conduit shown in a bent configuration.

FIG. 14 is a cross-section of a connector conduit 100 that includes a rigid portion defined by structural frame 101 with bend portion 140, and a flexible portion defined by conduit 160. The rigid portion also includes outer fabric 161, and sewing flange 170. Orientation marks (not shown) may be included on the conduit 160 or outer fabric 161. Conduit 160 may be a pleated vascular graft constructed of woven Dacron. Outer fabric 161 could be a knitted Dacron fabric material that stretches to accommodate contours of the structural frame 101. Sewing flange 170 could be constructed of a soft silicone rubber, for example, to allow easy passage of a needle when fastening sewing flange (or sewing ring) 170 to the outer surface of the heart. To allow visualization on x-ray, for example, the sewing flange could be made radiopaque, such as by mixing barium sulfate into the silicone rubber. The sewing flange may have a cloth covering such as that used for outer fabric 161. Alternatively, the sewing flange 170 may consist entirely of folded cloth. The components of the connector conduit 100 may be fastened together as needed, such as with thread.

Figure 15:
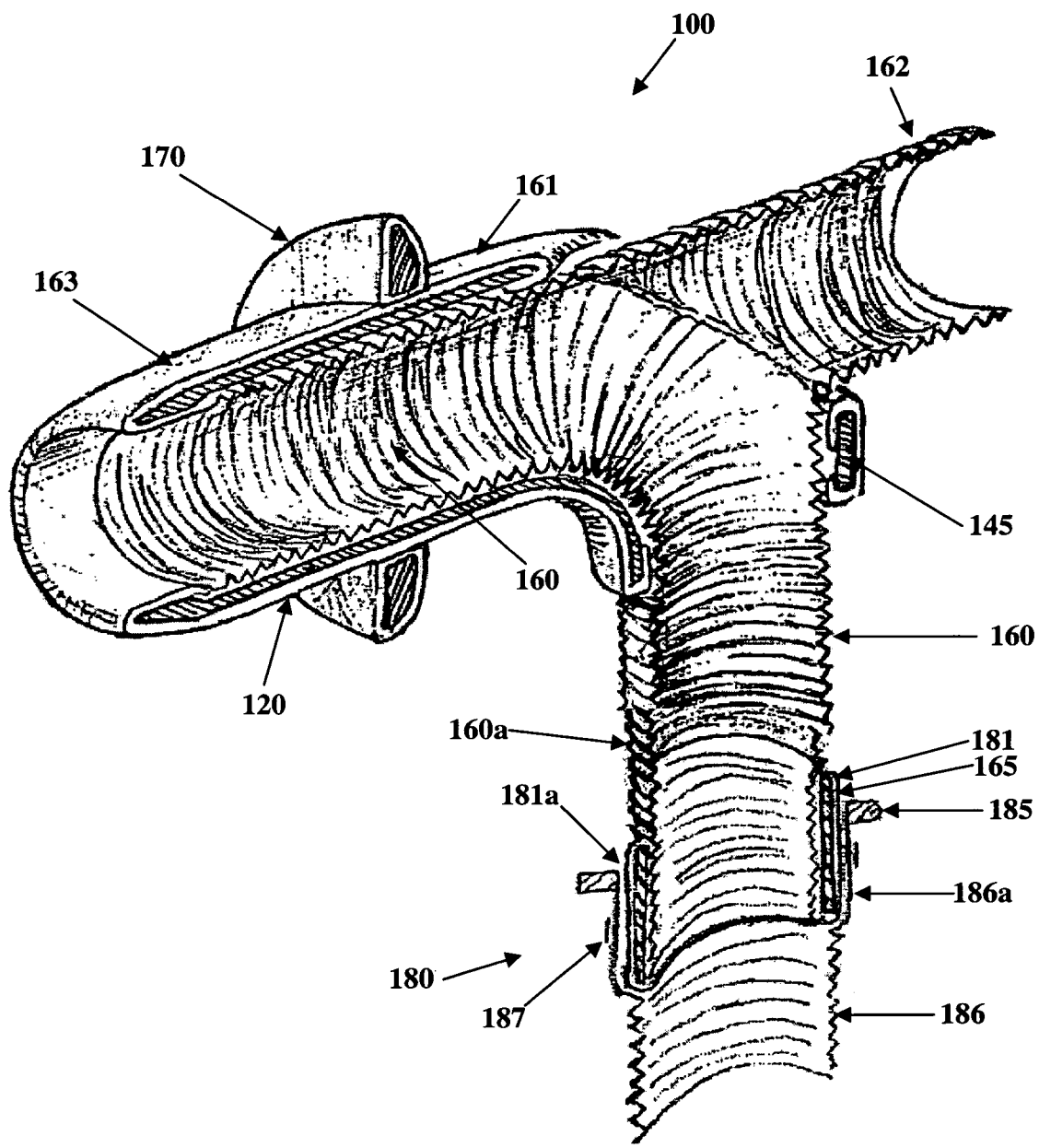
FIG. 15 is a cross-sectional view of a non-bendable connector conduit.

Referring to FIG. 15, a cross-section of a connector conduit 100 is similar to that shown in FIG. 14, except that the structural frame 101 is constructed with fixed bend 145. A conduit branch 162 intersects with conduit 160 through port 146 of rigid bend 145 to allow passage of a straight mounting element through the connector conduit 100. Once the connector conduit 100 is implanted into the ventricle, branch 162 may be occluded at the intersection with conduit 160. Branch 162 may then be cut off.

FIG. 14 and FIG. 15 further illustrate a quick connect coupler 180 for expediting attachment of the connector conduit 100 to the remainder of the prosthesis, which may include a prosthetic valve or ventricular assist device, as examples. As shown, the male end of quick connect coupler 180 is a continuation of or is attached to vascular graft 160. The male end of quick connect coupler 180 includes rigid connector frame 181, which may be constructed of a biocompatible plastic or metal. Vascular graft 160 covers the inner diameter of connector frame 181, and an outer fabric 165 covers the outer diameter of connector frame 181. Outer fabric 165 may be continuous with vascular graft 160. Outer fabric 165 is not of a pleated construction, such as is typical of vascular graft 160. The cloth-covered connector frame 181 provides a rigid surface onto which the female end of quick connect coupler 180 may be mounted. The female end of quick connect coupler 180 includes vascular graft 186 and pull ring 185. Vascular graft 186 attaches on its downstream end to the remainder of the prosthesis, which may include a prosthetic valve or ventricular assist device, as examples. Vascular graft 186 may be a pleated vascular graft constructed of woven Dacron, for example. Graft extension 186a is a continuation portion of or is attached to vascular graft 186. A rigid pull ring 185 (which may be constructed of a biocompatible plastic or metal) is attached to graft extension 186a. The male end of quick connect coupler 180 has a larger outer diameter than vascular graft 186. This construction provides a stop so that the male end of quick connect coupler 180 reaches an abrupt change to a smaller diameter provided by vascular graft 186. In this way, the surgeon knows when the male end is fully inserted into the female end of quick connect coupler 180. In use, the surgeon may grasp pull ring 185 with one hand and connector frame segment 181a of connector frame 181 with the other hand. Pull ring 185 is pulled over outer fabric 165 until the male end of quick connect coupler 180 contacts the smaller diameter vascular graft 186. A large suture or umbilical tape 187 may then be tied around graft extension 186a to reduce blood loss by occluding the annular gap between the outer diameter of outer fabric 165 and the inner diameter of graft extension 186a. Stay sutures may also be used to connect outer fabric 165 to graft extension 186a, thereby preventing separation of the male and female ends of quick connect coupler 180.

FIG. 14 and FIG. 15 further illustrate a collapsible portion 160a between connector conduit 100 and quick connect coupler 180. Such collapsible portion 160a allows use of a cross clamp, for example, to fully collapse portion 160a to occlude flow after the applicator is removed beyond collapsible portion 160a. Collapsible portion 160a can be made of the same material as the rest of the flexible portion, or can be made of a different material.

Figure 16:
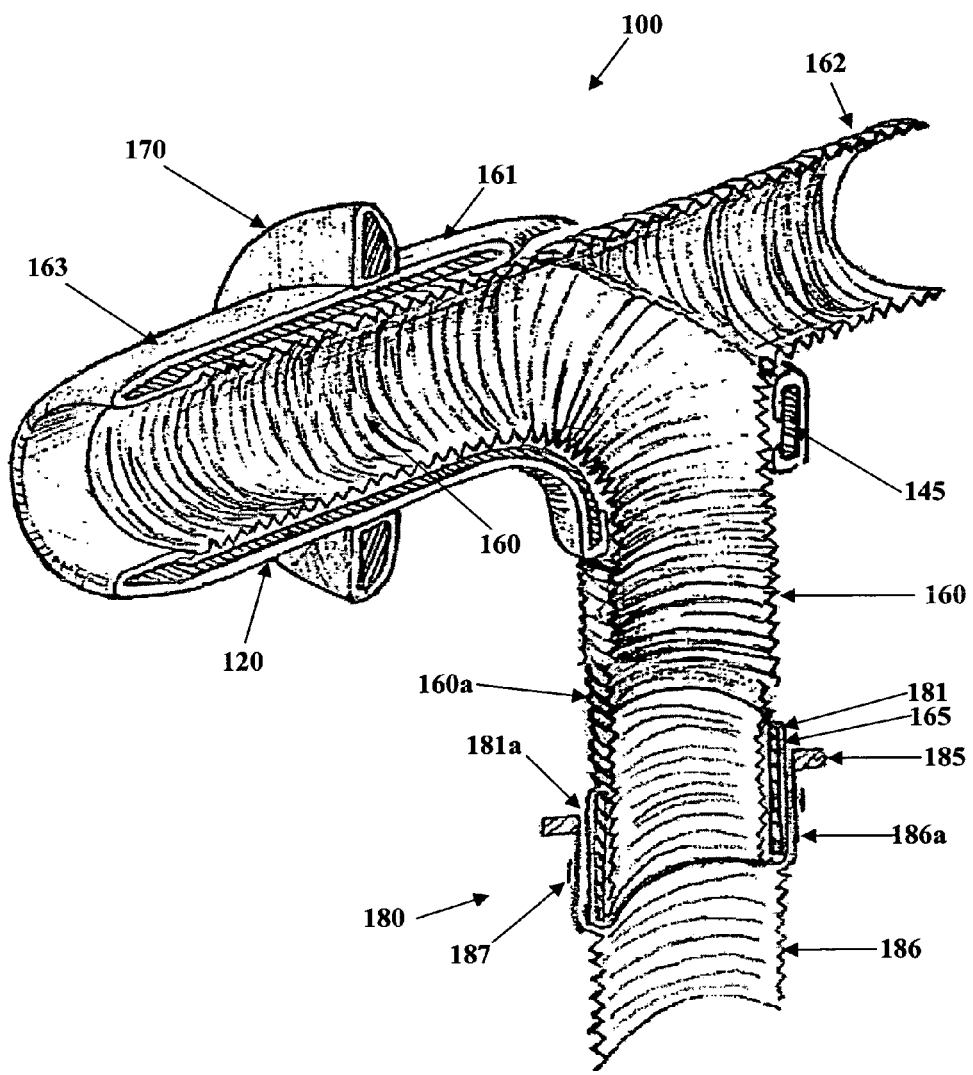
FIG. 16A is a cross-sectional view of a mounting element (including a coring element) and a pushing element of the applicator with a loaded connector conduit.
FIG. 16B is a cross-sectional view FIG. 16A without the connector conduit.
Figure 16A:
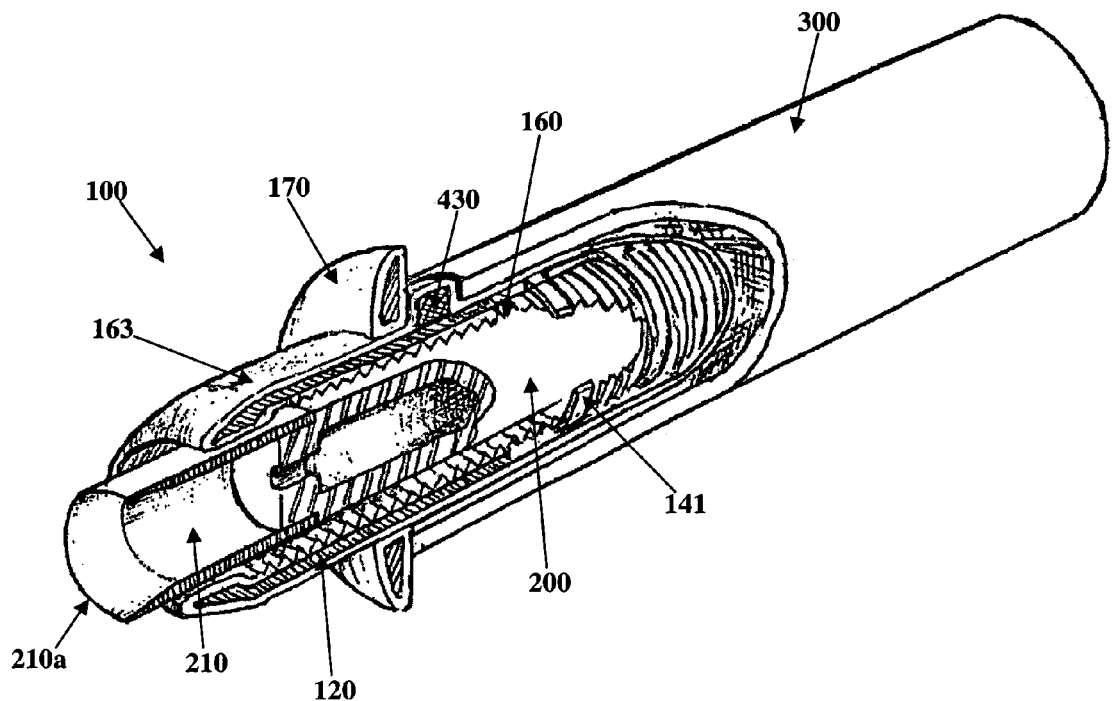

In use, the applicator of the present invention is used to implant the connector conduit 100 into the ventricle wall or other organ wall. FIG. 16A shows a cross-section of the connector conduit 100 (FIG. 14) loaded onto a mounting element 200. For clarity, the applicator is shown without the connector conduit 100 in FIG. 16B. Mounting element 200 includes a cylindrical coring element 210, serving as a hole forming element, that is concentric with and has the same diameter as the mounting element 200. The mounting element 200 and coring element 210 are placed concentrically within the lumen of the connector conduit 100. Coring element 210 includes a thin-walled tube and a sharpened cutting edge 210a, which may be tapered on the inner diameter, for example, to form the sharpened cutting edge 210a. The coring element 210 is used to cut a cylindrical-shaped core (or hole) in the heart wall, producing a plug from the heart wall that resides within the coring element 210. The mounting element 200 could be constructed of plastic (e.g., ABS), and the coring element 210 could be constructed of metal (e.g., stainless steel). In a preferred embodiment, the mounting element 200 and coring element 210 have an outer diameter that closely matches the inner diameter of the connector conduit 100. One purpose of such a construction is to minimize blood loss from the left ventricular chamber when the coring element 210 has completed its cut. Also in order to reduce blood loss from the left ventricular chamber and from the cut myocardial surface and to yield a snug fit of the connector conduit within the ventricular myocardium, the cutting diameter of the coring element 210 is chosen to produce a core that is smaller in diameter than the outer surface 163 of the of the connector conduit 100.

Figure 16B:
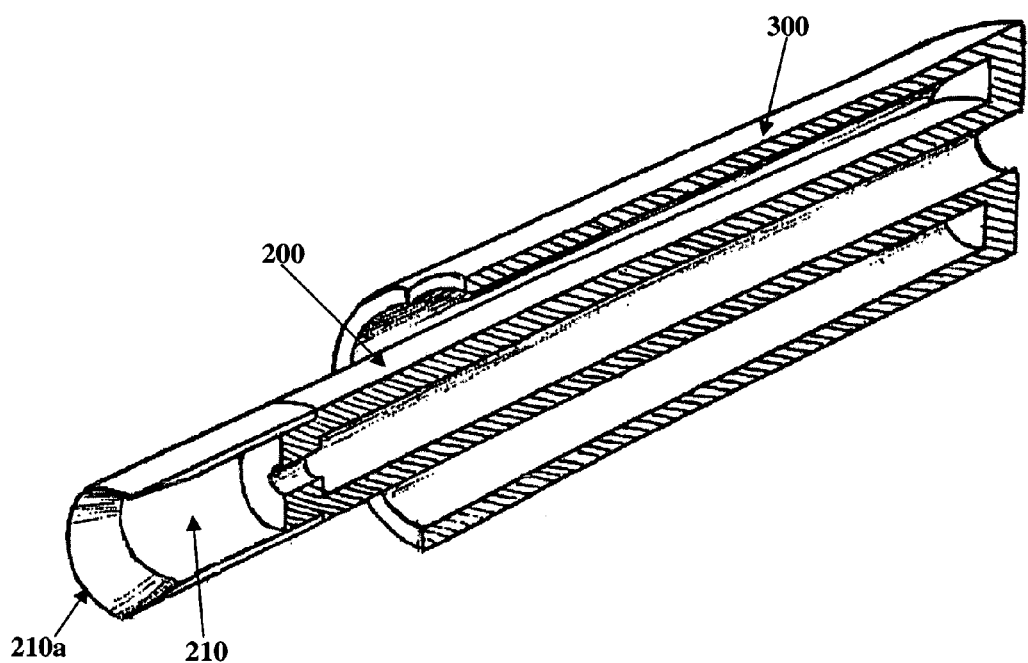

FIG. 16A and FIG. 16B further illustrate a cylinder-shaped pushing element 300 positioned concentrically outside the connector conduit 100. In a preferred embodiment, the pushing element 300 transmits pushing force and rotation to the connector conduit 100. In further accordance with a preferred embodiment, the pushing element 300 is rigidly attached to mounting element 200, such that pushing element 300 transmits pushing force and rotation to the mounting element 200 and coring element 210. Pushing element 300 may be constructed of plastic (e.g., ABS) or metal (e.g., stainless steel). However, it should be appreciated that the present invention contemplates the use of other materials.

Figure 17A:
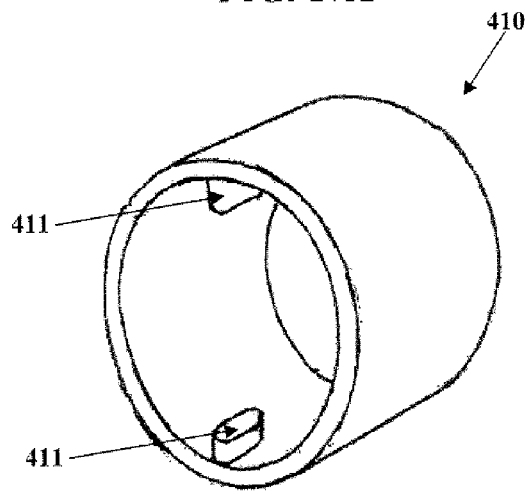
FIG. 17 is a perspective view of a squeeze ring for a locking means to secure the connector conduit within the applicator.
FIG. 17B is a perspective view of a locking means shown in the locked position.
FIG. 17C is a perspective view of a locking means shown in the unlocked position.
Figure 17B:
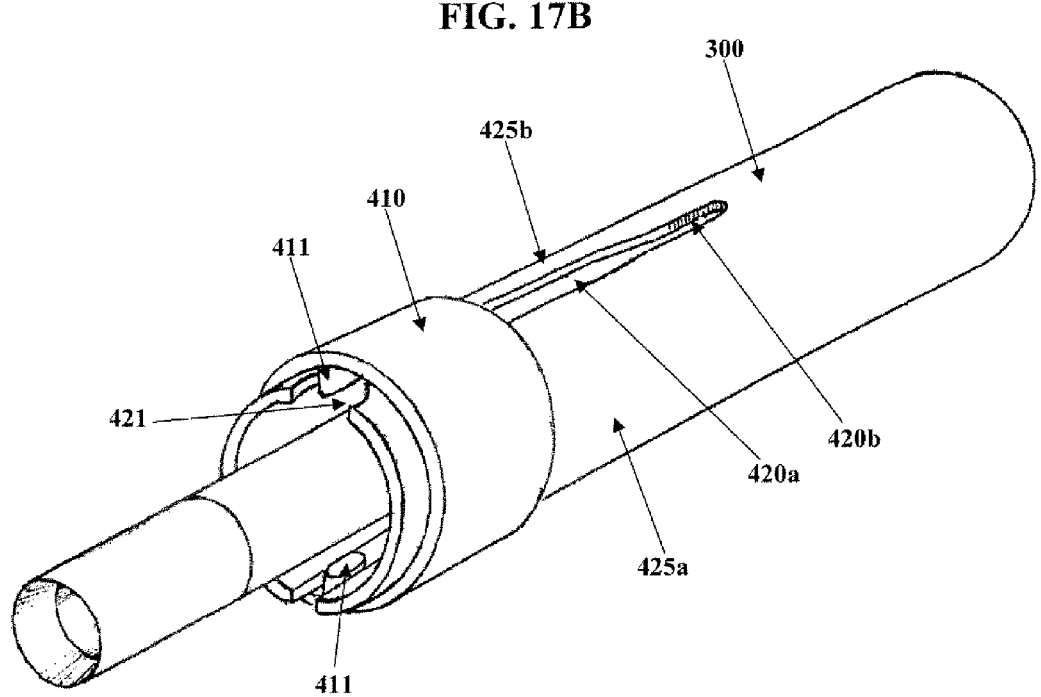
Figure 17C:
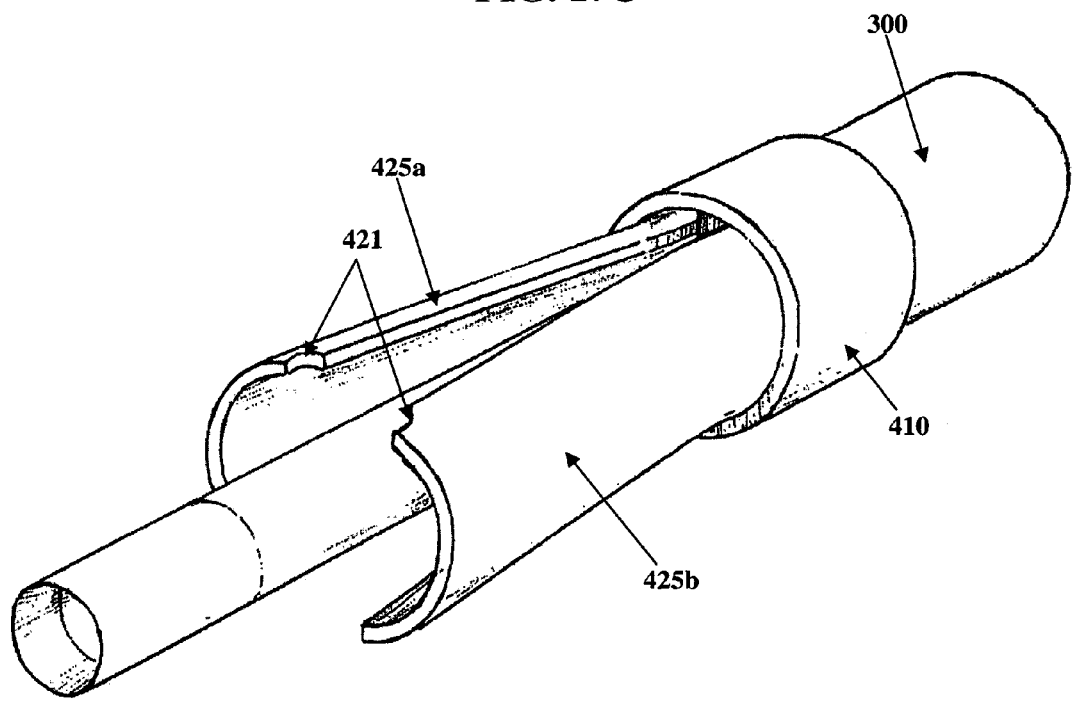

In further accordance with a preferred embodiment, a locking means provides an interface that prevents movement of the connector conduit 100 relative to the pushing element 300. Such locking means may include components that are integral with the pushing element 300, connector conduit 100, mounting element 200, and coring element 210. FIGS. 17A to 17C illustrate one embodiment of such a locking means. This embodiment combines a slot-and-key arrangement with a friction enhancing arrangement. The slot-and-key arrangement includes notch 421 (the slot) of pushing element 300 and holder button 430 (the key) of structural frame 101. Positioning holder button 430 into notch 421 prevents rotation of connector conduit 100 relative to pushing element 300 and prevents axial motion in one direction. Axial motion allowing removal of the connector conduit 100 from the applicator is not prevented in this embodiment. Rather, this axial motion is reduced by providing a friction enhancing arrangement consisting of squeeze ring 410 (which includes two groove pins 411) and squeeze arms 425a and 425b that cantilever from pushing element 300 to form wide groove 420a and narrow groove 420b. Alternatively, notch 421 could fit tightly around the circumference of holder button 430 to prevent movement of the connector conduit 100 relative to the pushing element 300 in both rotational and axial directions. As shown, notch 421 is divided, with one half cut from squeeze arm 425a and the other half from squeeze arm 425b. Alternatively, notch 421 could reside entirely within either squeeze arm. Alternatively, several notches 421 could be used.

When squeeze ring 410 is positioned at or near notch 421 as shown in FIG. 17B, squeeze ring 410 holds squeeze arms 425a and 425b tightly against connector conduit 100, creating a tight friction fit. In this position, groove pins 411 within wide groove 420a do not tend to separate squeeze arms 425a and 425b. When squeeze ring 410 is positioned as shown in FIG. 17C, groove pins 411 within narrow groove 420b tend to separate squeeze arm 425a and 425b to allow the connector conduit to be easily moved into position or removed. In a similar embodiment (not shown), the slot-and-key arrangement could include teeth (keys) that extend radially inwards from the inner diameter of squeeze arms 425a and 425b to fit into holder slots 431 of holder 130 of structural frame 101 (see FIG. 10A). In this embodiment, a squeeze ring (with groove pins) and squeeze arms similar to those shown in FIGS. 17A to 17C would be used to engage and disengage the teeth from holder slots 431, rather than to provide a tight friction fit.

Figure 18:
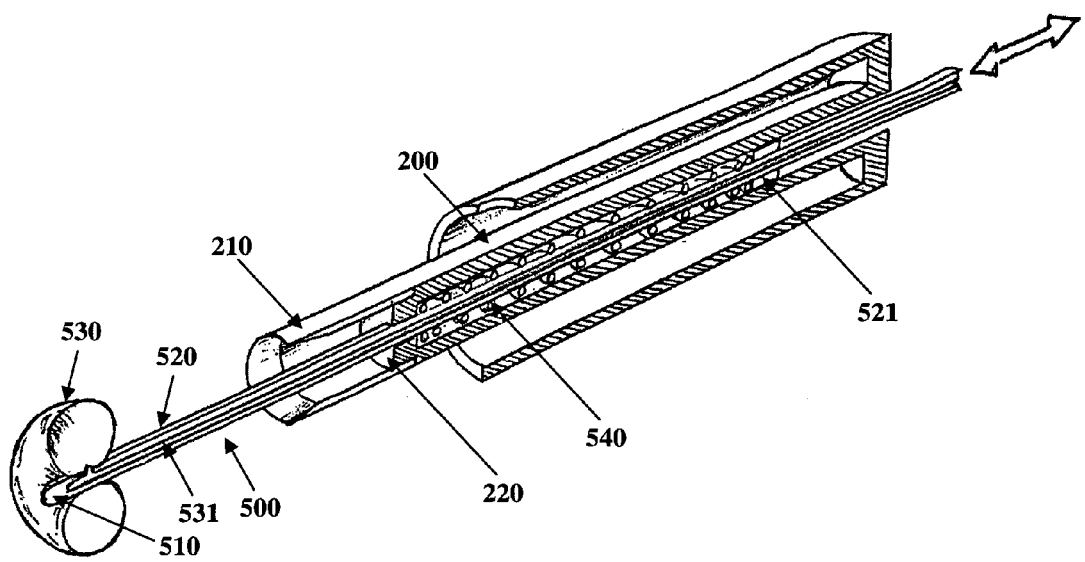
FIG. 18 is a cross-sectional view of the device of FIG. 16B including a retractor element.
Figure 18C:
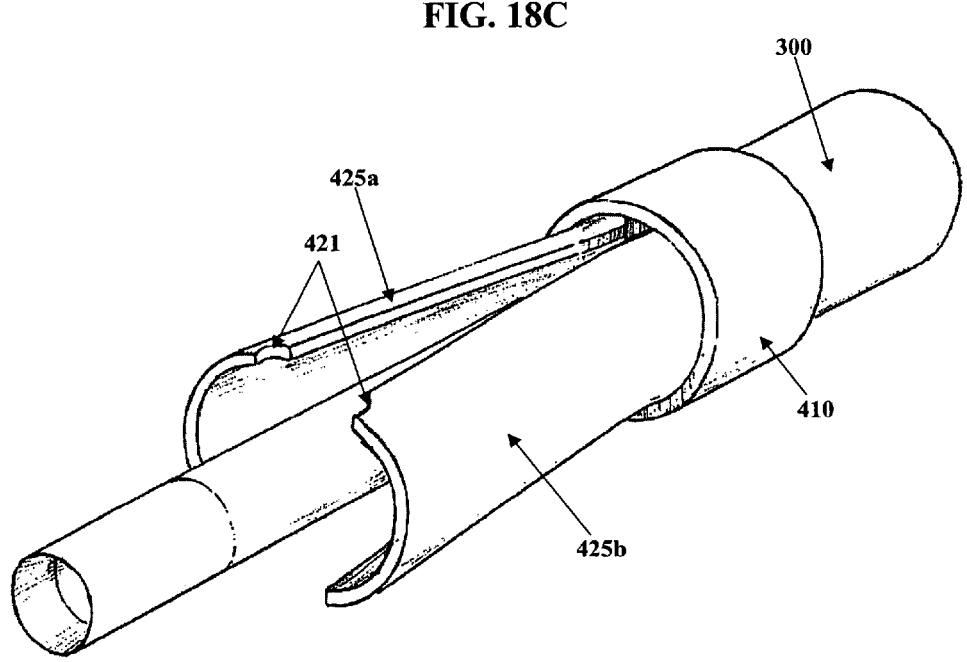

In accordance with a further embodiment of the present invention, a retractor component/element 500 with a generally tubular structure is located concentrically within the mounting element 200, as shown in FIG. 18. The retractor element 500 can slide axially relative to the mounting element 200. The retractor element 500 consists of a blunt tip 510, a tubular body 520, and an expanding element 530 that includes an access passage 531. The expanding element 530 is shown as a balloon in FIG. 18, which may be inflated and deflated with fluid (e.g., saline) through access passage 531 using a plunger and cylinder arrangement.

Retractor element 500 is held concentric within the mounting element 200 by centering plug 220 and sliding plug 521. Centering plug 220 is rigidly attached to mounting element 200, and sliding plug 521 is rigidly attached to tubular body 520. Since radial force from the heart wall tends to deflect the expanding element 530, tubular body 520 must have a sufficient stiffness to substantially resist such deflection. Such deflection may also be reduced by limiting the axial distance between the expanding element 530 and centering plug 220.

A coupling element, such as compression spring 540, slideably couples retractor element 500 to mounting element 200. Compression spring 540 biases retractor element proximally to ensure that expanding element 530 seats snugly against the inside wall of the ventricle to shape and partially flatten the ventricle wall (particularly at the apex) so that coring element 210 may cut perpendicular to the ventricle wall. Once the tissue plug is cut from the ventricle by coring element 210, spring 540 pulls the tissue plug fully within the coring element 210. In the preferred embodiment, expanding element 530 is a balloon in the shape of a circular toroid.

Figure 19:
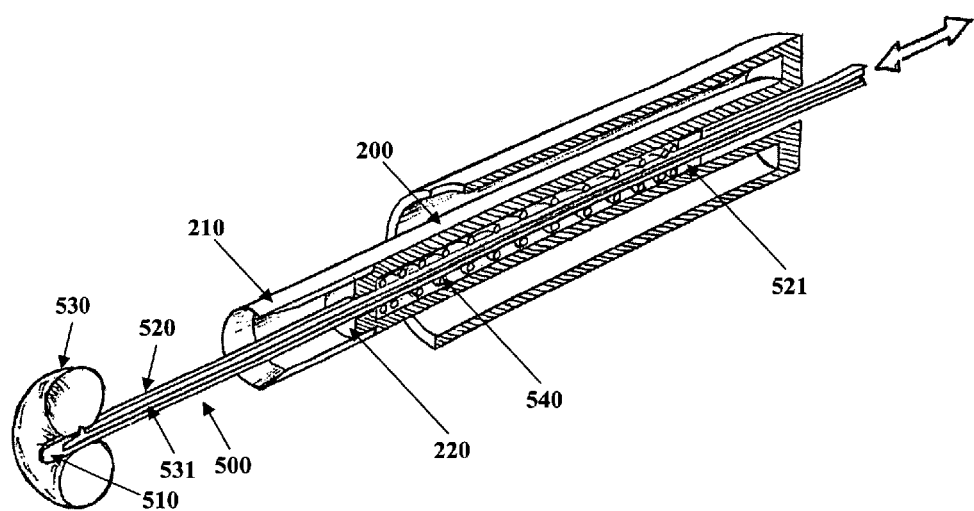
FIG. 19 is a cross-sectional view of a folding and mounting tool.

FIG. 19 illustrates a mounting and folding tool 900, which includes coring element taper 910, balloon taper 920, conduit taper 930, and retractor element port 940. Tool 900's outer diameter may be equal to or slightly larger than coring element 210's outer diameter to prevent damage to fabrics of the vascular graft 160 and outer fabric 161, when the connector conduit 100 is being mounted onto or demounted from mounting element 200. As an alternative, a thin-walled tube, such as a plastic shrink tube, may be positioned over outer diameters of tool 900 and coring element 210 to further prevent damage to fabrics slid past the sharpened edge 210a of the coring element. Coring element taper 910 fits snugly within coring element 210 to ensure a concentric fit between tool 900 and coring element 210, thereby further reducing the likelihood of damage to vascular graft 160 and outer fabric 161. Conduit taper 930 eases placement of vascular graft 160 onto tool 900. Tool 900 may be used to deflate and fold expanding element 530 by placing tool 900 onto retractor element 500 and by pushing and rotating (in one direction) tool 900 until coring element taper 910 contacts coring element 210. Balloon taper 920 provides a surface for controlled deflation and folding of the expanding element 530. Once the balloon is deflated and folded and the connector conduit 100 is fully mounted onto the applicator, tool 900 may be removed.

Figure 20:
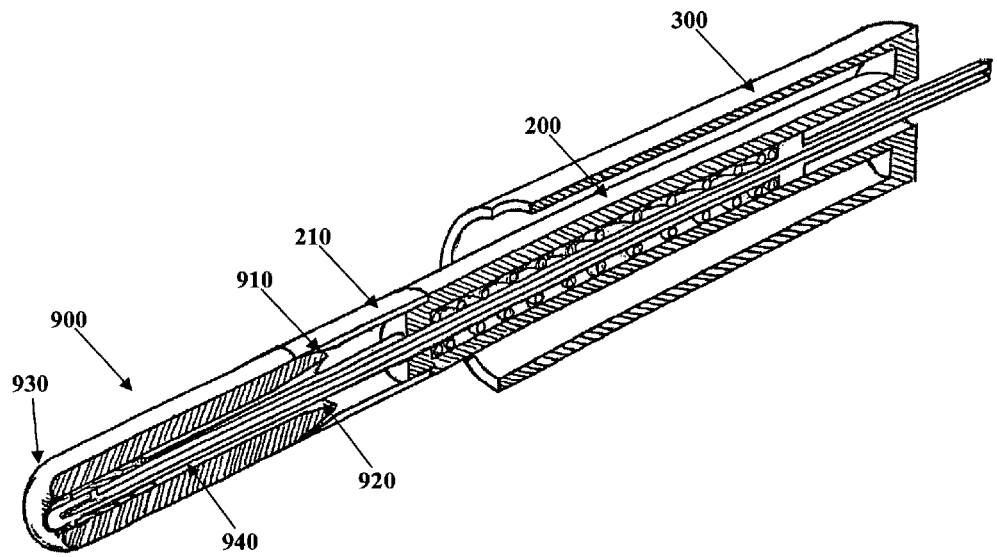
FIG. 20 is a cross-sectional view of an assembly including an applicator having a syringe.

FIG. 20 illustrates an embodiment of an applicator assembly (connector conduit 100 not shown). In this assembly, the surgeon has independent control of the position of retractor element 500 and the volume of expanding element 530. Handle 310, which extends from pushing element 300 to form a pistol grip, provides a means for the surgeon to apply axial force and back-and-forth rotary motion while implanting connector conduit 100. The position of retractor element 500 is controlled by the position of retractor bolt 522 in slot 320 of pushing element 300. Retractor bolt 522 is rigidly attached to sliding plug 521 of retractor element 500. Slot 320 is extended circumferentially to form index 321, which may be used to hold the retractor element 500 fully extended (i.e., with expanding element 530 at maximum distance from coring element 210). Expanding element 530 is connected to cylinder 562 by access passage 531 and flexible tube 550. Expanding element 530 volume is controlled by the position of plunger 600 in cylinder 562. Cylinder 562 is oriented in handle 310 so that plunger 600 with trigger 563 forms a pistol handle with trigger arrangement. Expanding element 530 can be inflated with saline, when trigger 563 is squeezed. Plunger spring 565 may be used to deflate expanding element 530 when the trigger is released. Alternatively, trigger 563 could be replaced with a finger ring so that the user must apply force to control both inflation and deflation of expanding element 530, thereby eliminating the need for plunger spring 565. As a safety feature, the plunger 600 may include a latching device (not shown) that latches the plunger 600 with the balloon fully inflated, thereby preventing premature deflation of the balloon. A related safety feature may include another latching device (not shown) that latches plunger 600 with the balloon partially inflated, such as to prevent the tissue plug from coming off of retractor element 500. As one of many alternatives to handle 310, the handle could form a "T" with pushing element 300.

In operation, retractor bolt 522 is positioned in index 321 until the retractor element 500 is fully inserted into the ventricle and expanding element 530 is fully inflated. At that time, retractor bolt 522 is manually released from index 321, which allows compression spring 540 to retract retractor element 500 until expanding element. 530 contacts the inside wall of the ventricle. A damping means (not shown) may be included to prevent sudden retraction of the retractor element 500 upon release from index 321. Also not shown is a safety latch or other means to prevent manual release of the retractor bolt 522 until the expanding element 530 is fully expanded. As the surgeon applies force and rotation using handle 310, compression spring 540 continues to displace retractor element 500. When retractor element 500 is fully retracted, expanding element 530 is also fully retracted to within coring element 210, indicating that the tissue plug has been successfully removed from the left ventricle and is within the coring element 210.

Figure 21:
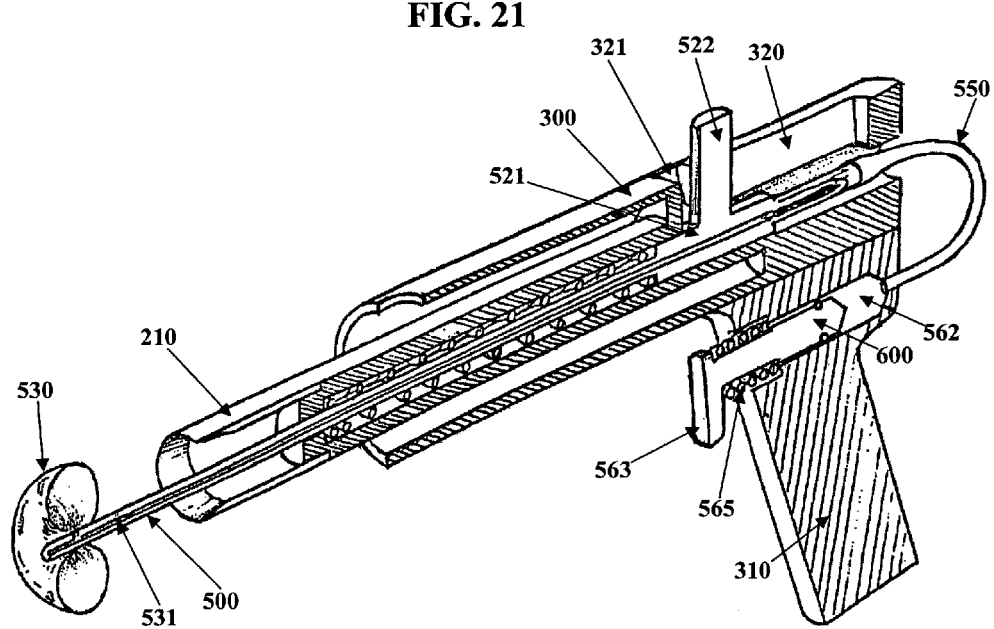
FIG. 21A is a cross-sectional view of a sequencing bolt.
FIG. 21B is a cross-sectional view of the retractor body and expanding element.
FIG. 21C is a cross-sectional view of the positioning means and coring element.
Figure 21A:
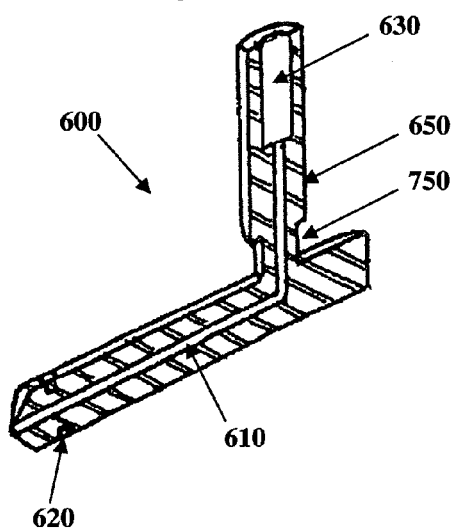
Figure 21B:
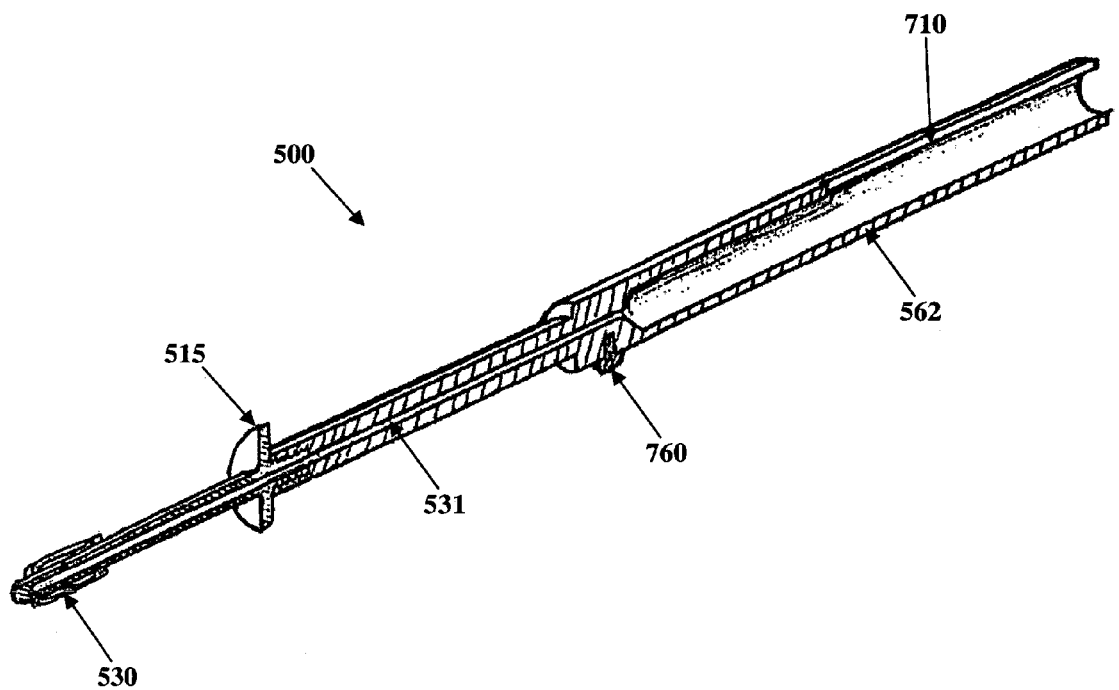
Figure 21C:
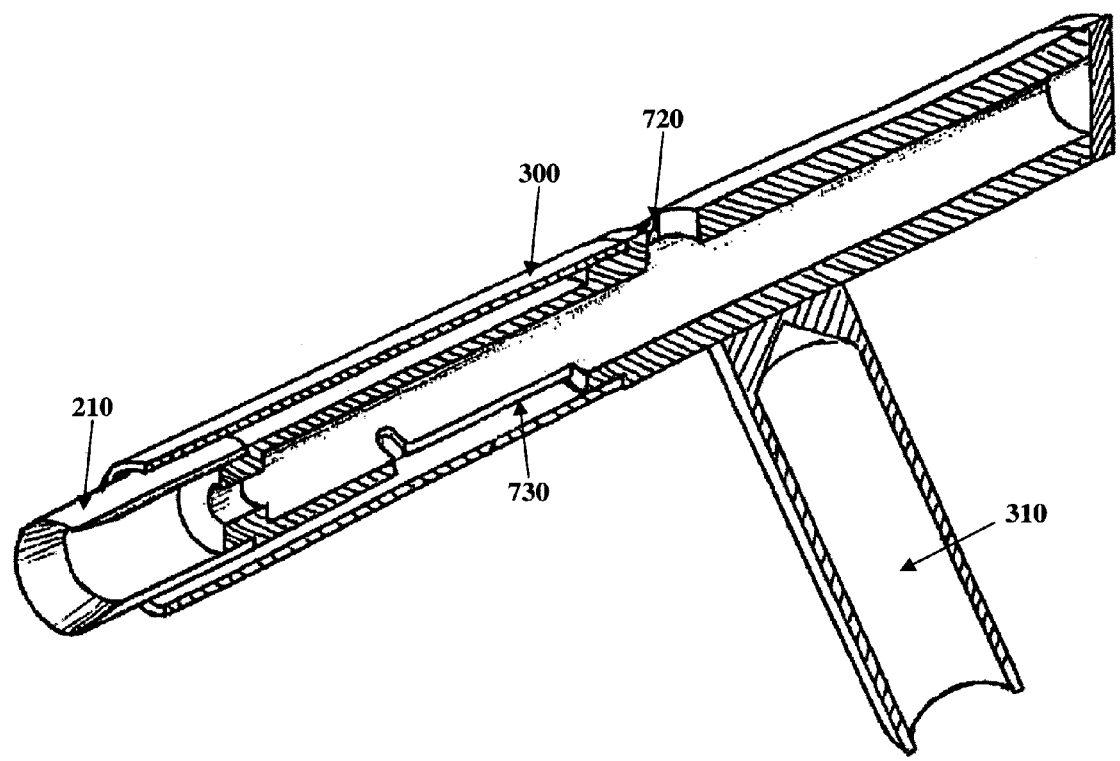

FIG. 21A to FIG. 21C are components of a preferred embodiment shown in FIGS. 23A-23E, that uses a sequencing element to coordinate the position of retractor element 500 with the expansion of expanding element 530 (FIG. 21B). In this embodiment, the sequencing element is a cam mechanism. The cam mechanism helps to ensure proper use of the applicator during implantation of connector conduit 100 (not shown). As shown in FIG. 21B, retractor element 500, referred to as the retractor assembly, includes cylinder portion 562 integrated therein. The retractor assembly is positioned concentrically within pushing element 300 during use. The retractor assembly contains elements of the cam mechanism formal therein, including cylinder cam slot 710, which is a slot cut completely through the cylinder 562 wall, and a retractor cam follower 760, which may be a pin or screw in cylinder 562 (as shown) or may be an integral part of cylinder 562. Retractor element 500 may include a section of increased diameter such as stopper disk 515 to prevent cutter element 210 from cutting the heart when retractor element 500 is initially inserted. FIG. 21A illustrates plunger 600 (in the form of a sequencing bolt as described below), which is positioned concentrically within cylinder 562 during use. Plunger 600 contains elements of the cam mechanism, including bolt portion 650 with plunger cam follower 750. Plunger cam follower 750 moves within cylinder cam slot 710 and pusher cam slot 720. Plunger 600 includes passage 610 and purge/fill valve 630 (valve body not shown). Valve 630 can be opened to allow fluid flow into and out of passage 610. When closed, valve 630 allows no fluid flow in either direction. Valve 630 may be connected (such as with a catheter) to a reservoir of saline, for example, to purge the expanding element 530, access passage 531 and any other volume in the flow circuit of air before filling these volumes with fluid (such as saline). O-ring groove 620 of plunger 600 contains an o-ring (not shown) to prevent loss of fluid.

FIG. 21C illustrates a pusher assembly, which is made up of rigidly connected components including pushing element 300, cutting element 210, and handle 310. The pusher assembly contains elements of the cam mechanism, including pusher cam slot 720 and retractor cam slot 730. The pusher cam slot 720 is a slot cut completely through the pushing element 300 wall to accommodate plunger cam follower 750.

Figure 22A:
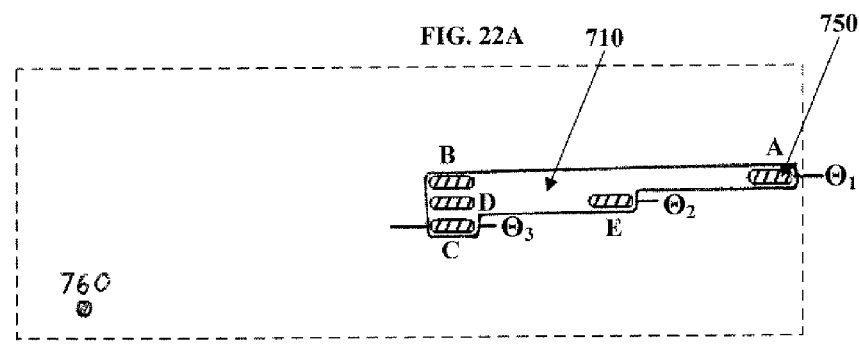
FIGS. 22A-22C is the sequencing cam mechanism in various states.
Figure 22B:
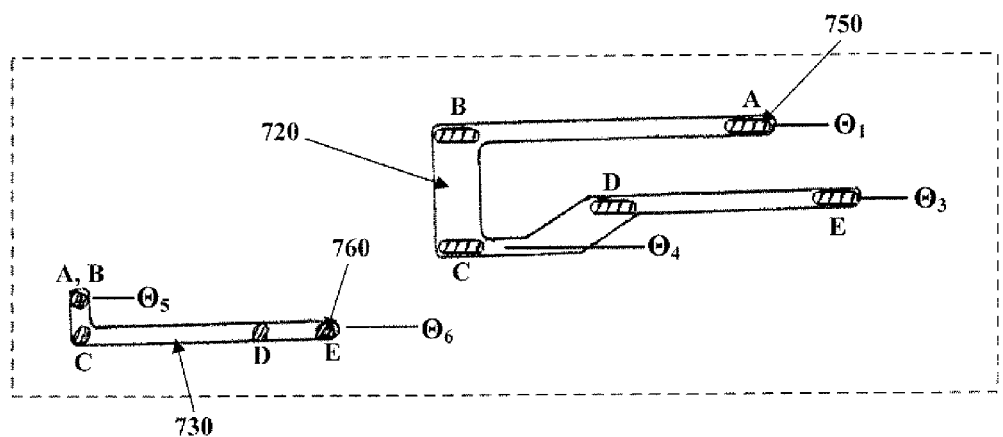
Figure 22C:
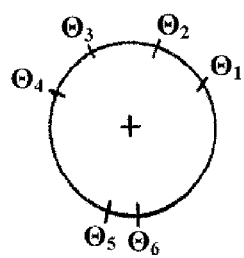

FIG. 22A to FIG. 22C illustrate operation of the cam mechanism. FIG. 22A illustrates cylinder cam slot 710 cut into cylinder 562 of FIG. 21B. Cylinder cam slot 710 contains three interconnected axial cam slots at angles $\theta_1$, $\theta_2$ and $\theta_3$ around the circumference of cylinder 562, as further illustrated in FIG. 22C. The axial cam slot at each angle corresponds to a range of allowable axial positions of plunger 600 within cylinder 562. At angle $\theta_1$, the axial length of the cam slot corresponds to the maximum stroke of plunger 600 within cylinder 562. This maximum stroke allows filling the expanding element 530 from minimum volume to maximum volume. At angle $\theta_2$, the axial cam slot allows plunger 600 movement to provide expanding element 530 volumes ranging from maximum volume to an intermediate volume (at an intermediate stroke) that is greater than minimum volume but less than maximum volume. At angle $\theta_3$, the axial cam slot retains plunger 600 at the position of maximum volume of the expanding element 530. FIG. 22A also illustrates positions A, B, C, D and E of plunger cam follower 750 within cylinder cam slot 710 during the steps of operation.

FIG. 22B illustrates pusher cam slot 720 and retractor cam slot 730 cut into the pusher assembly of FIG. 21C. FIG. 22B also illustrates positions A, B, C, D and E of plunger cam follower 750 within pusher cam slot 720 and retractor cam follower 760 within retractor cam slot 730 during the steps of operation. FIG. 22C illustrates angles $\theta_1$ to $\theta_6$ for cylinder 562 and the pusher assembly. For purposes of description, the value of the angles increases from $\theta_1$ to $\theta_6$. Pusher cam slot 720 includes angles $\theta_1$ and $\theta_3$, which may correspond with angles $\theta_1$ and $\theta_3$ of cylinder 562 (see FIG. 22A). Pusher cam slot 720 includes angle $\theta_4$, which is larger than $\theta_3$. The axial length of pusher cam slot 720 from position A to position B corresponds to the maximum stroke of the plunger 600, as described above. The axial length of pusher cam slot 720 from position C to position E corresponds to the intermediate stroke (as described above) plus the axial distance traversed by retractor cam follower 760 from position C to position E in retractor cam slot 730. Retractor cam slot 730 includes angles $\theta_5$ and $\theta_6$. Positions A and B at angle $\theta_5$ prevent compression spring 540 from displacing cylinder 562 within the pusher assembly.

In operation, retractor cam slot 730 controls the motion of cylinder 562 within the pusher assembly. As shown in FIG. 22A and FIG. 22B, when plunger cam follower 750 (of sequencing bolt 600) is moved circumferentially from position B to position C in both cylinder cam slot 710 and pusher cam slot 720, retractor cam follower 760 is forced from position B to position C in retractor cam slot 730, which allows compression spring 540 (see FIG. 18) to push cylinder 562 axially within the pusher assembly. Retractor cam follower 760 within retractor cam slot 730 holds cylinder 562 at a constant angular position relative to the pusher assembly during movement from position C to positions D and E; therefore, movement of plunger cam follower 750 from position C to position D within pusher cam slot 720 forces cam follower 750 into the axial slot corresponding to angle $\theta_2$ of cylinder 562.

Figure 23A:
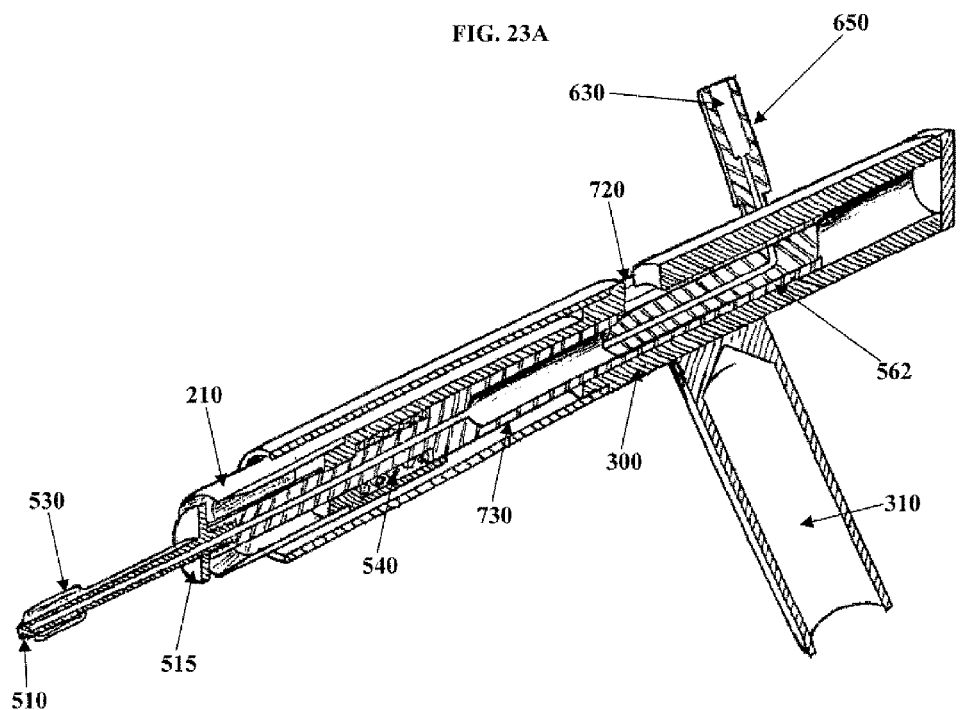
FIGS. 23A-23E illustrate an applicator in various states.
Figure 23B:
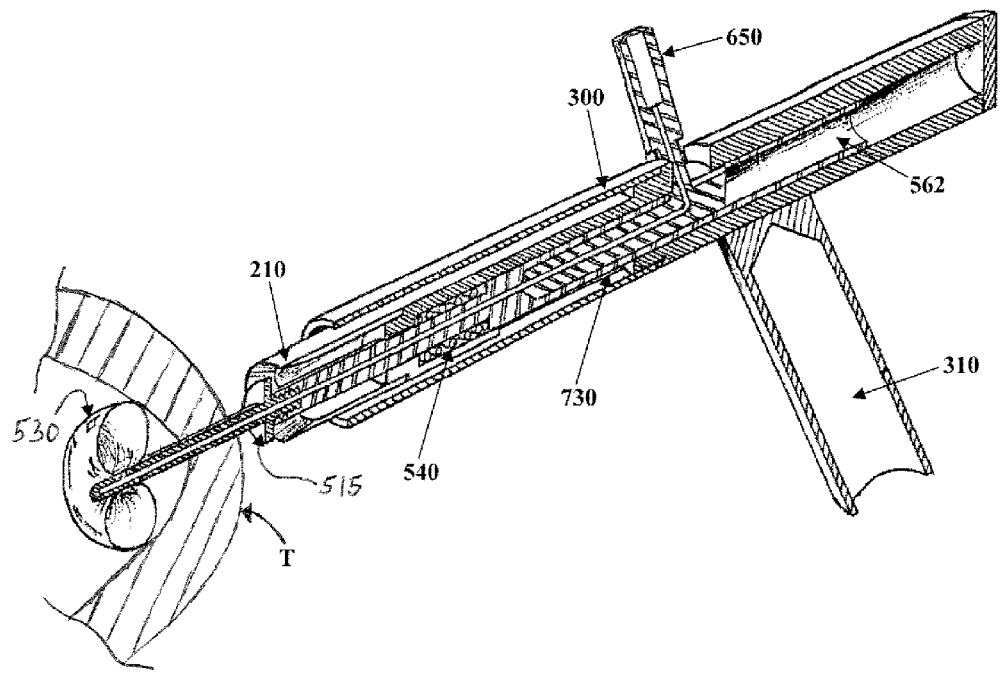
Figure 23C:
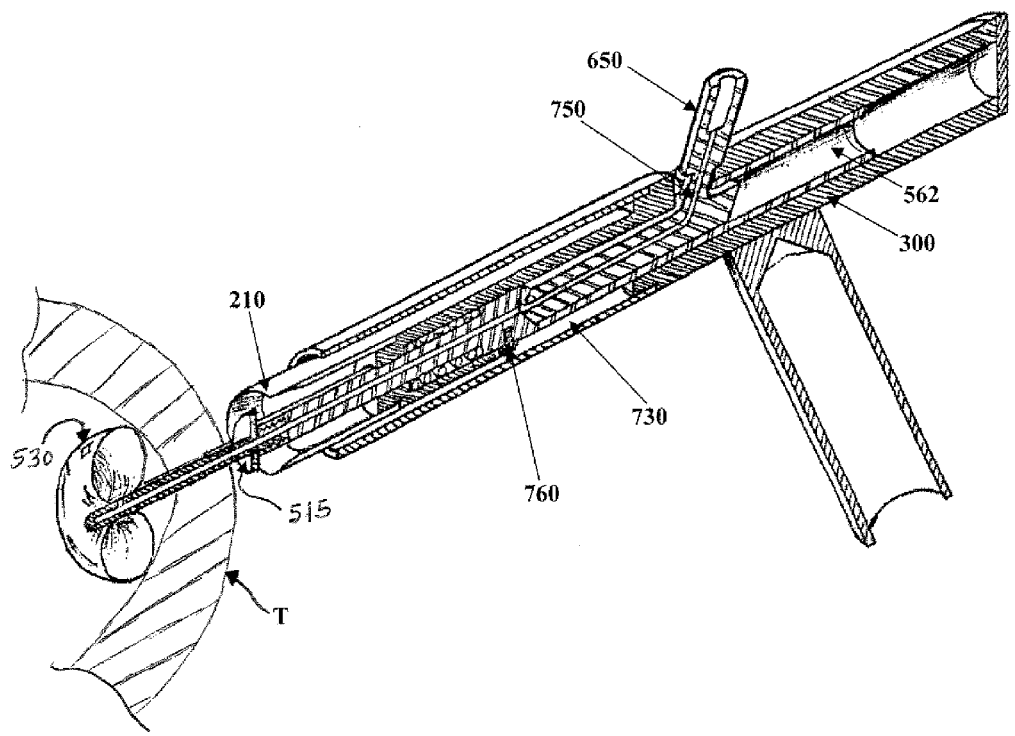
Figure 23D:
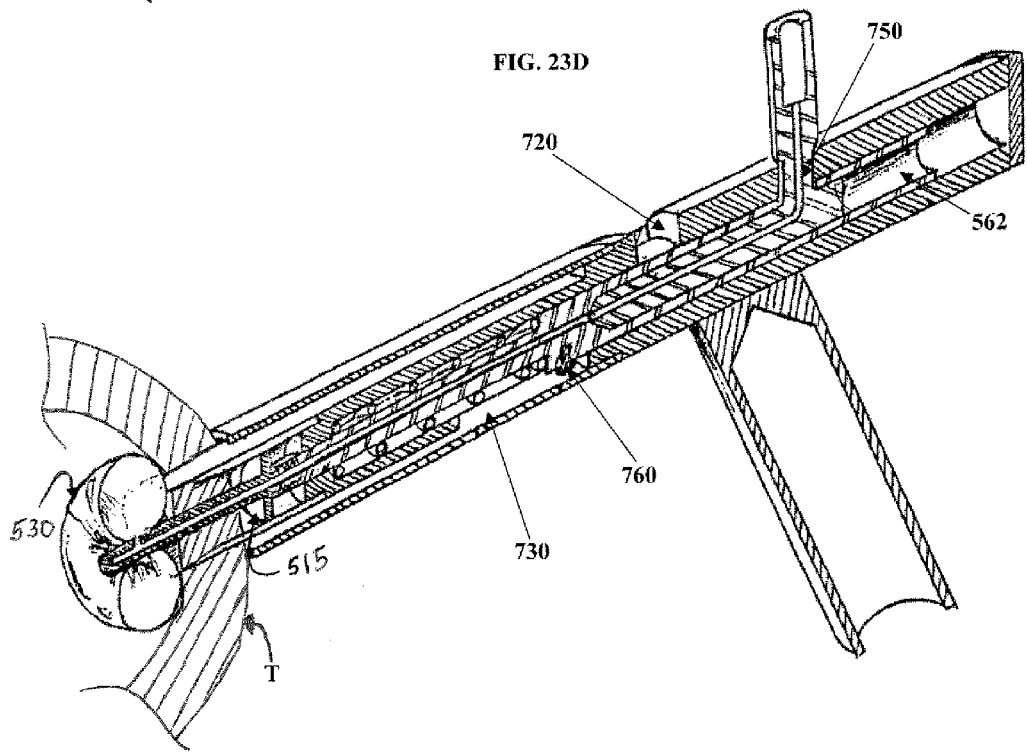
Figure 23E:
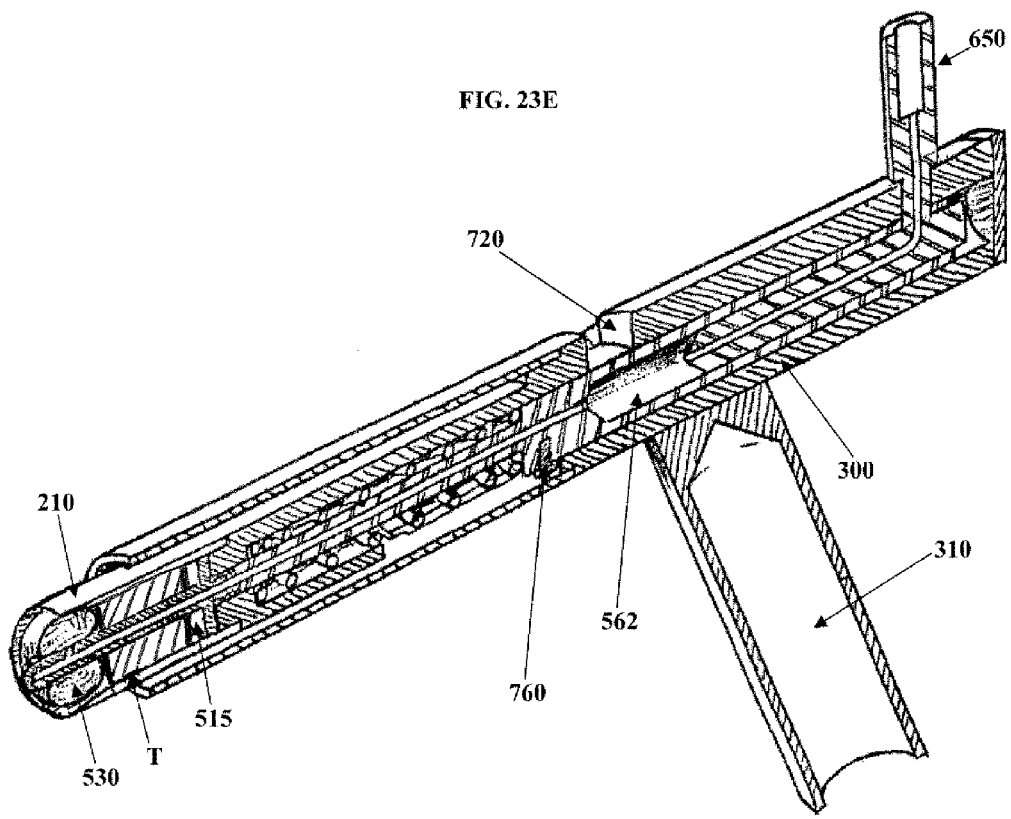

Referring to FIGS. 23A to 23E, the applicator of the present invention is shown at various steps during use. Note that these figures do not include details of the locking means to securely hold the connector conduit 100. FIG. 23A to FIG. 23E correspond to positions A to E, respectively, which are described in FIG. 22A to FIG. 22C. Recognizing that individual surgeons may find alternative steps to properly use the invention, a representative sequence of steps for use of the applicator to implant a connector conduit is described. These steps include first preparing the applicator with the connector conduit. With the retractor assembly in the fully extended position as shown in FIG. 23A, a mounting and folding tool 900 is positioned into the coring element 210, as shown in FIG. 19. The connector conduit 100 of FIG. 14 is then loaded into the applicator by sliding connector conduit 100 over the folding tool 900 until sewing flange 170 contacts notch 421 (see FIG. 17). The connector conduit is then locked into place using the locking means. Tool 900 is then removed. A catheter is attached to purge/fill valve 630 and to a reservoir of saline. Valve 630 is opened. Sequencing bolt 600 is then moved back and forth from position A to position B several times to purge the fluid system of air and to fill the system with fluid, such as saline. Once the air is purged, sequencing bolt 600 is placed at position A, and tool 900 is again positioned into the coring element 210—this time to squeeze fluid from the balloon and to fold the balloon. When tool 900 is in place, valve 630 is closed, and the catheter is removed. Tool 900 is removed. The applicator with connector conduit is now ready for use, as shown in FIG. 23A.

Before implanting the connector conduit 100 into the ventricle wall, the portion of the prosthesis that includes the prosthetic valve or ventricular assist device, as examples, is connected to the aorta. This portion of the prosthesis also includes the female end of quick connect coupler 180. By implanting this portion of the prosthesis first, the time between insulting the heart by cutting a hole and beginning blood flow through the complete prosthesis is minimized.

A template with similar dimensions as connector conduit 100 is placed on the apex of the heart, and a marker is used to trace the circular outline of the connector onto the apex, in the planned location of insertion. Multiple (8 to 12) large pledgeted sutures (mattress sutures) of for example, 2-0 prolene, are placed in the apex surrounding the marked circle. With the connector conduit 100 loaded in the applicator of FIG. 23A, the sutures are brought through sewing flange 170 of the connector conduit 100. A knife is used to make a stab wound in the apex at the center of the circle. With the applicator in the position shown in FIG. 23A, blunt tip 510 of retractor element 500 is inserted into the stab wound and pushed through the apex into the left ventricle chamber until stopper disk 515 contacts the epicardium (outside surface of the heart). Sequencing bolt 600 is moved from position A to position B to inflate the balloon behind tissue T of the heart wall (see FIG. 23B). The surgeon moves sequencing bolt 600 from position B to position C (see FIG. 23C) and then releases sequencing bolt 650. Beginning at position C of FIG. 23C, compression spring 540 pushes the retractor assembly from position C to position D (see FIG. 23D). When the retractor assembly moves from position C to position D, tissue T of the heart wall is first sandwiched between the balloon and the sharpened edge of the coring element 210a. By the surgeon using handle 310 to apply axial force and back-and-forth rotary motion, the sharpened edge of the coring element 210a cuts though the heart wall to form a plug of tissue T that resides in the coring element 210. At position D, the retractor assembly has been retracted until the balloon is in contact with coring element 210 and the tissue plug is fully within coring element 210. Also at position D, cylinder cam slot 710 has forced plunger cam follower 750 circumferentially to angle $\theta_2$, thereby allowing deflation of the balloon to begin. Between position D (FIG. 23D) and position E (FIG. 23E), the balloon deflates to the intermediate volume (described earlier), and the retractor assembly retracts to its final position. If necessary, the surgeon may pull sequencing bolt 600 to its final position E.

Connector conduit 100 is now fully implanted. The sutures are tied, and hemostasis is checked. Additional sutures may be placed if needed. The locking means (not shown) holding the connector conduit in the applicator is released, and the applicator is partially removed to a position where a clamp can be placed directly on collapsible graft 160a to prevent blood flow through the conduit 160. Once the clamp is in place, the applicator may be completely removed from connector conduit 100. The male and female ends of quick connect coupler 180 may now be connected. Umbilical tape 187 may be tied around graft extension 186a to reduce any blood leakage, and stay sutures may be used to secure graft extension 186a to outer fabric 165. Once the flow passage of the prosthesis is purged of air, the clamp may be released to allow blood flow through the prosthesis. Flexible bend 140 is formed by pulling threads 143 and tying a knot. The connector conduit 100 is now fully implanted.

Figure 24:
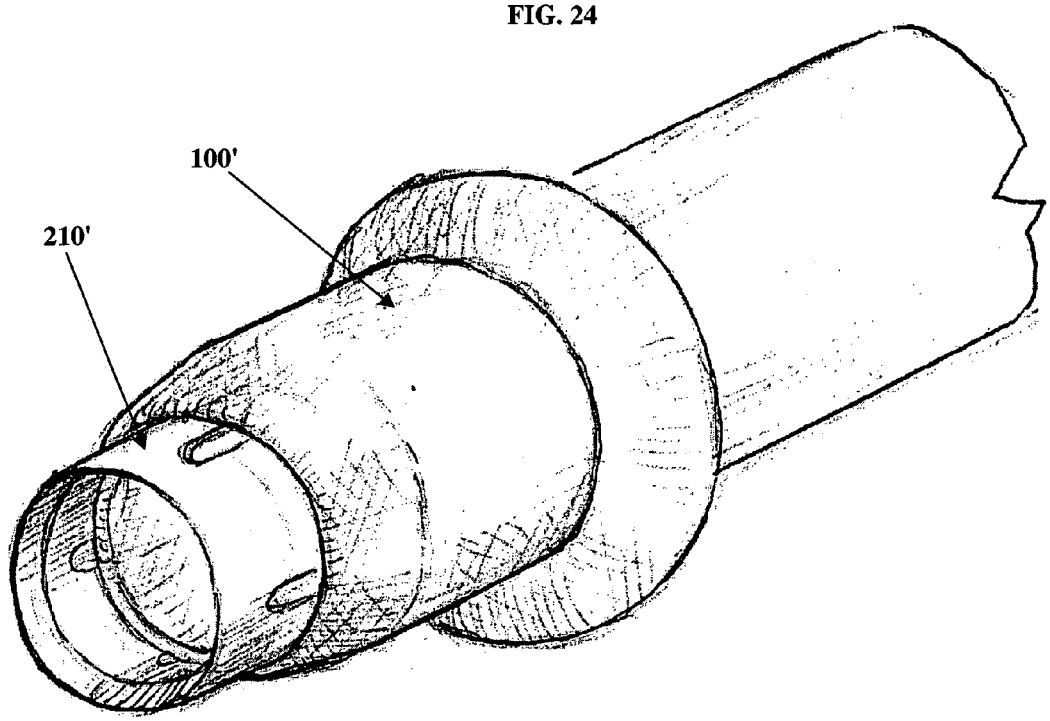
FIG. 24 is a perspective view of an integrated connector conduit and cutting elements.
Figure 25:
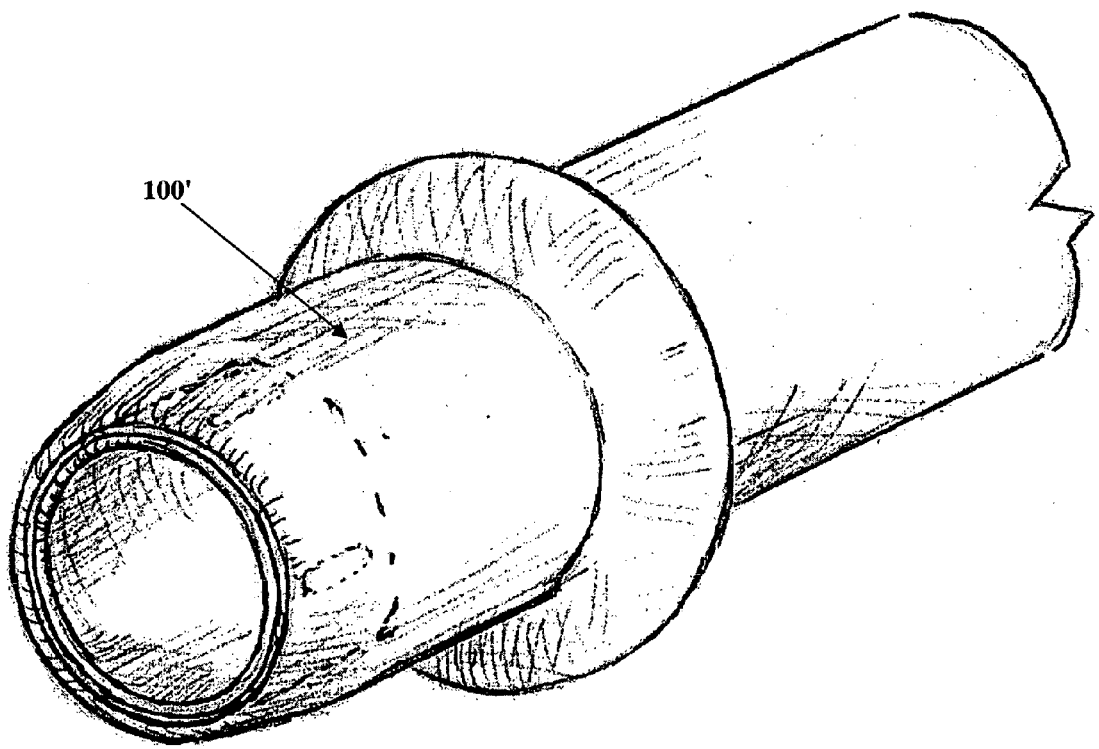
FIG. 25 is the device of FIG. 24 with the cutting element withdrawn.
Figure 24A:
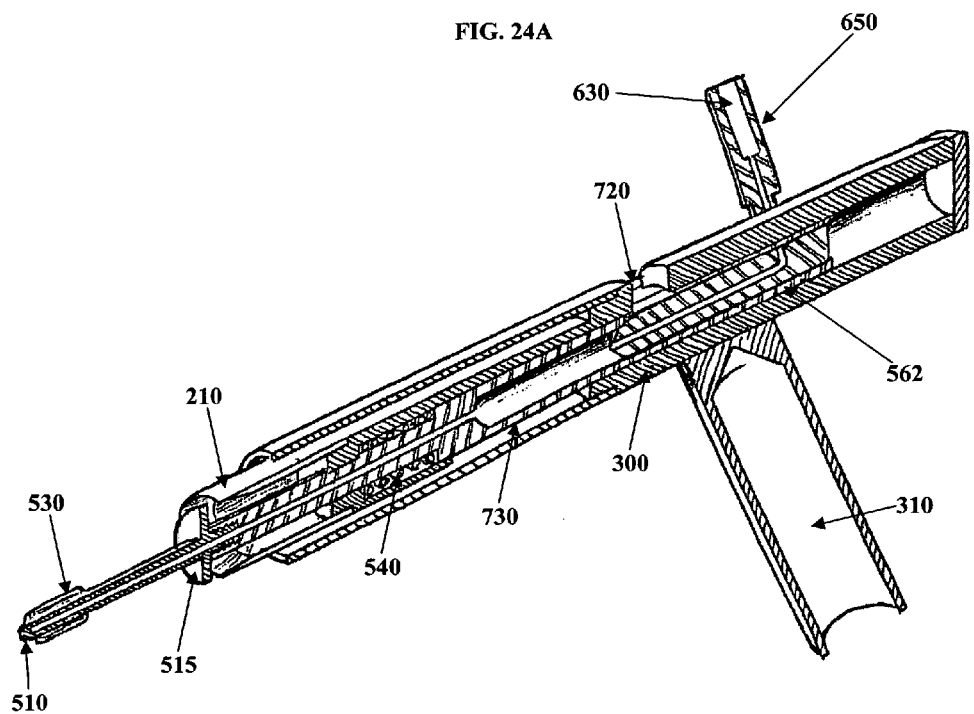
Figure 24B:
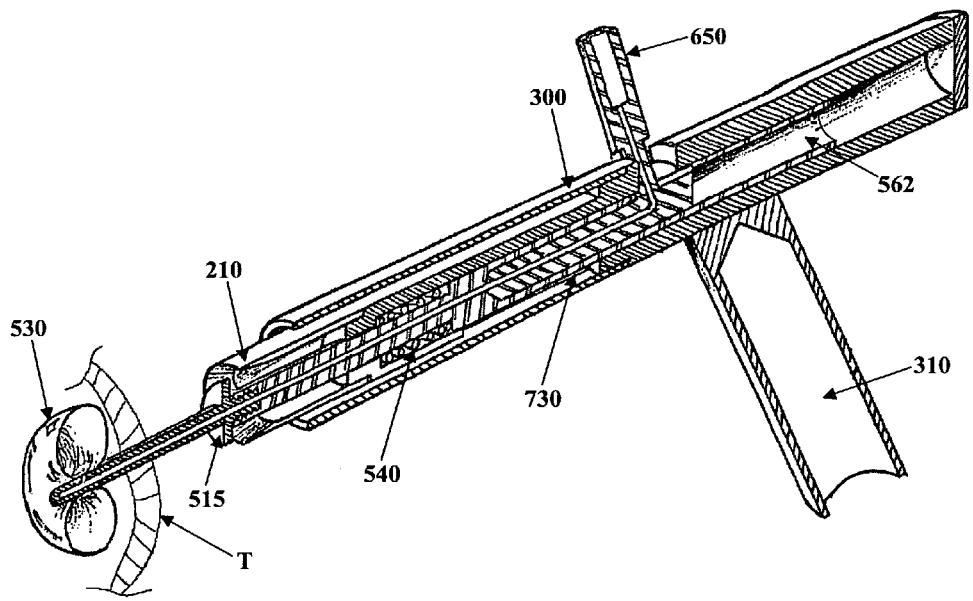
Figure 24C:
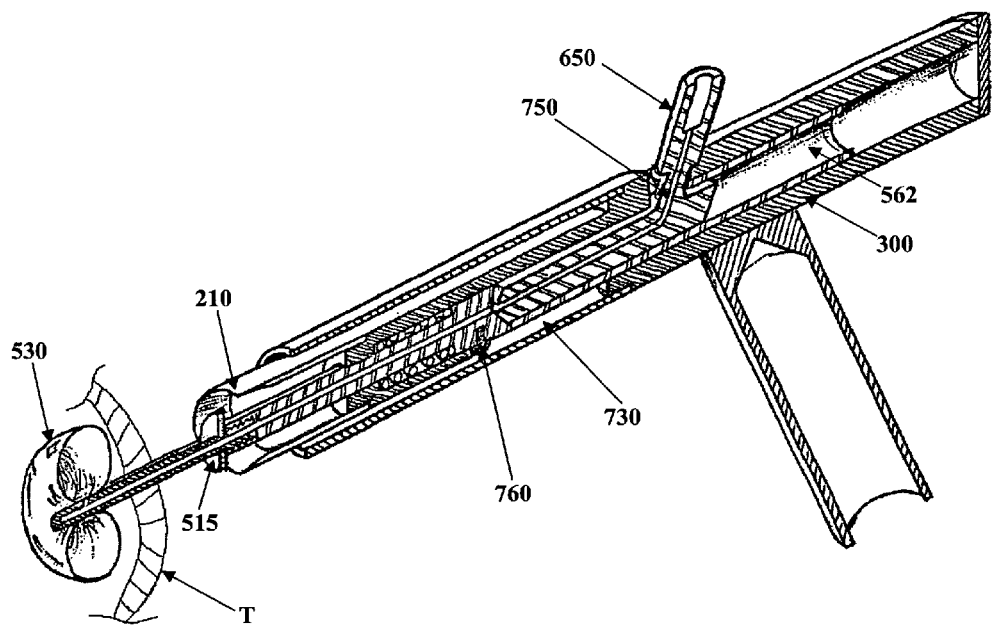
Figure 24D:
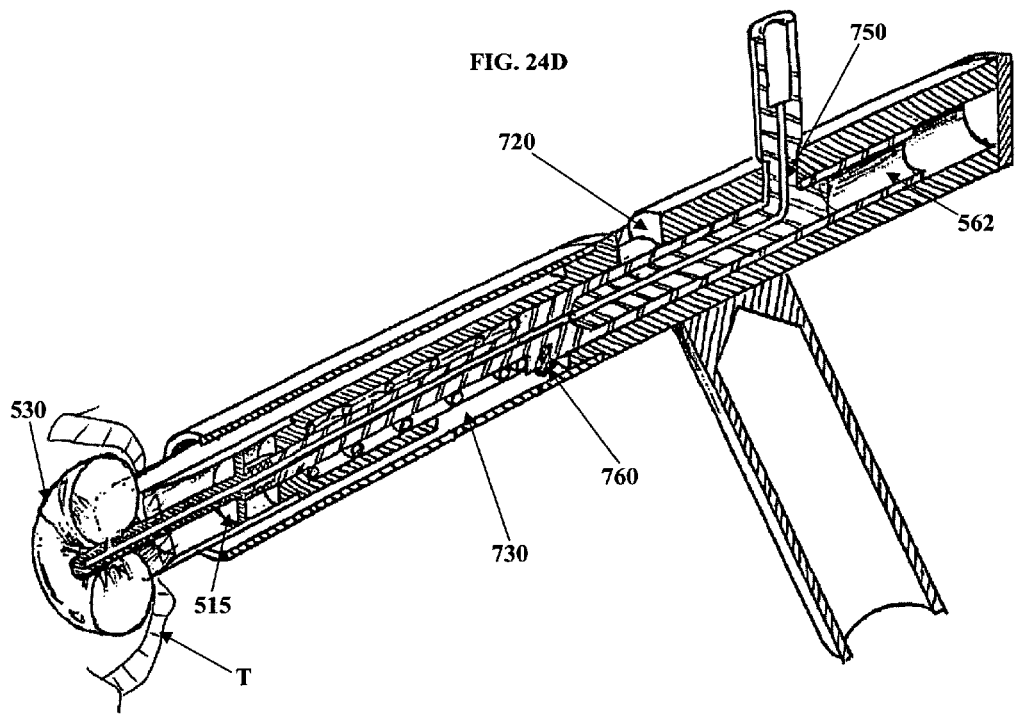
Figure 24E:
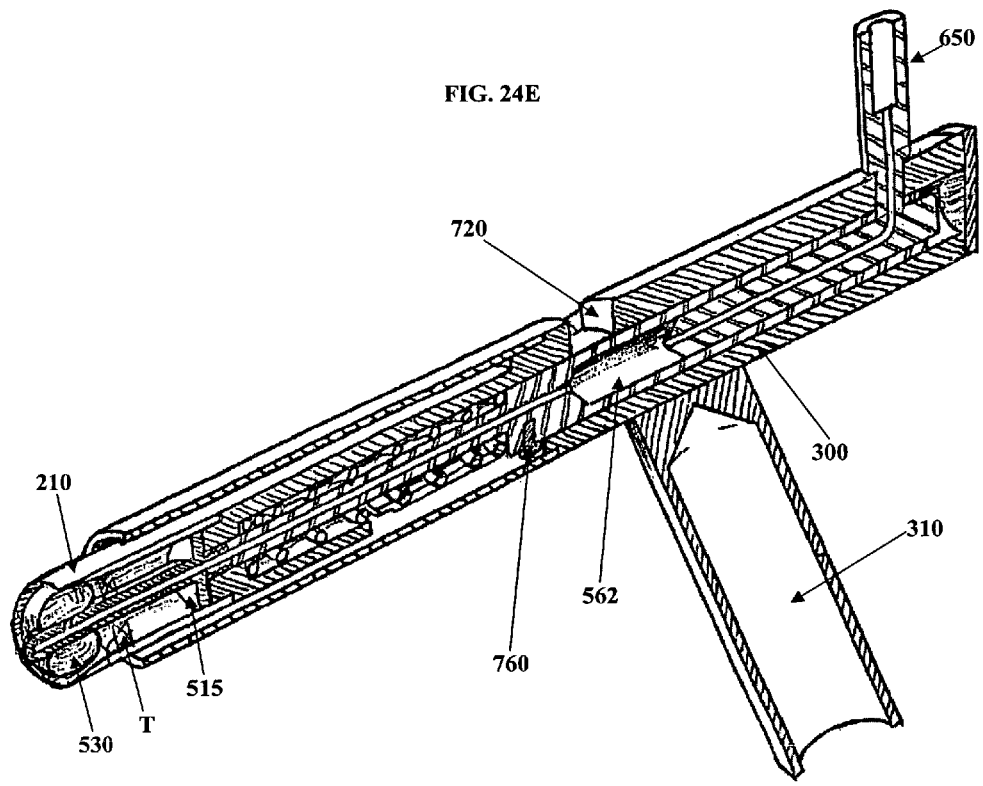
Figure 27D:
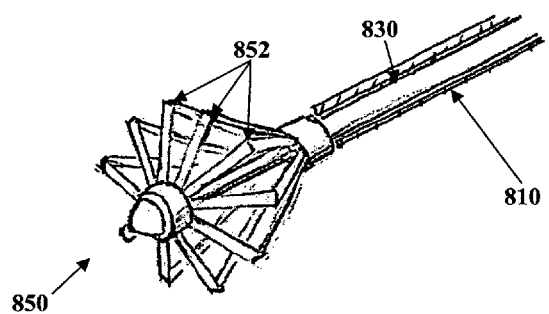
Figure 25:
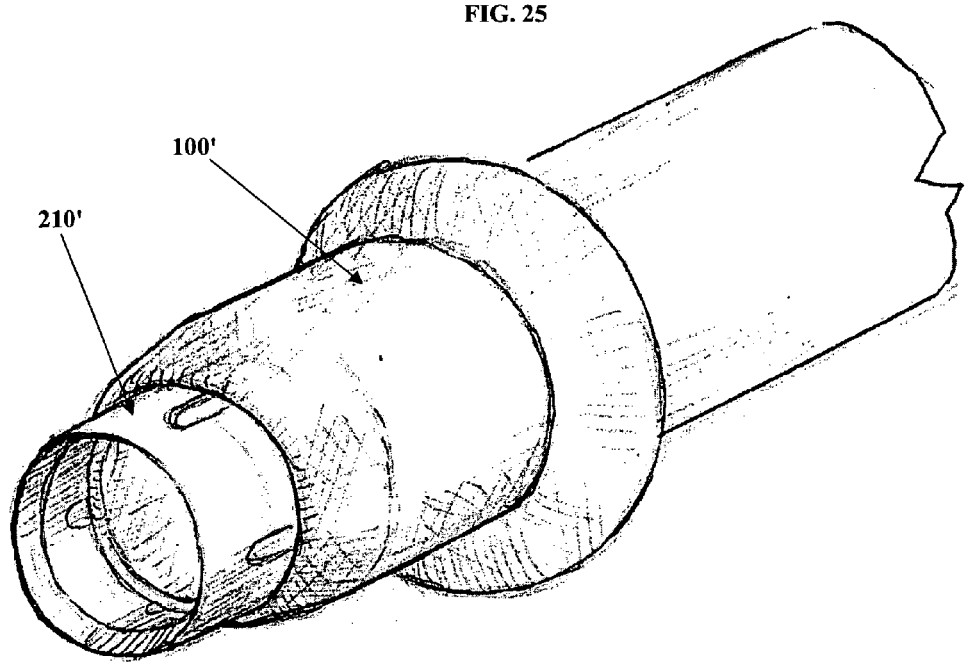
Figure 26:
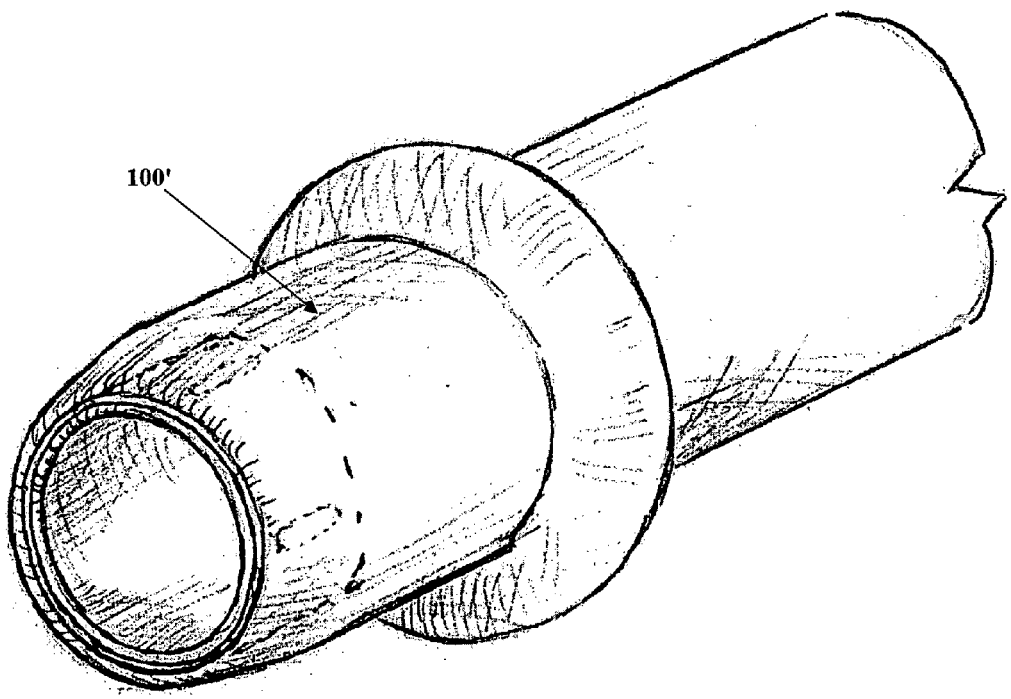
Figure 27A:
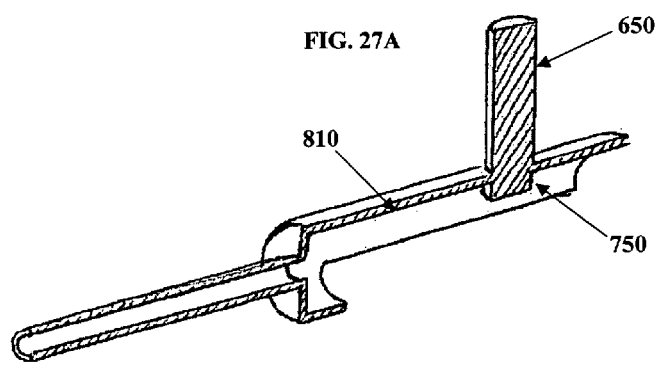
Figure 27B:
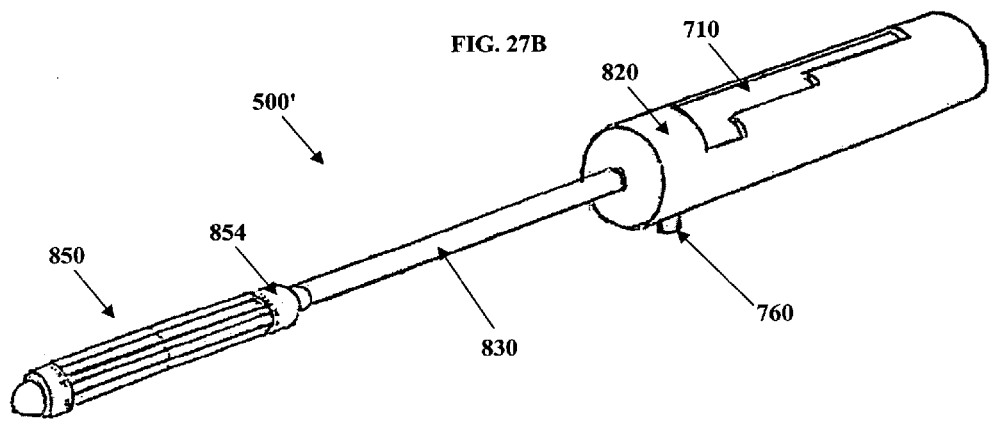
Figure 27C:
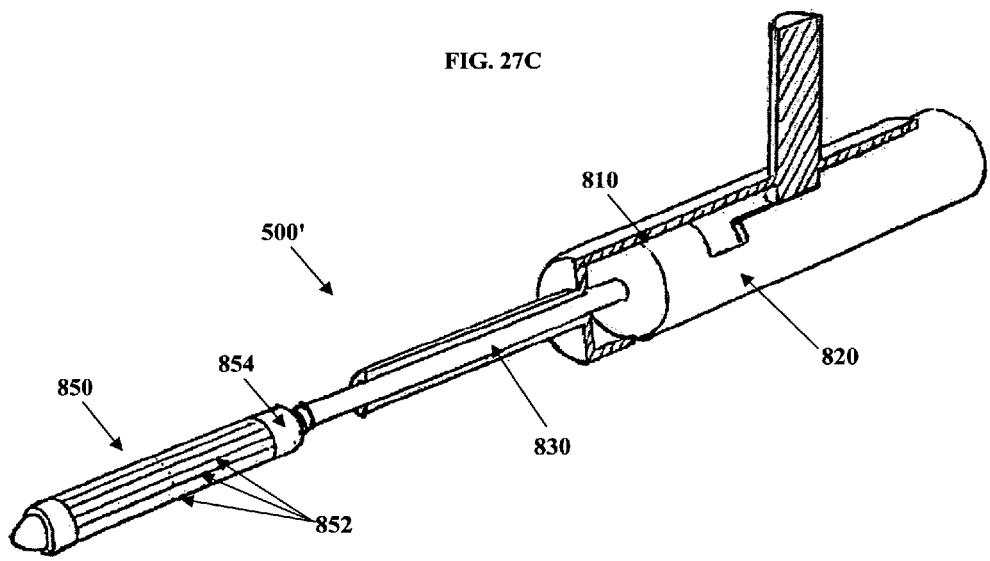

As illustrated in FIG. 24, an alternative embodiment can use a connector conduit having an integral hole forming element. Hole forming element 210' is integrally formed, i.e. formed as a single component, with respect to connector conduit 100'. Connector conduit 100' can be loaded on an applicator (not having a separate hole forming element) in a manner similar to that disclosed above. After forming the hole and inserting the connector conduit into the hole, hole forming element 210' can be withdrawn into a distal end of connector conduit 100', as illustrated in FIG. 25, to reduce the possibility of unintended tissue damage. Such withdrawal can be accomplished by the sequencing means, a manual mechanism on the applicator, or with a separate instrument.

Figure 26D:
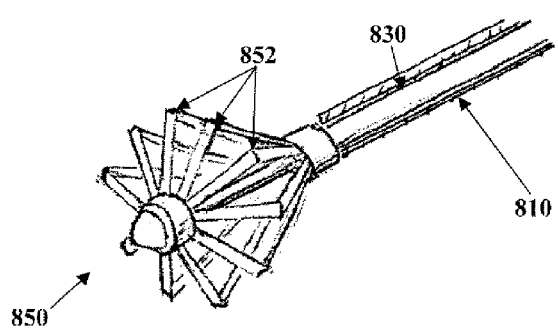
FIG. 26A-26D illustrate components of a retractor having an expandable umbrella element.

In the preferred embodiment described above, the expansion element is a balloon. However, an alternative expansion element, in the form of an umbrella mechanism, is illustrated in FIGS. 26A-26D. Retractor 500' includes cylinder 810 (shown in cross section), and piston element 820 slideably disposed in cylinder 810. Bolt 650 having follower 750 is formed on cylinder 810. Shaft 830 extends from piston element 820 and has umbrella mechanism 850 formed on an end thereof. Umbrella mechanism 850 included plural bendable leaf elements 852 that are fixed to shaft 830 at the end of shaft 830. Leaf elements 852 are fixed to ring 854 at the other end thereof. Ring 854 is slideably disposed on shaft 830. Accordingly, movement of shaft 830 to the right in the FIGS. causes ring 854 to be pushed toward the end of shaft 830 as ring 854 abuts an end of cylinder 810, as shown in FIG. 26D. Slot 710 guides follower 750, and bolt 650 cooperates with remaining elements in the sequencing mechanism in the manner described above, to coordinate the expansion state of expansion element 850.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A connector conduit in combination with an applicator for forming a hole in a wall of a hollow organ and for inserting the connector conduit into the hole to facilitate connection of the connector conduit to the hollow organ, said combination comprising:
   a hole forming element adapted to form a hole in the wall of the organ, said hole forming element including a cutting element on a distal end thereof;
   a retractor element disposed at least partially within said hole forming element, said retractor element comprising a tip at a distal end thereof adapted to penetrate the wall of the organ, and an expansion element positioned near the distal end, said expansion element having a plurality of expansion states;
   a sequencing means for coordinating expansion of said expansion element between said expansion states based on the position of said retractor element relative to said hole forming element;
   a mounting element coupled to said hole forming element, said mounting element being configured to support a connector conduit, and
   a connector conduit supported on said mounting element, whereby said connector conduit is positioned relative to said cutting element such that, when the hole is formed in the wall of the hollow organ, said connector conduit is inserted through the wall of the hollow organ, thereby facilitating connection of said connector conduit to the hollow organ.

2. The combination of the connector conduit and the applicator of claim 1, wherein said cutting element is a cutting blade.

3. The combination of the connector conduit and the applicator of claim 1, further comprising an occluding means for preventing excessive blood loss while the connector conduit is inserted into the hollow organ, such that the hollow organ remains at substantially normal physiological pressures during insertion of the connector conduit into the hollow organ.

4. The combination of the connector conduit and the applicator of claim 3, wherein said occluding means comprises an outer diameter of at least a portion of said retractor element and an inner diameter of at least a portion of said hole forming element.

5. The combination of the connector conduit and the applicator of claim 1, wherein the hollow organ is a beating heart.

6. The combination of the connector conduit and the applicator of claim 1, wherein said cutting element extends from said connector conduit whereby, when a hole is formed in the wall of the hollow organ with said cutting element, said connector conduit is inserted through the wall of the hollow organ in a single motion.

7. The combination of the connector conduit and the applicator of claim 1, wherein the position of said connector conduit on said mounting element is fixed relative to said hole forming element.

8. The combination of the connector conduit and the applicator of claim 1, wherein the distal end of said retractor element defines a blunt tip.

9. The combination of the connector conduit and the applicator of claim 1, wherein said mounting element has a diameter that is substantially equal to an inner diameter of said connector conduit.

10. The combination of the connector conduit and the applicator of claim 1, wherein said retractor element includes a protective stopper element disposed distally of said cutting element when said retractor element is in a distal position with respect to said cutting element to thereby protect tissue from being damaged by said cutting element during insertion of said retractor element into the organ.

11. The combination of the connector conduit and the applicator of claim 1, wherein said plurality of expansion states include an unexpanded state, a fully expanded state, and at least one partially expanded state.

12. The combination of the connector conduit and the applicator of claim 1, wherein said expansion element is a balloon.

13. The combination of the connector conduit and the applicator of claim 12, wherein said balloon, when substantially fully expanded, is in the shape of a circular toroid.

14. The combination of the connector conduit and the applicator of claim 1, wherein said expansion element is an umbrella mechanism.

15. The combination of the connector conduit and the applicator of claim 1, wherein said sequencing means comprises a means for expanding said expansion element between said plurality of expansion states.

16. The combination of the connector conduit and the applicator of claim 15, wherein said means for expanding comprises a syringe in fluid communication with said expansion element.

17. The combination of the connector conduit and the applicator of claim 15, wherein said means for expanding comprises a cylinder having a piston slideable therein and coupled to said expansion element.

18. The combination of the connector conduit and the applicator of claim 15, wherein said retractor element comprises a cylinder portion and a retractor mounting portion extending from a distal end of said cylinder portion, said expansion element being disposed on said retractor mounting portion, and wherein said sequencing means comprises a sequencing bolt coupled to said means for expanding.

19. The combination of the connector conduit and the applicator of claim 18, further comprising a pusher assembly comprising a pushing element configured to transmit axial and torsional force to said connector conduit, said sequencing means further comprising a first slot formed in said pusher assembly, said sequencing bolt extending through said first slot and being movable in said first slot.

20. The combination of the connector conduit and the applicator of claim 18, wherein said sequencing means further comprises a syringe in fluid communication with said expansion element, and wherein said syringe is in fluid communication with said expansion element via an axial passageway defined in said retractor mounting portion.

21. The combination of the connector conduit and the applicator of claim 20, wherein said sequencing bolt has a passage formed therethrough that is in fluid communication with said syringe to facilitate purging and filling of said expansion element.

22. The combination of the connector conduit and the applicator of claim 1, wherein said sequencing means comprises means for moving said retractor element relative to said hole forming element whereby said expansion element is moved from a position distally outside of said hole forming element to a position at least partially disposed within said hole forming element.

23. The combination of the connector conduit and the applicator of claim 1, further comprising a pusher assembly coupled to said hole forming element, said pusher assembly comprising a pusher element configured to transmit axial and torsional force applied by a surgeon to said connector conduit, whereby the surgeon can cut a hole in the wall of the hollow organ and insert said connector conduit into the organ with the same motion.

24. The combination of the connector conduit and the applicator of claim 23, wherein said pusher assembly further includes a handle attached to said pushing element for facilitating application of axial and torsional forces necessary to cut the tissue and position said connector conduit in the wall of the hollow organ.

25. The combination of the connector conduit and the applicator of claim 23, further comprising an indexing element formed on said connector conduit and a mating element formed on said pusher assembly to maintain said connector conduit in a predetermined position with respect to said hole forming element during cutting of the tissue and insertion of said connector conduit in the wall of the hollow organ.

26. The combination of the connector conduit and the applicator of claim 1, wherein said sequencing means comprises a cam mechanism.

27. The combination of the connector conduit and the applicator of claim 1, wherein said sequencing means comprises a gear mechanism.

28. The combination of the connector conduit and the applicator of claim 1, wherein said sequencing means comprises at least one servo mechanism and a controller operatively coupled to said at least one servo mechanism.

29. The combination of the connector conduit and the applicator of claim 28, wherein said controller comprises a microprocessor based device.

30. The combination of the connector conduit and the applicator of claim 29, further comprising a button operatively coupled to said sequencing means for activating said sequencing means upon depression of the button to thereby accomplish steps of a procedure for implanting said connector conduit within the organ wall.

31. The combination of the connector conduit and the applicator of claim 1, wherein, in at least one of said expansion states, said expansion element has a diameter that is smaller than the diameter of said hole forming element.

32. The combination of the connector conduit and the applicator of claim 1, wherein, in at least one of said expansion states, said expansion element has a diameter that is larger than the diameter of said cutting element.

33. The combination of the connector conduit and the applicator of claim 1, wherein, in at least one of said expansion states, said expansion element has a diameter that is smaller than the diameter of said hole forming element, and large enough to cause said expansion element to retain a tissue plug extracted from the hole formed in the wall of the hollow organ within said hole forming element, thereby allowing the applicator and the tissue plug to be removed from the wall of the organ after insertion of said connector conduit.

34. The combination of the connector conduit and the applicator of claim 1, further comprising a removable protection element disposed adjacent said cutting element to facilitate loading of said connector conduit onto the applicator prior to a procedure.

35. The combination of the connector conduit and the applicator of claim 1, further comprising a compression tool removable and slidably disposed over said expansion element and to allow said connector conduit to be mounted onto said hole forming element without damage from said cutting element.

36. The combination of the connector conduit and the applicator of claim 1, wherein the relative rotational position of the expansion element and the hole forming element are fixed while the hole is formed by said hole forming element.

37. The combination of the connector conduit and the applicator as recited in claim 1, further comprising means for damping relative motion of the retractor element with respect to the hole forming element.

38. The combination of the connector conduit and the applicator of claim 1, further comprising a biasing element to move said retractor element relative to said hole forming element.

39. The combination of the connector conduit and the applicator of claim 38, wherein said biasing element comprises a spring.

40. An applicator for forming a hole in a wall of a hollow organ and for inserting a connector conduit into the hole to facilitate connection of the connector conduit to the hollow organ, said applicator comprising:
   a hole forming element adapted to form a hole in the wall of the organ, said hole forming element including a cutting element on a distal end thereof;
   a pusher assembly comprising a first slot, a second slot, and a pushing element, said pushing element being configured to transmit axial and torsional force to a connector conduit;
   a retractor element disposed at least partially within said hole forming element, said retractor element comprising:
      a tip at a distal end thereof adapted to penetrate the wall of the organ;
      a cylinder portion;
      a retractor mounting portion extending from a distal end of said cylinder portion;

an expansion element disposed on said retractor mounting portion and positioned near the distal end of said retractor element, said expansion element having a plurality of expansion states; and a retractor follower formed on said retractor element and movably disposed in said second slot of said pusher assembly;

a sequencing means for coordinating expansion of said expansion element between said expansion states based on the position of said retractor element relative to said hole forming element, said sequencing means comprising:

a means for expanding said expansion element between said plurality of expansion states; and a sequencing bolt coupled to said means for expanding, said sequencing bolt extending through said first slot of said pusher assembly and being movable in said first slot of said pusher assembly; and a mounting element coupled to said hole forming element, said mounting element being configured to support a connector conduit, whereby a connector conduit is positioned relative to said cutting element such that, when the hole is formed in the wall of the hollow organ, a connector conduit is inserted through the wall of the hollow organ, thereby facilitating connection of the connector conduit to the hollow organ.

41. The applicator of claim 40, wherein said sequencing means further comprises a cam slot formed in said cylinder portion of said retractor element, said sequencing bolt extending through said cam slot and being movable within said cam slot.

42. The applicator of claim 41, wherein said sequencing bolt is movable between a first and second position in said first slot to move said sequencing bolt in said cylinder portion of said retractor element and coordinate expansion of said expansion element to a fully expanded state while said retractor follower in said second slot remains locked with said retractor element in a fully extended position relative to said hole forming element.

43. The applicator of claim 42, wherein said sequencing bolt is movable between the second position and a third position in said first slot and in said cam slot to lock said expansion element in the fully expanded state.

44. The applicator of claim 43, wherein said sequencing bolt is movable between the third position and a fourth position in said first slot, such that when said sequencing bolt is moved to the fourth position said retractor follower is simultaneously moved within said second slot to enable said retractor element to move with respect to said hole forming element.

45. The applicator as recited in claim 44, wherein movement of said sequencing bolt from the first position to the fourth position can be accomplished manually in a substantially continuous manner.

46. The applicator of claim 44, wherein said sequencing bolt is movable between the fourth position and a fifth position in said first slot, such that said retractor element is simultaneously moved with respect to said hole forming element to position the organ wall between said expansion element and said cutting element, whereby upon manipulation of said pusher assembly, a hole in the tissue is cut by said hole forming element and the connector conduit is moved into the hole.

47. The applicator of claim 46, further comprising means for automatically accomplishing movement of said sequencing bolt between the fourth position and the fifth position.

48. The applicator of claim 46, wherein said sequencing bolt is movable between the fifth position and a sixth position in said first slot and said cam slot, wherein at said sixth position, said sequencing bolt is moved with respect to said cylinder portion, whereby said expansion element is in a partially expanded state, and said retractor element moves in a proximal direction with respect to said hole forming element until said expansion element is at least partially disposed within said hole forming element.

49. The applicator of claim 48, further comprising means for automatically accomplishing movement of said sequencing bolt between said fifth position and said sixth position.

50. The applicator of claim 48, further comprising a biasing element coupled to said retractor element and said pushing element to bias said retractor element in a proximal direction with respect to said pushing element and thereby automatically move said sequencing bolt from said fourth position to said fifth position and from said fifth position to said sixth position.

51. The applicator as recited in claim 50, wherein said biasing element is a spring.

52. The applicator as recited in claim 41, wherein said sequencing means comprises means for causing the elements to assume the following states in seriatim;
 a) a first state in which the sequencing bolt is moved in the first slot and the cam slot to expand the expansion element while the retractor element is locked in a fully extended position relative to the hole forming element;
 b) a second state in which the sequencing bolt is moved in the first slot and the cam slot to retain the expansion element as fully expanded;
 c) a third state in which the sequencing bolt moves in the first slot and the retractor follower moves in the second slot to release the retractor element and permit a biasing element to move the retractor element toward the hole forming element; and
 d) a fourth state in which the sequencing bolt moves in the first slot while being locked in the cam slot and the retractor follower moves in the second slot to complete forming of the hole and allow insertion of the connector conduit into the hole; and
 e) a fifth state in which the sequencing bolt moves in the first slot and in the cam slot to release the sequencing bolt from a locked position in the cam slot to allow the expansion element to assume the partially expanded state while the expansion element is moved to be at least partially disposed in the hole forming element.

53. The combination of the connector conduit and the applicator of claim 52, wherein said biasing element comprises a spring.

54. An applicator for forming a hole in a wall of a hollow organ and for inserting a connector conduit into the hole to facilitate connection of the connector conduit to the hollow organ, said applicator comprising:

a hole forming element adapted to form a hole in the wall of the organ, said hole forming element including a cutting element on a distal end thereof;

a retractor element disposed at least partially within said hole forming element, said retractor element comprising a tip at a distal end thereof adapted to penetrate the wall of the organ, and an expansion element positioned near the distal end, said expansion element having a plurality of expansion states;

a sequencing means for coordinating expansion of said expansion element between said expansion states based on the position of said retractor element relative to said hole forming element; and a mounting element coupled to said hole forming element, said mounting element being configured to support a connector conduit, whereby the connector conduit is positioned relative to said cutting element such that, when the hole is formed in the wall of the hollow organ, the connector conduit is inserted through the wall of the hollow organ, thereby facilitating connection of the connector conduit to the hollow organ, wherein said sequencing means comprises means for causing the elements to assume the following states in seriatim;
   a) a first state where the retractor element is locked in a fully extended position relative to the hole forming element with the expansion element in the unexpanded state;
   b) a second state in which the expansion element is in the fully expanded state and the expansion element moves toward the hole forming element;
   c) a third state in which the hole has been formed and the connector conduit has been inserted; and
   d) a fourth state in which the expansion element is in the partially expanded state and the expansion element is moved to be at least partially disposed in the hole forming element.

* * * * *

UNITED STATES PATENT AND TRADEMARK OFFICE
CERTIFICATE OF CORRECTION

PATENT NO. : 7,510,561 B2
APPLICATION NO. : 11/086577
DATED : March 31, 2009
INVENTOR(S) : Richard M. Beane et al.

It is certified that error appears in the above-identified patent and that said Letters Patent is hereby corrected as shown below:

Sheet 1 of 35, change "Sheet 1 of 35" to -- Sheet 1 of 23 --;

Sheet 2 of 35, change "Sheet 2 of 35" to -- Sheet 2 of 23 --;

Sheet 3 of 35, change "Sheet 3 of 35" to -- Sheet 3 of 23 --;

Sheet 4 of 35, delete this sheet;

Sheet 5 of 35, change "Sheet 5 of 35" to -- Sheet 4 of 23 --;

Sheet 6 of 35, change "Sheet 6 of 35" to -- Sheet 5 of 23 --;

Sheet 7 of 35, delete this sheet;

Sheet 8 of 35, change "Sheet 8 of 35" to -- Sheet 6 of 23 --;

Sheet 9 of 35, change "Sheet 9 of 35" to -- Sheet 7 of 23 --;

Sheet 10 of 35, delete this sheet;

Sheet 11 of 35, delete this sheet;

Sheet 12 of 35, change "Sheet 12 of 35" to -- Sheet 8 of 23 --;

Sheet 13 of 35, change "Sheet 13 of 35" to -- Sheet 9 of 23 --;

Sheet 14 of 35, delete this sheet;

Sheet 15 of 35, change "Sheet 15 of 35" to -- Sheet 10 of 23 --;

Sheet 16 of 35, change "Sheet 16 of 35" to -- Sheet 11 of 23 --;

Signed and Sealed this

Twenty-ninth Day of June, 2010

David J. Kappos
*Director of the United States Patent and Trademark Office*

CERTIFICATE OF CORRECTION (continued)
U.S. Pat. No. 7,510,561 B2

Sheet 17 of 35, delete this sheet;

Sheet 18 of 35, change "Sheet 18 of 35" to -- Sheet 12 of 23 --;

Sheet 19 of 35, change "Sheet 19 of 35" to -- Sheet 13 of 23 --;

Sheet 20 of 35, change "Sheet 20 of 35" to -- Sheet 14 of 23 --;

Sheet 21 of 35, delete this sheet;

Sheet 22 of 35, change "Sheet 22 of 35" to -- Sheet 15 of 23 --;

Sheet 22 of 35, change "FIG. 20" to -- FIG. 19 --;

Sheet 22 of 35, change "FIG. 21" to -- FIG. 20 --;

Sheet 23 of 35, change "Sheet 23 of 35" to -- Sheet 16 of 23 --;

Sheet 24 of 35, change "Sheet 24 of 35" to -- Sheet 17 of 23 --;

Sheet 25 of 35, change "Sheet 25 of 35" to -- Sheet 18 of 23 --;

Sheet 26 of 35, change "Sheet 26 of 35" to -- Sheet 19 of 23 --;

Sheet 27 of 35, change "Sheet 27 of 35" to -- Sheet 20 of 23 --;

Sheet 28 of 35, change "Sheet 28 of 35" to -- Sheet 21 of 23 --;

Sheet 29 of 35, change "Sheet 29 of 35" to -- Sheet 22 of 23 --;

Sheet 30 of 35, delete this sheet;

Sheet 31 of 35, delete this sheet;

Sheet 32 of 35, delete this sheet;

Sheet 33 of 35, delete this sheet;

Sheet 34 of 35, change "Sheet 34 of 35" to -- Sheet 23 of 23 --; and

Sheet 35 of 35, delete this sheet.